United States Patent
Yoshida et al.

(10) Patent No.: US 12,169,957 B2
(45) Date of Patent: Dec. 17, 2024

(54) IMAGE PROCESSING DEVICE, IMAGE PROCESSING METHOD, AND PROGRAM

(71) Applicant: NIKON CORPORATION, Tokyo (JP)

(72) Inventors: Takahiko Yoshida, Tokyo (JP); Moeka Nobuta, Yokohama (JP)

(73) Assignee: NIKON CORPORATION, Tokyo (JP)

( * ) Notice: Subject to any disclaimer, the term of this patent is extended or adjusted under 35 U.S.C. 154(b) by 355 days.

(21) Appl. No.: 17/688,771

(22) Filed: Mar. 7, 2022

(65) Prior Publication Data

US 2022/0270347 A1    Aug. 25, 2022

Related U.S. Application Data

(63) Continuation of application No. PCT/JP2020/032731, filed on Aug. 28, 2020.

(30) Foreign Application Priority Data

Sep. 10, 2019  (JP) .................. 2019-164505

(51) Int. Cl.
  *G06V 10/40*    (2022.01)
  *G06V 10/44*    (2022.01)
  *G06V 20/69*    (2022.01)

(52) U.S. Cl.
  CPC .......... *G06V 10/457* (2022.01); *G06V 20/695* (2022.01); *G06V 2201/03* (2022.01)

(58) Field of Classification Search
  CPC .............. G06V 10/457; G06V 20/695; G06V 2201/03; G06T 2207/10056;
(Continued)

(56) References Cited

U.S. PATENT DOCUMENTS

| 9,495,607 B2 * | 11/2016 | Tombari ................. G06V 10/46 |
| 10,163,218 B2 | 12/2018 | Nakagawa et al. |
| 2009/0154792 A1 | 6/2009 | Sun et al. |
| 2010/0119113 A1 | 5/2010 | Kuleschow et al. |
| 2013/0272596 A1 * | 10/2013 | Xu ....................... G06V 10/426 382/134 |

(Continued)

FOREIGN PATENT DOCUMENTS

| JP | 6015113 B2 | 10/2016 |
| JP | 2020113200 A | 7/2020 |
| WO | 2015/041177 A1 | 3/2017 |

OTHER PUBLICATIONS

Communication forwarding the extended European Search Report dated Aug. 11, 2023 for European Patent Application No. 20863609.2; 11 pages.

(Continued)

*Primary Examiner* — Qian Yang
(74) *Attorney, Agent, or Firm* — SQUIRE PATTON BOGGS (US) LLP

(57) ABSTRACT

An image processing device comprises pixel group setting part that sets plurality of pixel groups including first and second pixel groups, which are not connected to each other, based on image data of first image which shows target object including linear portion; pair setting part that performs setting pair of first and second pixel groups including pixel within predetermined range from first pixel group to calculate connecting degree of second pixel group with respect to first pixel group; and calculation part that calculates connecting degree of pair, wherein predetermined range is search range set based on first distance between first and second pixel groups, or search range set on based on first angle formed between first line segment corresponding to first pixel group and second line segment corresponding to second pixel group, and calculation part calculates first distance or first angle using first distance or first angle.

18 Claims, 31 Drawing Sheets

(58) Field of Classification Search
CPC . G06T 2207/10064; G06T 2207/30024; G06T 2207/30101; G06T 7/187; G06T 7/11; G06T 7/60; C12M 41/36; C12M 1/34; C12M 3/00; C12Q 1/04
See application file for complete search history.

(56) References Cited

U.S. PATENT DOCUMENTS

2018/0247147 A1* 8/2018 Polidor ............... G06T 7/33

OTHER PUBLICATIONS

Zhao, et al., "Automated reconstruction of neuronal morphology based on local geometrical and global structural models", NEUROINFORMATICS; May 6, 2011; vol. 9 Nos. 2-3; pp. 247-261 (correction).

Q. Lau et al., "Simultaneously Identifying All True Vessels From Segmented Retinal Images", IEEE Transactons on Biomedical Engineering, vol. 60, No. 7, Jul. 2013, DOI: 10.1109/TBME.2013.2243447, 8 pages.

Written Opinion and International Search Report issued in corresponding International Patent Application No. PCT/JP2020/032731 on Oct. 20, 2020.

Zhao, et al., "Automated reconstruction of neuronal morphology based on local geometrical and global structural models", NEUROINFORMATICS; May 6, 2011; vol. 9 Nos. 2-3; pp. 247-256.

Notification of First Office Action dated Apr. 28, 2024 for Chinese Patent Application No. 202080074960.6; with English translation, 16 pages.

* cited by examiner (A)

(B)

(A)

(B)

(A)

(B)

(C)

(A)

(B)

(A)

(B)

(A)

(B)

IMAGE PROCESSING DEVICE, IMAGE PROCESSING METHOD, AND PROGRAM

CROSS-REFERENCE TO RELATED APPLICATION

Priority is claimed on Japanese Patent Application No. 2019-164505, filed on Sep. 10, 2019, the content of which is incorporated herein by reference. The present application is a continuation application of International Application PCT/JP2020/032731, filed on Aug. 28, 2020. The contents of the above applications are incorporated herein.

BACKGROUND

Technical Field

The present invention relates to an image processing device, an image processing method and a program.

A method of performing image processing on an image obtained by imaging an object including a linear portion provided with a branch or the like as appropriate has been proposed (see Japanese Patent No. 6015113). In such image processing, it is necessary to analyze how an extracted pixel group corresponds to the linear portion.

SUMMARY

According to a first aspect of the present invention, an image processing device includes a pixel group setting part configured to obtain an image data of a first image which shows a target object including a linear portion from an imaging device, and configured to set a plurality of pixel groups including a first pixel group and a second pixel group, which are not connected to each other, based on the image data when setting a plurality of pixel groups corresponding to the first image in the imaging device; a pair setting part configured to perform setting of a pair of the first pixel group and the second pixel group including a pixel within a predetermined range from the first pixel group, among the plurality of pixel groups, in order to calculate a connecting degree of the second pixel group with respect to the first pixel group; and a calculation part configured to calculate the connecting degree of the pair set by the pair setting part, wherein the predetermined range is a search range set on the basis of a first distance between the first pixel group and the second pixel group, or a search range set on the basis of a first angle formed between a first line segment corresponding to the first pixel group and a second line segment corresponding to the second pixel group, and the calculation part is configured to calculate the first distance or the first angle, and is configured to calculate the connecting degree using the first distance or the first angle.

According to a second aspect of the present invention, an image processing method includes setting process of obtaining an image data of a first image which shows a target object including a linear portion from an imaging device and setting a plurality of pixel groups including a first pixel group and a second pixel group, which are not connected to each other, based on the image data when setting a plurality of pixel groups corresponding to the first image in the imaging device; setting process of setting a pair of the first pixel group and the second pixel group including a pixel within a predetermined range from the first pixel group, among the plurality of pixel groups, in order to calculate a connecting degree of the second pixel group with respect to the first pixel group; and calculating process of calculating the connecting degree of the pair set in the setting process of the pair of the first pixel group and the second pixel group, wherein the predetermined range is a search range set on the basis of a first distance between the first pixel group and the second pixel group, or a search range set on the basis of a first angle formed between a first line segment corresponding to the first pixel group and a second line segment corresponding to the second pixel group, and in the calculating process, the first distance or the first angle is calculated and the connecting degree is calculated by using the first distance or the first angle.

According to a third aspect of the present invention, a program is configured to cause a processing device to perform: pixel group setting processing of obtaining an image data of a first image which shows a target object including a linear portion from an imaging device and setting a plurality of pixel groups including a first pixel group and a second pixel group, which are not connected to each other, based on the image data when setting a plurality of pixel groups corresponding to the first image in the imaging device; pair setting processing of performing setting of a pair of the first pixel group and the second pixel group including a pixel within a predetermined range from the first pixel group, among the plurality of pixel groups, in order to calculate a connecting degree of the second pixel group with respect to the first pixel group, and calculating process of calculating the connecting degree of the pair set in the pair setting processing.

DESCRIPTION OF THE EMBODIMENTS

Hereinafter, an embodiment of the present invention will be described with reference to the accompanying drawings.

First Embodiment

Figure 1:
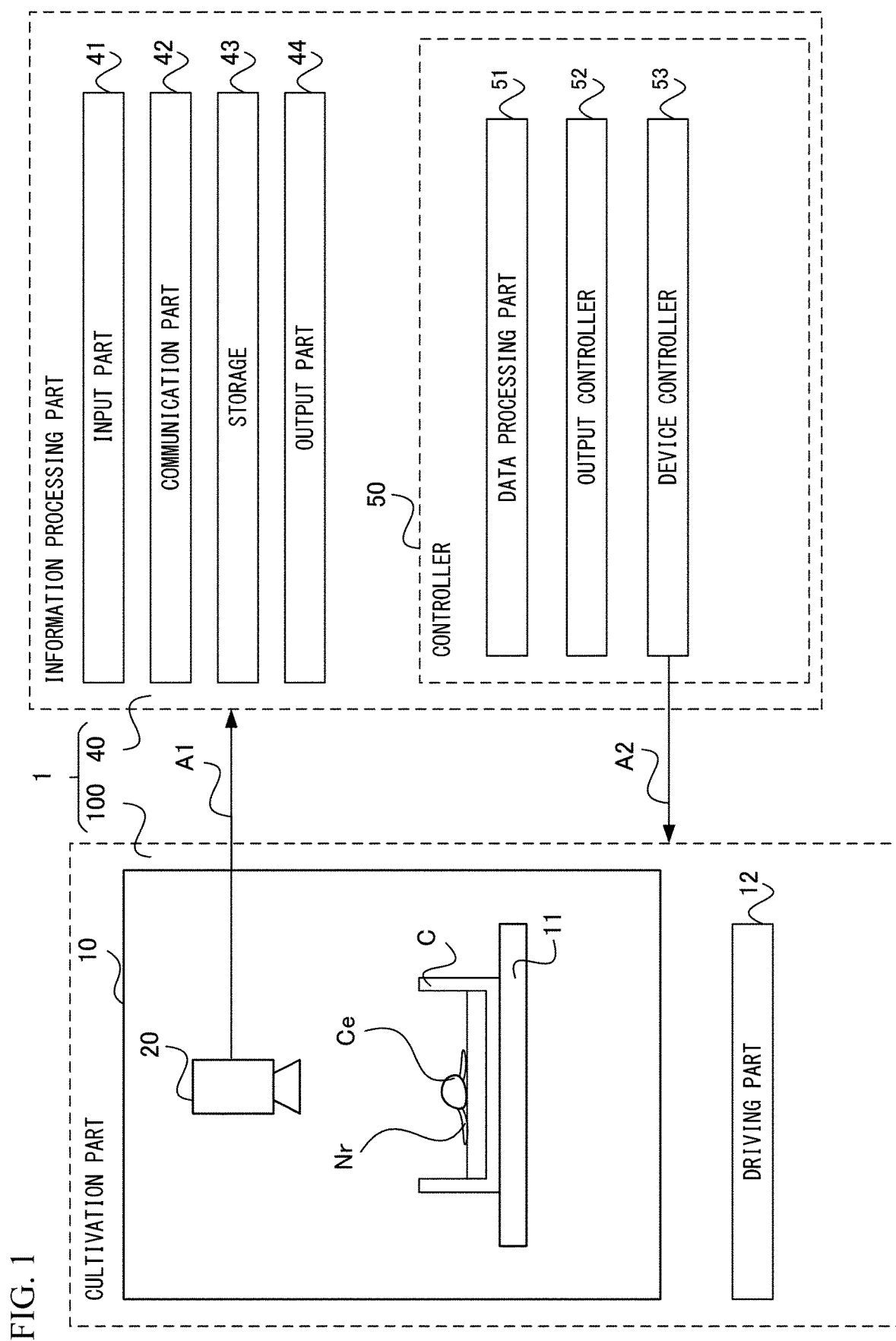
FIG. 1 is a conceptual view showing a configuration of an image processing device of a first embodiment.

FIG. 1 is a conceptual view showing a configuration of an image processing device of an embodiment. An image processing device 1 includes a cultivation part 100, and an information processing part 40. The cultivation part 100 includes a cultivation room (cultivation chamber) 10, a specimen observation table (stage) 11, a driving part 12, and an imaging part 20. The information processing part 40 includes an input part 41, a communication part 42, a storage 43, an output part 44, and a controller 50. The controller 50 includes a data processing part 51, an output controller 52, and a device controller 53.

The image processing device 1 is configured as a cultivation device, and has a configuration in which captured image data that is image data obtained by imaging a sample (for example, a cell) in the cultivation part 100 is input and processed by the data processing part 51.

In the embodiment, a linear portion including a straight line, a curved line, a cross, or the like, is extracted as an extraction target from a captured image corresponding to the captured image data. Hereinafter, while the embodiment will be described using an example in which a cell Ce is a neuron and a portion corresponding to a neurite Nr is extracted, as long as the above-mentioned linear portion is included, the extraction target is not limited to this example and can be an arbitrary element that constitutes an image. Further, extraction may be performed from images other than captured images such as drawn images or the like.

The cultivation part 100 includes the cultivation room 10 in which the cell Ce is cultivated, and performs imaging of the cell Ce cultivated in the cultivation room 10.

The cultivation room 10 accommodates a cultivation container C in which the cell Ce is cultivated. The cultivation container C is, for example, a well plate or a dish. A temperature regulator (for example, a heater) and a temperature sensor, which are not shown, controlled by the controller 50 are disposed in the cultivation room 10, and controlled such that cultivation of a cell is performed under a preset environment, for example, being maintained at a temperature preset by the temperature regulator and the temperature sensor. The driving part 12 includes an actuator, moves the cultivation container C to place it on the specimen observation table 11 inside the cultivation room 10 at a previously determined time. Further, the driving part 12 moves the imaging part 20, the specimen observation table 11, or the like, to an appropriate position (for example, an observation position) such that the cell Ce is disposed on a focal surface of the imaging part 20 for the purpose of imaging of the cell Ce.

The imaging part 20 is provided with an imaging device including an imaging element such as a CMOS, a CCD, or the like, and images the cell Ce, in particular, the neurite Nr of the cell Ce. An imaging method of the imaging part 20 is not particularly limited as long as a pixel corresponding to the neurite Nr can be discriminated from another portion by a luminance value of such pixel or luminance value of a plurality of pixels around such pixel with desired accuracy in the captured image including the cell Ce. For example, the imaging method by the imaging part 20 can use a fluorescence observation method, a phase difference observation method, or the like.

When the imaging part 20 performs the imaging using the fluorescence observation method, fluorescent dyeing can be performed by expressing a fluorescent protein such as GFP or the like in the cell Ce by a gene instruction or expressing a protein in which a protein localized in the neurite Nr and a fluorescent protein are fused. As long as there are no problems in using the cell Ce after imaging (for example, cultivation, transfer, and pickup), another labeling method such as immunostaining or the like may be used.

A pixel signal obtained by imaging the cell Ce using the imaging part 20 is converted into a digital signal, input into the information processing part 40 as the captured image data in which the pixel and the luminance value correspond to each other (an arrow A1 in FIG. 1), and stored in the storage 43.

The information processing part 40 serves as an interface with a user of the image processing device 1 (hereinafter, simply referred to as "a user"), and also performs processing such as communication, storage, computation, or the like, related to various data.

Further, the information processing part 40 may be configured as an information processing device physically separated from the cultivation part 100. In addition, at least some of data used by the image processing device 1 may be stored in a remote server or the like.

The input part 41 includes an input device such as a mouse, a keyboard, various buttons, a touch panel, or the like. The input part 41 receives data or the like required for imaging by the cultivation part 100 or data processing by the data processing part 51 from the user.

The communication part 42 includes a communication device that is able to communicate through connection of the Internet or the like in a wireless or wired manner, and appropriately transmits and receives data related to control or processing in the image processing device 1.

The storage 43 includes a non-volatile storage medium, and stores a program that performs processing in the controller 50, image data related to the processing of the data processing part 51, and the like.

The output part 44 includes a display device such as a liquid crystal monitor or the like, and outputs an image or the like showing information obtained through processing of the data processing part 51.

The controller 50 is constituted by a processing device such as a CPU or the like, functions as a main constituent for an operation of controlling the image processing device 1, and performs various types of processing by executing the program installed in the storage 43.

The data processing part 51 of the controller 50 processes the captured image data input from the imaging part 20, extracts a plurality of pixel groups corresponding to the extraction target, and groups a plurality of pixel groups on the basis of which cell body the plurality of extracted pixel groups are connected to.

Figure 2:
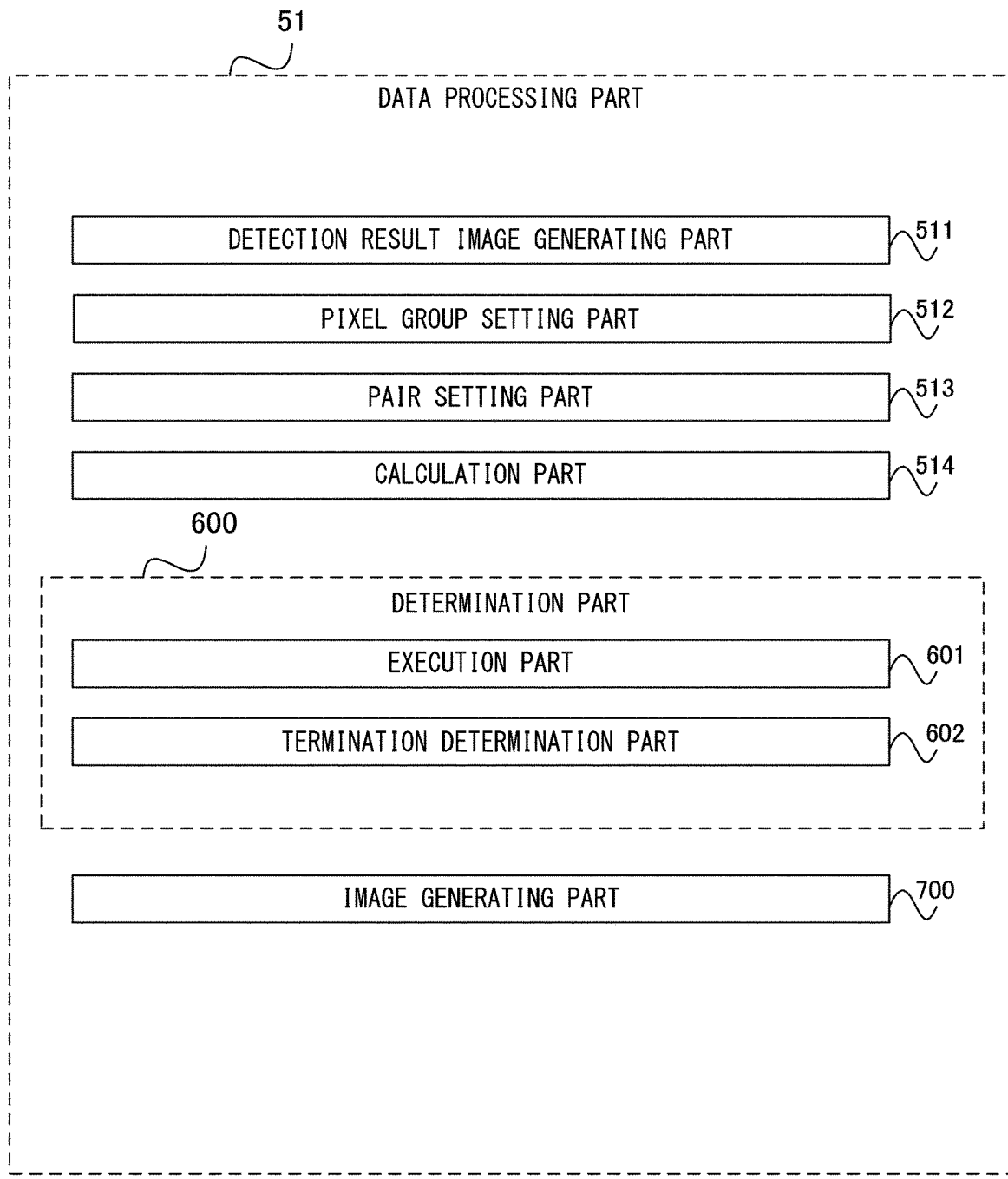
FIG. 2 is a conceptual view showing a configuration of a data processing part according to the first embodiment.

FIG. 2 is a conceptual view showing a configuration of the data processing part 51. The data processing part 51 includes a detection result image generating part 511, a pixel group setting part 512, a pair setting part 513, a calculation part 514, a determination part 600, and an image generating part 700. The determination part 600 includes an execution part 601, and a termination determining part 602.

The detection result image generating part 511 of the data processing part 51 performs image processing on the captured image data stored in the storage 43, and generates and acquires detection result image data corresponding to the detection result image, which will be described below. In the following description, an example in which the detection result image generating part 511 generates probability distribution image data corresponding to the probability distribution image, which will be described in the following, from the captured image data and generates detection result image data from the probability distribution image data will be described. However, there is no limitation to this example, and the detection result image data may be generated from the captured image data without going through the probability distribution image data.

Figure 3:
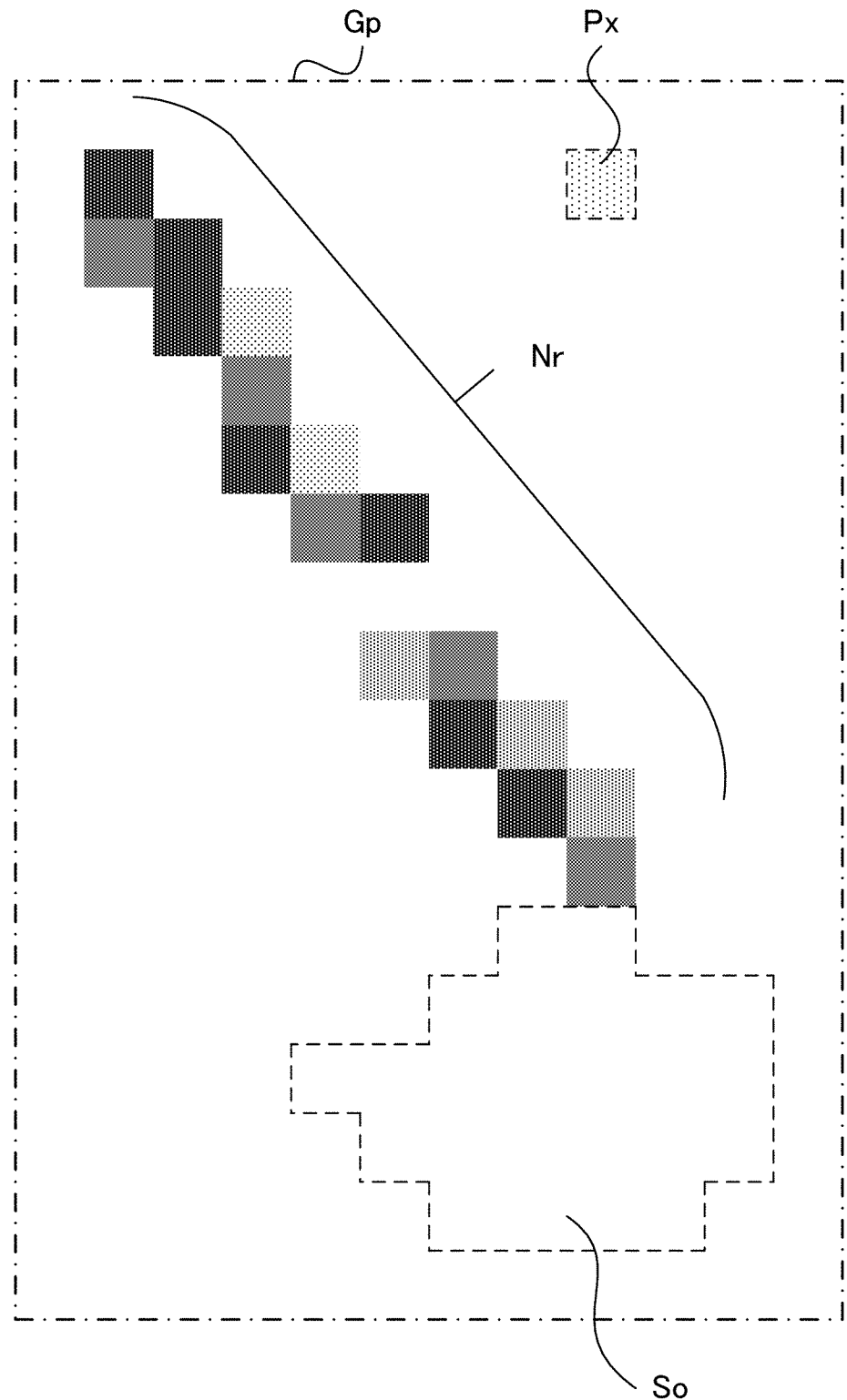
FIG. 3 is a conceptual view showing a probability distribution image according to the first embodiment.

FIG. 3 is a conceptual view showing a probability distribution image Op. In the probability distribution image Gp, in a luminance of each pixel N of the probability distribution image Gp, the pixel Px is associated with a probability corresponding to the neurite Nr of the extraction target. In FIG. 3, while one cell body So and a pixel corresponding to one neurite Nr extending from the cell body So are shown, the probability distribution image Gp preferably includes the image of the plurality of cell bodies So and the plurality of neurites Nr, and the following is also described using this example. In the probability distribution image Gp, with respect to all of the pixels Px in the image, a value of the probability or a value corresponding to the probability are set. Also in the pixels other than the pixels corresponding to the neurite Nr shown in Hg. 3, such a value is set. In actuality, the pixels that do not correspond to the neurite Nr often have a positive value showing the probability and the pixel Px in Hg. 3 shows such an example. In the probability distribution image Gp of FIG. 3, as hatching becomes darker, the pixel Px corresponding to this portion is more likely to be the image portion corresponding to the neurite Nr. In the probability distribution image Gp, while it is preferable that the probability corresponds to each pixel Px as a one-dimensional luminance value and is expressed as a gray scale image, the aspect of the probability distribution image Gp is not particularly limited as long as the probability and the luminance value are associated with each other.

The detection result image generating part 511 calculates the probability with respect to each pixel Px corresponding to the neurite Nr that is the extraction target by performing processing on the captured image data using a predetermined algorithm (hereinafter, referred to as a first algorithm). The first algorithm is machine learning after learning. The machine learning is deep learning in which a plurality of images obtained by imaging neurons and images showing portions corresponding to the neurite in the plurality of images are input into a computation device and learnt. Further, the first algorithm is not particularly limited as long as the probability and the luminance value are associated with each other, and machine learning other than deep learning or an algorithm other than machine learning may be used.

The detection result image generating part 511 generates detection result image data corresponding to the detection result image showing whether each pixel Px corresponds to the nerve Nr by performing the processing with respect to the probability distribution image data using a predetermined algorithm (hereinafter, referred to as a second algorithm).

Figure 4:
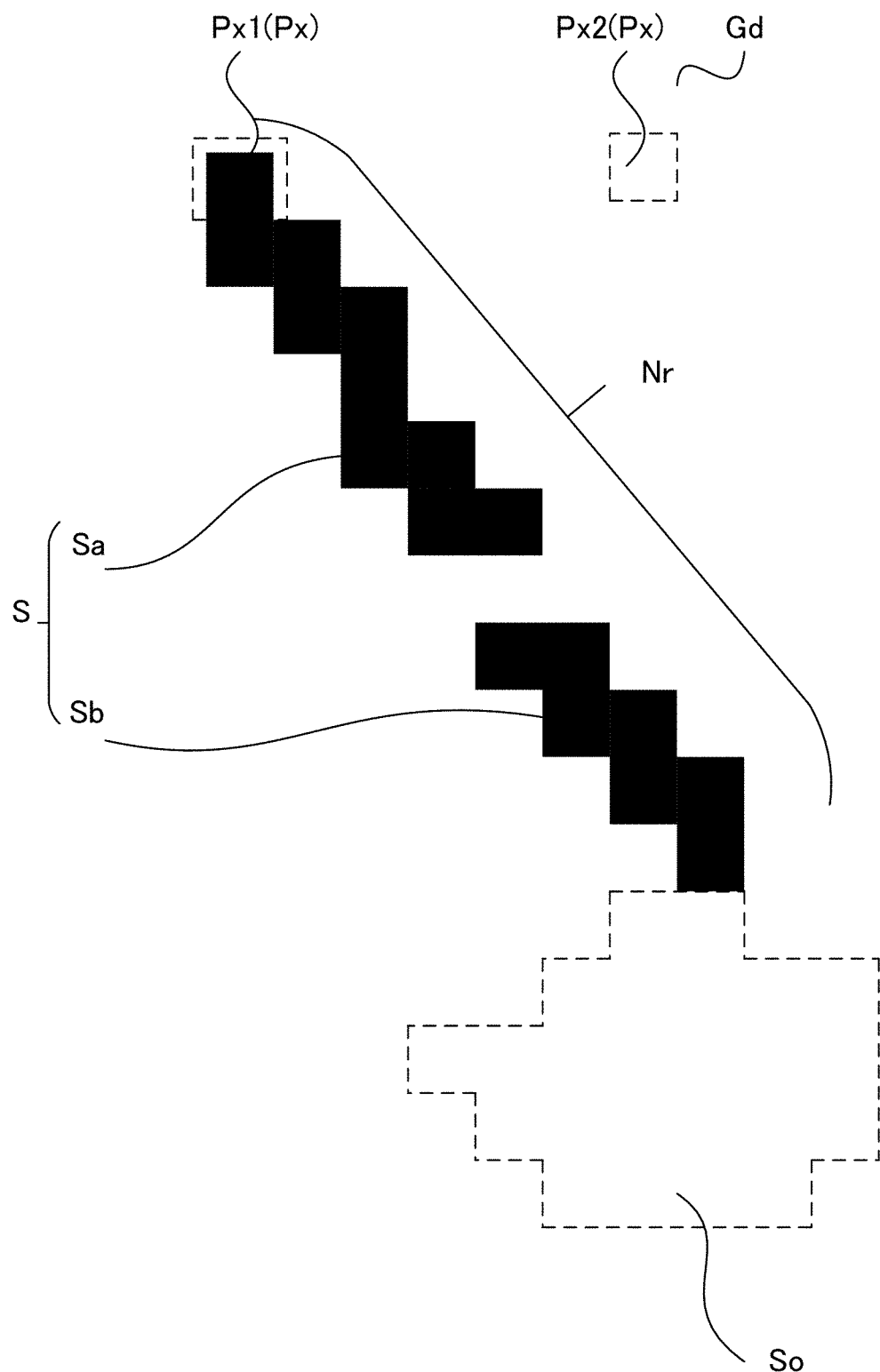
FIG. 4 is a conceptual view showing a detection result image according to the first embodiment.

FIG. 4 is a conceptual view showing a detection result image Gd. The detection result image Gd (for example, a first image) is an image showing whether each pixel Px corresponds to the neurite Nr according to the luminance value. For example, as shown in FIG. 4, by making the detection result image Gd as a binary image, a luminance value corresponding to black in the drawing can indicate that the pixel Px1 corresponds to the neurite Nr and a luminance value corresponding to white in the drawing can indicate that the pixel Px2 does not correspond to the neurite Nr. In addition, in the detection result image Gd, whether each pixel Px corresponds to the cell body So is preferably expressed and determined by image data or the like different from the detection result image data.

Further, as long as the luminance value can indicate whether the pixel Px corresponds to the neurite Nr, the expression method of the detection result image Gd is not particularly limited.

Hereinafter, in the detection result image Gd, a pixel group formed of a plurality of pixel corresponding to the extraction target and connected to each other is referred to as a segment S. In the detection result image Gd of FIG. 4, two segments Sa and Sb corresponding to the one neurite Nr are shown. The segment S preferably has a width that is uniform, but is not limited thereto, and the segment S may be a linear pixel group having an arbitrary width depending on a location (a position of the pixel of the detection result image Gd). Hereinafter, in particular, a line having one pixel as a width as shown in FIG. 4 is appropriately referred to as a fine line. The segment Sa and the segment Sb are more than two pixels apart. In this way, in the detection result image Gd, a portion different from the cell Ce of the subject and corresponding to the neurite Nr is not necessarily connected. One of the reasons for this is that, during imaging, a signal of the pixel corresponding to the linear portion such as the neurite Nr or the like is weak, so that imaging with sufficient accuracy may not be able to be performed. In particular, this tendency is also seen in a fluorescence microscope that is often used for imaging of a cell or the like. In this ease, when it is not determined which the neurite Nr the segment S corresponds to, it is impossible to calculate an exact length, number, or the like, of the neurites Nr when the neurite Nr is analyzed using the detection result image Gd, and it is impossible to appropriately acquire information from the neurite Nr in the acquired image.

When the two pixels or the two segments S are adjacent to each other only in a diagonal direction, whether setting these pixels or the segments S connected or not connected is not particularly limited, and can be appropriately set according to the definition or the like of connectivity in the analysis algorithm when analyzing the above-mentioned neurite Nr.

The second algorithm configured to generate detection result image data is not particularly limited as long as the segment S described later remains in the detection result image Gd, and the following algorithm or the like can be used. For example, the second algorithm includes binarizing the luminance value of the probability distribution image Gp on the basis of the predetermined threshold, setting a pixel having a luminance value equal to or greater than the threshold as a pixel corresponding to the neurite Nr, and setting a pixel having a luminance value less than the threshold as a pixel that does not correspond to the neurite Nr. Alternatively, the second algorithm may include processing such as frame extraction or the like with respect to the segment S. The detection result image generating part 511 can perform frame extraction processing with respect to each segment S using, for example, a method shown in a document ("Simultaneously Identifying All True Vessels from Segmented Retinal Images" IEEE TRANSACTIONS ON BIOMEDICAL ENGINEERING, Vol. 60, No. 7, July 2013) of Lau.

The detection result image generating part 511 acquires the detection result image data, and then, stores the detection result image data that can be referred from the CPU in a memory, the storage 43, or the like, connected to the CPU of the controller 50 (hereinafter, disclosed as "stored in the storage 43 or the like").

Further, the image processing device 1 may not have a configuration in which the image processing device 1 performs imaging or cultivation as long as the detection result image data can be obtained. The data processing part 51 may acquire the detection result image data from the communication part 42 or the like, and store the detection result image so that it can be referred to in the memory, the storage 43, or the like.

The pixel group setting part 512 sets and acquires the plurality of segments S (for example, the first pixel group and the second pixel group), which are not connected to each other, from the plurality of pixels Px that constitute the detection result image Gd. In the at least two segments S set by the pixel group setting part 512, the segments S that are not connected to each other and that will not be connected via another pixel group such as the following trigeminal, cross, or the like, in the detection result image Gd are included. The pixel group setting part 512 performs processing of detecting a trigeminal or a cross and removing the trigeminal or the cross from the detection result image Gd, and then sets the plurality of segments S. Here, the cross refers to a branch to which four or more linear pixel groups are connected.

Figure 5:
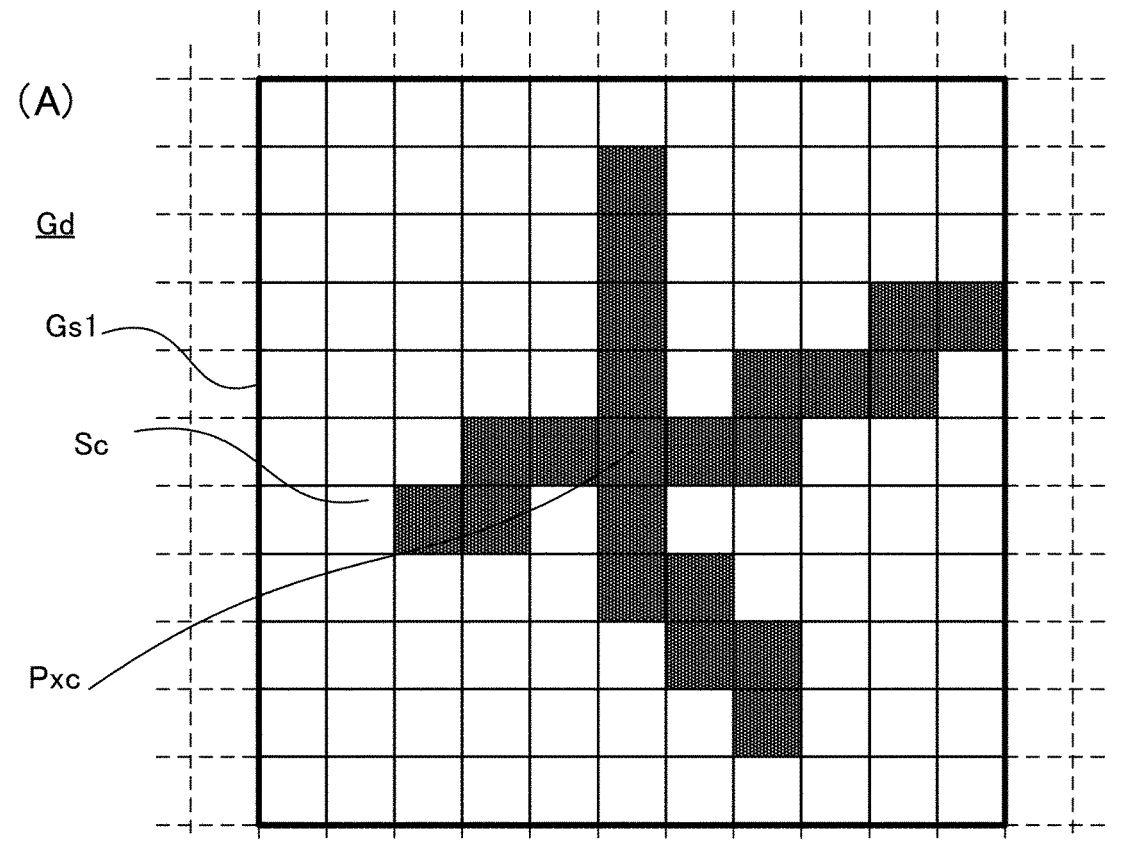
FIG. 5A is a conceptual view for describing detection of a cross according to the first embodiment.
FIG. 5B is a conceptual view for describing detection of a cross according to the first embodiment.
Figure 5:
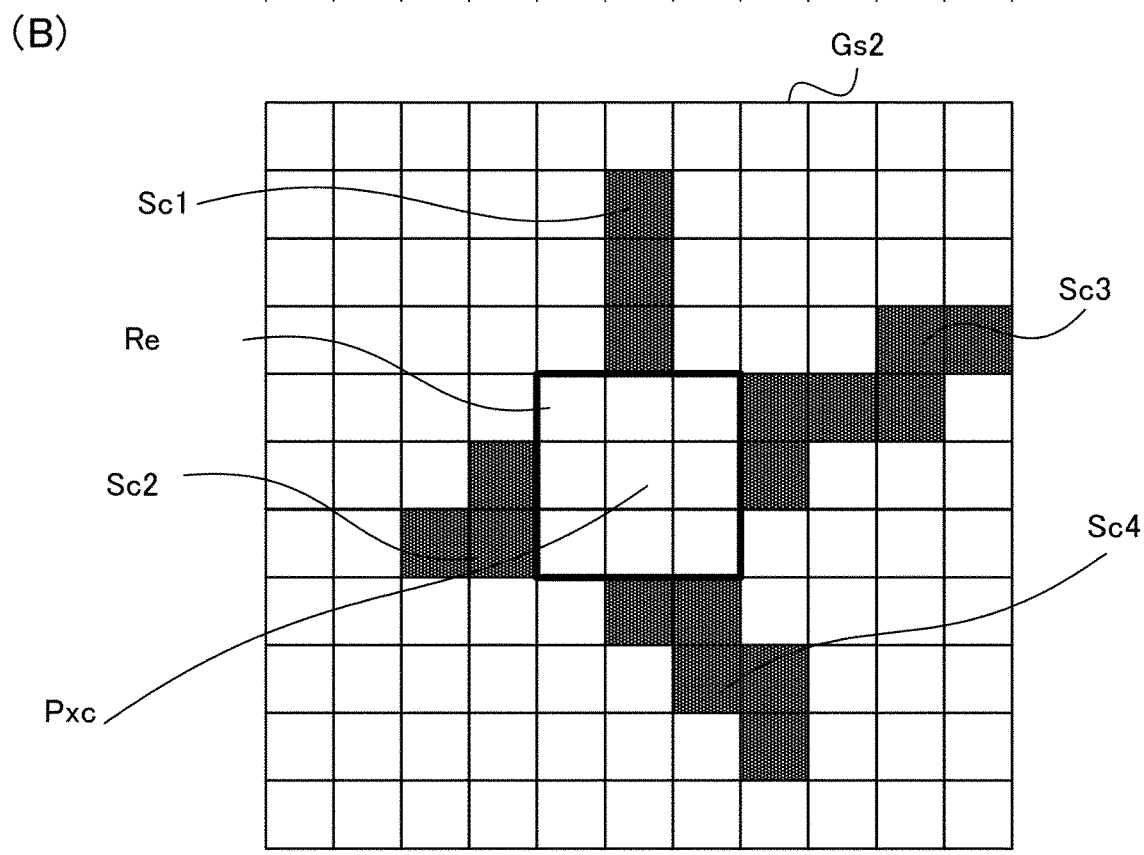

FIG. 5A and FIG. 5B are conceptual view for describing processing of detecting and removing the cross in the plurality of pixel groups. The pixel group setting part 512 generates data corresponding to a first partial image Gs1 that is an image of a portion of the detection result image Gd. The first partial image Gs1 is an image corresponding to a square-shaped pixel region, one side of which has 2N+1 pixels (n is a natural number) using a center pixel Pxc as a center. While a value of N is 5 in FIG. 5A, the value is appropriately set based on characteristics of the object, a width of the segment S in the detection result image Gd, an average value of the width or length, or the like.

The pixel group setting part 512 generates data that a pixel region corresponding to a circle of a radius M using the center pixel Pxc as a center does not correspond to the neurite Nr, in other words, data that a pixel region corresponding to a circle of a radius M using the center pixel Pxc as a center corresponds to the second partial image Gs2 which is a pixel not included in the segment S, from the first partial image Gs1. The pixel region corresponding to the circle of the radius M is referred to as a removed pixel region Re. M is a positive number smaller than N. The removed pixel region Re is a 3×3 square pixel region constituted by pixels including at least a part of the circle of the radius M, where M is 1 in FIG. 5B. Here, if the trigeminal or the cross is included in the portion of the first partial image Gs1 corresponding to the removed pixel region Re, the segment Sc becomes the plurality of segments S in the second partial image Gs2 by removing the trigeminal or the cross. Accordingly, the number of the segments S is higher in the second partial image Gs2 than in the second partial image Gs1. In FIG. 5B, the segment Sc is separated into the plurality of segments Sc1, Sc2, Sc3 and Sc4 by the removed pixel region Re.

The pixel group setting part 512 replaces a portion of the first partial image Gs1 of the detection result image Gd with the second partial image Gs2 while assuming that the cross is detected in the removed pixel region Re when a difference obtained by subtracting the number of the segments S in the second partial image Gs2 from the number of the segments S in the first partial image Gs2 is two or more. The pixel group setting part 512 repeats equally moving the center pixel Pxc by one pixel at a time appropriately in the detection result image Gd, sequentially generating the first partial image Gs1 and the second partial image Gs2, and replacing a portion of the first partial image Gs1 of the detection result image Gd with the second partial image Gs2 when the cross is detected. The pixel group setting part 512 stores data corresponding to the obtained detection result image Gd in the storage 43 or the like when the entire detection result image Gd has been covered by the first partial image Gs1 or the second partial image Gs2 that is generated so far.

Further, as long as the trigeminal or the cross can be removed, the size, the shape, and the like, of the first partial image Gs1, the second partial image Gs2 and the removed pixel region Re are not particularly limited.

The pixel group setting part 512 generates data, which indicates each segment S includes which pixel Px, on the basis of the luminance value of each pixel in the detection result image Gd after the trigeminal or the cross has removed. For example, the pixel group setting part 512 groups the plurality of pixels px1 included in the segment S in a group for the pixels that are connected to each other. The pixel group setting part 512 stores the generated data in the storage 43 or the like.

Among the plurality of segments S set by the pixel group setting part 512, the pair setting part 513 sets a pair of a certain segment S and a segment S including a certain pixel within a search range R from the segment S. At least a pair of the segments S that are not connected to each other is included in the pair that is set by the pair setting part 513, and further, the pair is also not connected via another pixel group of the trigeminal, the cross, or the like, in the detection result image Gd before the trigeminal, the cross, or the like, is removed. Among the plurality of segments S set by the pixel group setting part 512, the segment S in which the search range R which will be described, is set is referred to as a first segment (the segment that serves as a reference of the set search range R), and the other segment is referred to as a second segment (the segment that is not a reference of the set search range R).

Figure 6:
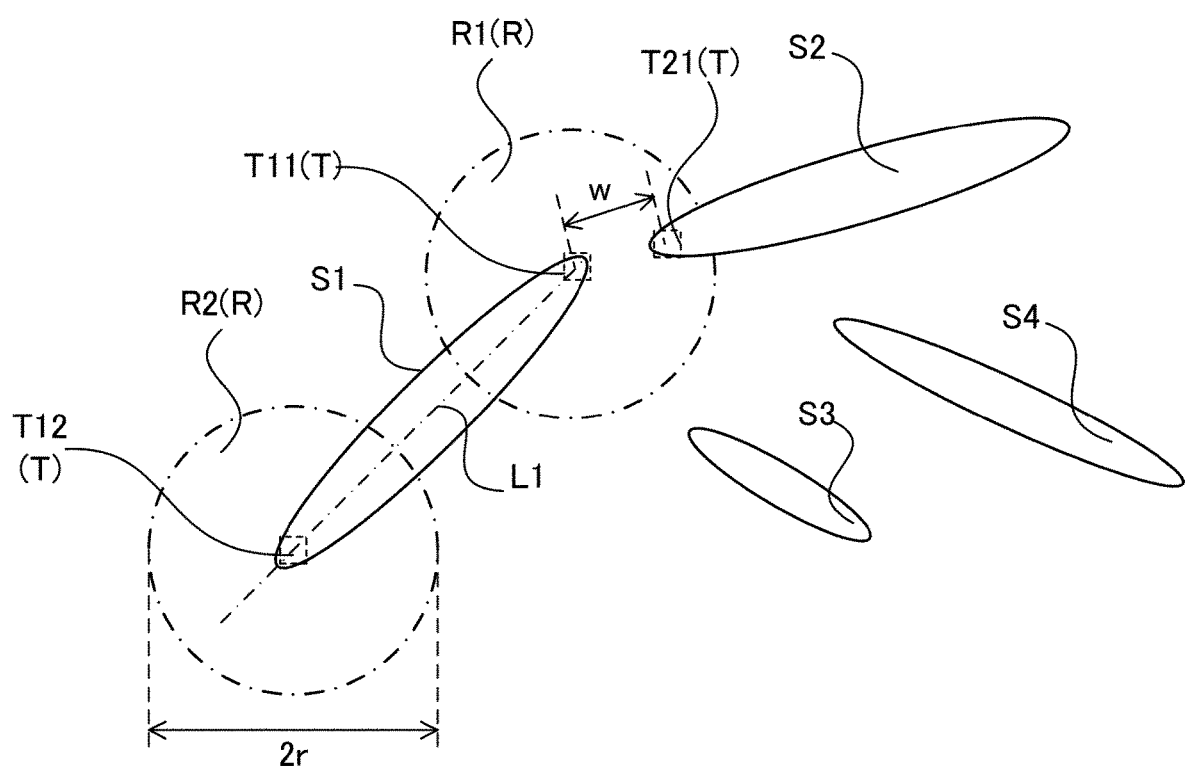
FIG. 6 is a conceptual view for describing a search range according to the first embodiment.

FIG. 6 is a conceptual view for describing setting of the pair. The pair setting part 513 extracts pixels located at both ends of the segment S included in the detection result image Gd. Hereinafter, pixels located at both ends of the segment S are referred to as end pixels T. The pair setting part 513 sets pixels located at both ends of the fine line corresponding to each segment S as the end pixels T, respectively, when the segment S is the fine line. The pair setting part 513 can set, for example, pixels or the like close to both ends along a curved line or a line segment corresponding to the segment S as the end pixels T when the segment S is not the fine line. In FIG. 6, pixels located at both ends of a first segment S1 are set as the end pixels T11 and T12.

The pair setting part 513 sets regions within a predetermined range (pixel regions), which have the end pixels T11 and T12 as centers, respectively, as the search ranges R1 and R2 of the first segment S1. A shape of the search range R is not particularly limited, and for example, may be a pixel region corresponding to a circle, a rectangle, or the like. When the search range R is the pixel region corresponding to the circle, while a radius of the circle may be, for example, about a half of an average such as an arithmetic mean or the like of lengths of the segments S included in the detection result image Gd, but it is not particularly limited.

The pair setting part 513 detects end pixels T of second segments (in an example of FIG. 6, second segments S2, S3 and S4) included in the search range R of the segment S1. In FIG. 6, the end pixels T21 of the second segment S2 included in the search range R1 are detected. The pair setting part 513 sets a set of the first segment S1 and the second segment S2 as a segment pair that becomes a target, a connecting degree of which is calculated. Meanwhile, since the second segments S3 and S4 do not have pixels included in the search range R, a pair of the first segment S1 and the second segment S3 and a pair of the first segment S1 and the second segment S4 are not set as a segment pair.

As shown in FIG. 6, when the search range R is referred to as the pixel region corresponding to the circle, a distance w (a first distance) between the first segment S1 and the second segment S2 that are set as a pair is smaller than a radius r of the search range R. Accordingly, the pair setting part 513 sets a segment pair on the basis of the distance of the segments S (for example, a distance between the two end pixels T).

The pair setting part 513 performs setting of the segment pair with respect to each segment S that constitutes the plurality of segments S set by the pixel group setting part 512. In the example of FIG. 6, the pair setting part 513 sets the search ranges R on the end pixels T and detects the end pixels T of the other segment S in the search range R, respectively, for each of the segments S2, S3 and S4. The pair setting part 513 sets segment pairs of the segments S2, S3 and S4 and the segment S including the detected end pixels T, respectively. The pair setting part 513 does not need to set the overlapping segment pairs when it overlaps the already set segment pair. Accordingly, the calculation part 514 does not perform the following calculation processing of the connecting degree for the pair that is not detected on the basis of the search range R because the segment pair is set by the pair setting part 513. The pair setting part 513 stores the segment pair that was set in the storage 43 or the like.

The calculation part 514 calculates a connecting degree between the two segments S included in the segment pair. Hereinafter, the two segments included in the segment pair are referred to as the first segment S1 and the second segment S2 and described. In other words, the calculation part 514 calculates a connecting degree of the second segment S2 with respect to the first segment S1. Here, the connecting degree indicates probability that the two segments S correspond to the same linear portion of the object, in other words, the same neurite Nr, and includes the ease of connection on the basis of the shape and disposition of the two segments S. The connecting degree is expressed by a numerical value or the like, and may be expressed by a sign or the like as long as the connecting degrees can be compared with each other. The calculation part 514 stores the calculated connecting degree in the storage 43 or the like. In addition, as described above, for example, the calculation part 514 does not perform the calculation processing of the connecting degree when there is no segment pair set by the pair setting part 513.

Figure 7:
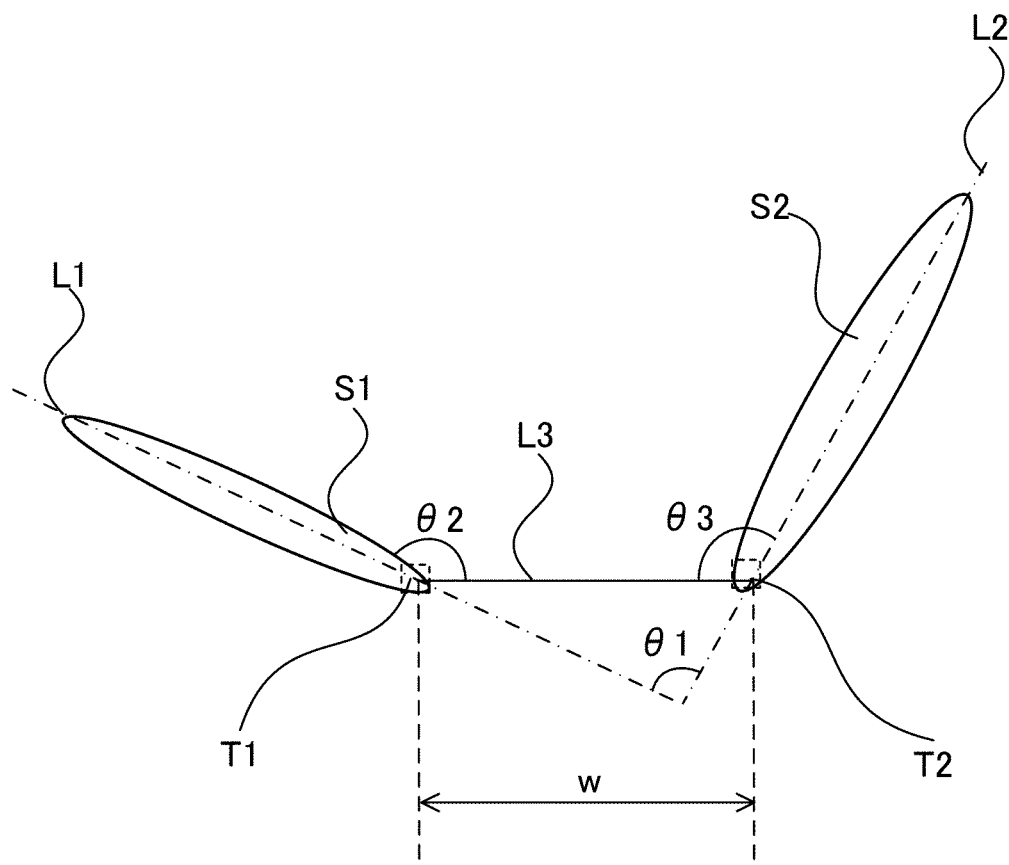
FIG. 7 is a conceptual view for describing calculation of a connecting degree according to the first embodiment.

Next, FIG. 7 is a conceptual view for describing calculation of a connecting degree. The calculation part 514 sets a first line segment L1 corresponding to the first segment S1 and a second line segment L2 corresponding to the second segment S2. The calculation part 514 sets, for example, the line segment when the line segment passes through the largest number of pixels included in the first segment S1 in a case in which the end pixels T1 of the first segment S1 are fixed and an inclination of the line segment passing through the end pixels T1 is changed as the first line segment L1. In this way, the first segment S1 corresponding to the first pixel group has the first line segment L1. Similarly, the calculation part 514 can set the line segment when the line segment passes through the largest number of pixels included in the second segment S2 in a case in which the end pixels T2 of the second segment S2 are fixed and an inclination of the line segment passing through the end pixels T2 is changed as the second line segment L2. Alternatively, the calculation part 514 may set a line segment that connects pixels of both ends of the first segment S1 as the first line segment L1, and set a line segment that connects pixels of both ends of the second segment S2 as the second line segment L2. In this way, the second segment S2 corresponding to the second pixel group has the second line segment L2.

The calculation part 514 sets a third line segment L3 that is a line segment that connects the end pixels T1 of the first segment S1 and the end pixels T2 of the second segment S2. The calculation part 514 calculates a length of the third line segment L3 that is a distance between the end pixels T1 and the end pixels T2. Hereinafter, the length is referred to as the distance w between the segments, which is a distance between the first segment S1 and the second segment S2.

Further, the first line segment L1 does not have to pass through the end pixels T1, and for example, depending on the shape of the first segment S1, in some cases, passing through pixels closer to a center of gravity of the first segment S1 than the end pixels T1 further reflects the shape of the first segment S1. Accordingly, the first line segment L1 can be set to pass through the appropriate two pixels included in the first segment S1 as appropriate. The second line segment L2 is also the same as described above. A line segment passing through the first line segment L1 corresponding to the first segment S1 and the second line segment L2 corresponding to the second segment S2 obtained in this way may be referred to as the third line segment L3. In addition, similarly, depending on the shapes or the like of the first segment S1 and the second segment S2, the third line segment L3 may be a line segment that connects an arbitrary point included in the first segment S1 and an arbitrary point included in the second segment S2 as appropriate.

Next, the calculation part 514 calculates a first angle $\theta 1$ that is an angle formed between the first line segment L1 and the second line segment L2. The calculation part 514 calculates a second angle $\theta 2$ that is an angle formed between the first line segment L1 and the third line segment L3. The calculation part 514 calculates a third angle $\theta 3$ that is an angle formed between the second line segment L2 and the third line segment L3. These angles can be calculated using inclinations or the like of the first line segment L1, the second line segment L2 and the third line segment L3.

The calculation part 514 calculates a connecting degree DC of the second segment S2 with respect to the first segment S1 using the following Equation (1). Hereinafter, "*" indicates a product.

$$DC = c0 * |w| + c1 * \sin\theta 2 + c2 * \sin\theta 3 + c3 * (1 + \cos\theta 1) \quad (1)$$

Here, c0, c1, c2 and c3 are positive integers and set as appropriate on the basis of characteristics of the extraction target.

Further, Equation (1) is set such that the connecting degree DC becomes the weight of the edge and the connecting degree becomes positive when an optimization technology such as a Prim's algorithm or the like is used during the grouping described in the following. However, the connecting degree DC can be appropriately set according to the algorithm during the grouping described in the following when at least one of the above mentioned distance w between the segments, the first angle $\theta 1$, the second angle $\theta 2$ and the third angle $\theta 3$ is used. In a non-limiting example, the connecting degree DC may be only the first term (the distance w between the segments) or the fourth term (the first angle $\theta 1$) on a right-hand side of Equation (1), may be only the first term and the fourth term, may be only the first term, the second term (the second angle $\theta 2$) and the third term (the third angle $\theta 3$), may be only the first term, the second term and the fourth term, may be only the first term, the third term and the fourth term, and may be only the second term, the third term and the fourth term.

The determination part 600 determines grouping of the plurality of segments S set by the pixel group setting part 512 on the basis of the connecting degree calculated by the calculation part 514. In the grouping, the segment S corresponding to the neurite Nr extending from the same cell body So is set to belong to the same group. Here, it is possible that all the segments S belong to one group, and some of the segments S do not belong to any group corresponding to each cell body So that was determined in advance.

The algorithm of the grouping by the determination part 600 is not particularly limited as long as the calculated connecting degree is used. Hereinafter, an example in which grouping is performed by obtaining a minimum spanning tree of a weighted connection graph in which each segment S is set as a node and the connecting degree is set as the weight of the edge that connecting the nodes using a Prim's algorithm will be described.

Further, the minimum spanning tree may be obtained using a Kruskal's algorithm or a Boruvka's algorithm.

The execution part 601 of the determination part 600 executes the algorithm of the grouping and obtains a minimum spanning tree. The execution part 601 generates data corresponding to the weighted connection graph using each segment S as a node and using a connecting degree between the two segments S of the segment pair as the weight of the edge between the two nodes corresponding to the two segments S.

Figure 8:
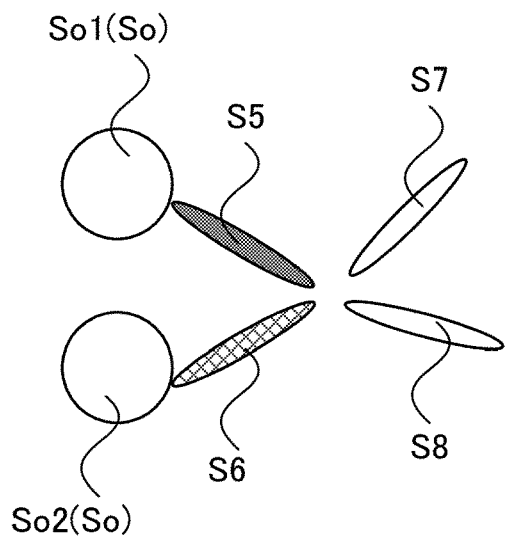
FIG. 8A is a conceptual view for describing a grouping method according to the first embodiment.
FIG. 8B is a connection graph corresponding to FIG. 8A.
Figure 8:
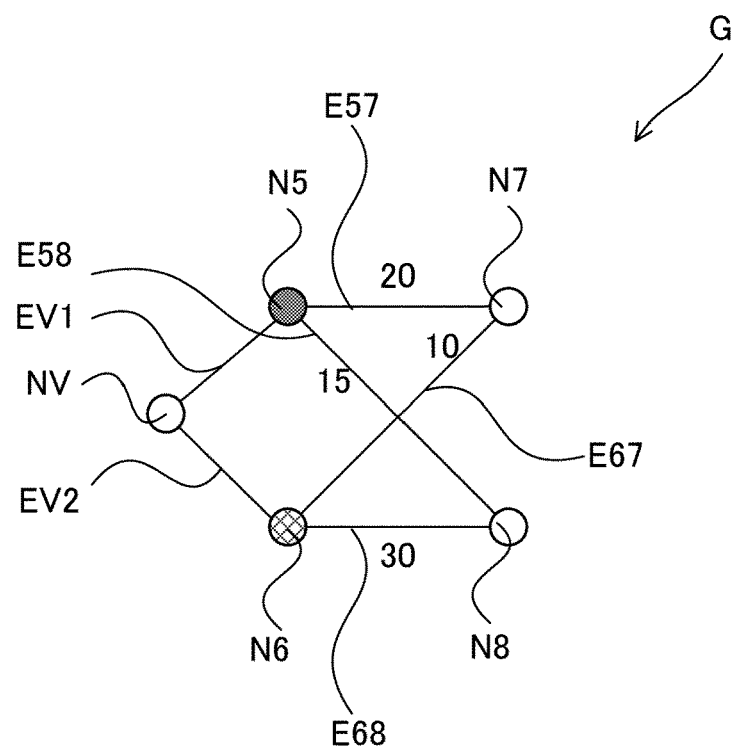

FIG. 8A is a conceptual view for describing an initial stage of grouping, and FIG. 8B is a weighted connection graph G corresponding to FIG. 8A. A weighted connection graph disclosed in the following drawings is exemplary, and the present invention is not limited. The segment S5 is connected to the cell body So1. The segment S6 is connected to the cell body So2. In the execution part 601, nodes N5 and N6 corresponding to the segments S5 and S6 connected to each cell body So are set as root nodes, and the segment S other than the segment S corresponding to the root node is set as a node. The execution part 601 sets the edge between the extracted nodes.

In FIG. 8B, the nodes N5 and N6 and nodes N7 and N8 corresponding to the segments S5, S6, S7 and S8 are set. Each of the segment S5 and the segment S7, the segment S5 and the segment S8, the segment S6 and the segment S7, and the segment S6 and the segment S8 is a segment pair, and edges E57, E58, E67 and E68 are set using the connecting degree as a weight. In the example of FIG. 8B, the weight of the edge E57 is set to 20, the weight of the edge E58 is set to 15, the weight of the edge 67 is set to 10, and the weight of edge 68 is set to 30. A virtual node NV is a node that is virtually set such that the entire graph becomes one concatenated graph. A virtual edge EV1 is set between the virtual node NV and the root node N5, and a virtual edge EV2 is set between the virtual node NV and the root node N6.

In the execution part 601, a root node is set as a determination node, and a node other than the root node is set as a non-determination node. The nodes N5 and N6 corresponding to the segment S5 and S6 and the segment S5 and S6 belong to different groups since they correspond to the segments which are connected to different cell bodies So, and are shown by different hatchings. The nodes N7 and N8 corresponding to the segment S7 and S8 are non-determination nodes.

Among the edges that connect the determination node and the non-determination node, the execution part 601 repeats setting the non-determination node connected to an edge having the smallest weight as the determination node. In the stages of FIGS. 8A and 8(B), the execution part 601 selects the edge E67 having the smallest weight among the edges E57, E58, E67 and E68 that connect a determination node N5 or N6 and a non-determination node N7 or N8, and sets the non-determination node N7 connected to the edge E67 as the determination node.

Figure 9:
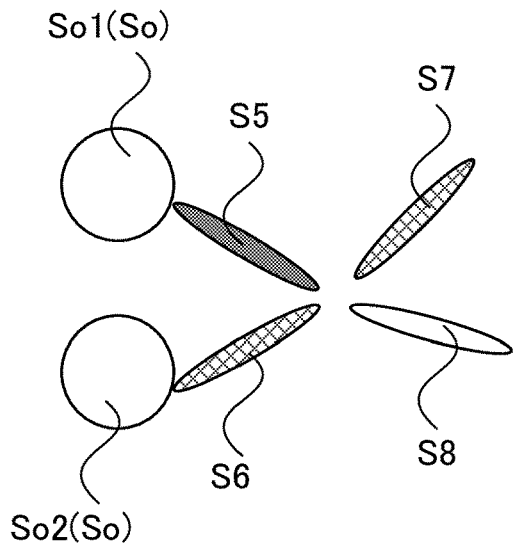
FIG. 9A is a conceptual view for describing the grouping method according to the first embodiment.
FIG. 9B is a connection graph corresponding to FIG. 9A.
Figure 9:
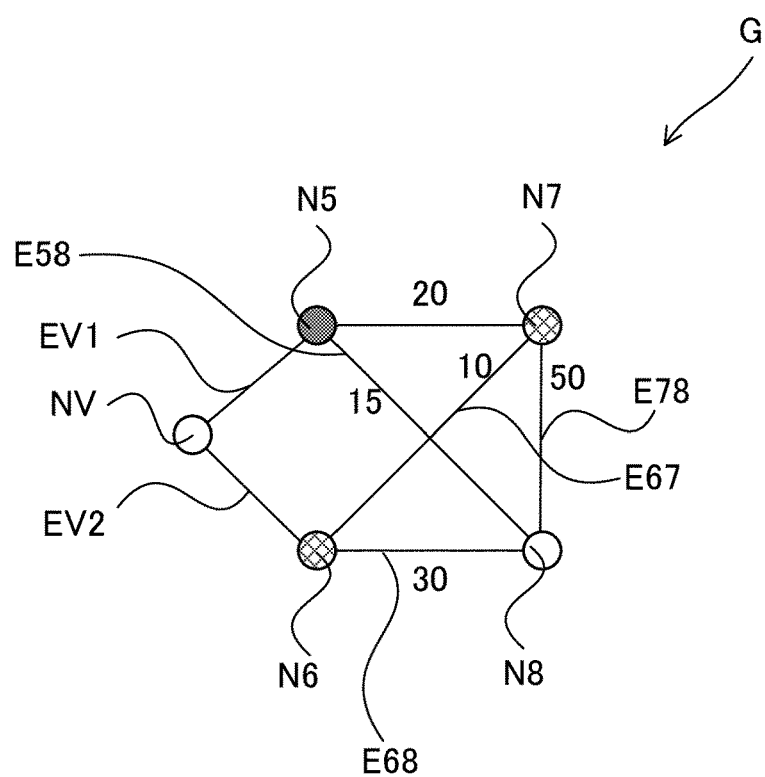

FIG. 9A is a conceptual view for describing a state after the node N7 is set to the determination node, and FIG. 9B is the weighted connection graph C corresponding to FIG.

9A. After the node N7 is set as the determination node, the weighted connection graph G including an edge E78 between the node N7 and the node N8 is created. In the example of FIG. 9B, the weight of the edge E78 is 50. In this way, whenever the determination node is set, a weighted connection graph including an edge that connect a determination node and a non-determination node that are newly set is created. In the execution part 601, the determination node N6 and the determination node N7 connected to the selected edge E67 are set to belong to the same group. In FIGS. 9A and 9B, the same hatching shows that the segments S6 and S7 corresponding to the determination nodes N6 and N7 and the determination nodes N6 and N7 belong to the same group. Next, the execution part 601 selects the edge E58 having the smallest weight from the edges E58, E68 and E78 that connect the determination nodes N5 and N6 or N7 and the non-determination node N8, and sets the non-determination node N8 connected to the edge E58 as the determination node.

Figure 10:
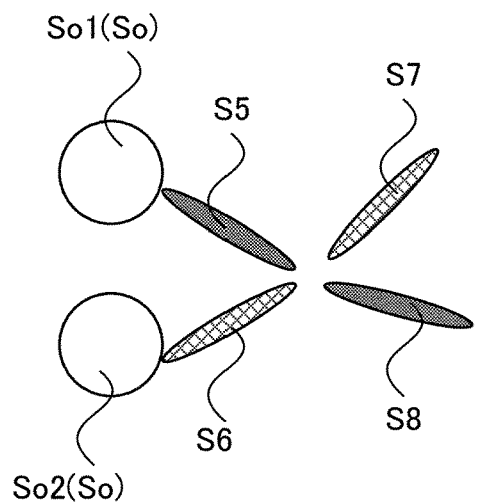
FIG. 10A is a conceptual view for describing the grouping method according to the first embodiment.
FIG. 10B is a connection graph corresponding to FIG. 10A.
FIG. 10C is a weighted connection graph after grouping.
Figure 10:
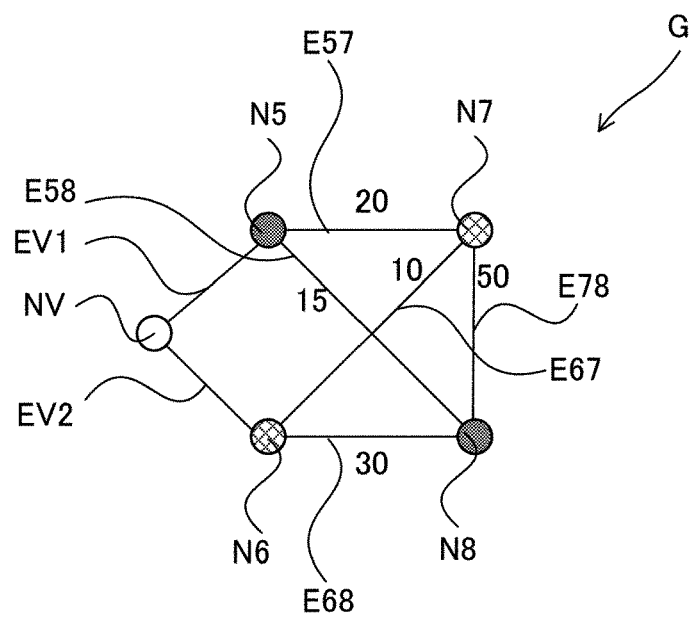
Figure 10:
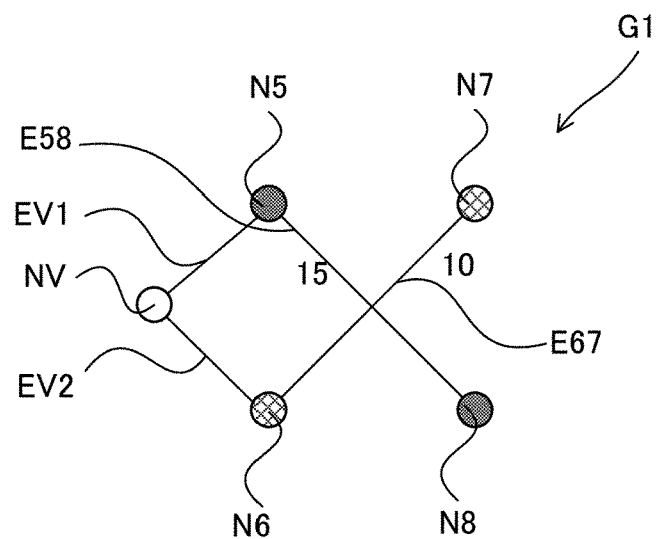

FIG. 10A is a conceptual view for describing a stage after the node N8 is set as the determination node, and FIG. 10B is the weighted connection graph G corresponding to FIG. 10A. The execution part 601 is set such that the determination node N5 and the determination node N8 connected to the selected edge E58 belong to the same group. In FIG. 10A and FIG. 10B, the same hatching shows that the segments S5 and S8 corresponding to the determination nodes N5 and N8 and the determination nodes N5 and N8 belong to the same group.

In FIG. 10C, when the non-determination node in not left in the weighted connection graph G, the execution part 601 sets the weighted connection graph G1 including the edges E58 and E67, the determination node and the virtual node NV selected in searching for the edge so far as a minimum spanning tree. The weighted connection graph G1 can be regarded as a connection because the virtual node NV that integrates the plurality of root nodes N5 and N6 is set. In addition, the execution part. 601 generates grouping data that is data indicating a result of the grouping of the segments S from the data corresponding to the weighted connection graph G1. The execution part 601 stores the grouping data in the storage 43 or the like. The detection result image Gd is appropriately provided for morphological analysis or the like by the data processing part 51 or the like on the basis of the grouping data, and calculation of the like of the neurite length is performed.

Referring to FIG. 2, the termination determining part 602 of the determination part 600 calculates a sum of the weight of the edges selected by the execution part 601 (hereinafter, referred to as a determination parameter), and terminates processing of obtaining the minimum spanning tree by the execution part 601 when the determination parameter is equal to or greater than predetermined threshold (hereinafter, referred to as a determination threshold). The determination threshold can be appropriately set on the basis of an average value of connecting degrees that are weights of the edges, characteristics of the object, the number of the segments S included in the detection result image Gd, or the like. Accordingly, it is possible to minimize grouping of the segments S that does not need grouping, such as the segment S that is too far from the other segment S, the segment in which the cell body So to be connected does not exist in the detection result image Gd, or the like.

The image generating part 700 generates image data (hereinafter, referred to as output image data) corresponding to the output image that is an image showing a result of grouping of the segments S in the detection result image Gd. The aspect of the output image is not particularly limited, and the result of the grouping by the image or the character obtained through image processing of the detection result image Gd can be shown. When the output image obtained through image processing of the detection result image Gd is generated, the segment S can be shown separately for each group. For example, in the output image, the segment S can have at least one of the color phase, brightness and chroma that are different for each group, and for example, the luminance value such as RGB or the like can be different for each group.

Referring to FIG. 1, the output controller 52 of the controller 50 controls the output part 44 and outputs an output image.

The device controller 53 of the controller 50 controls the respective parts of the cultivation part 100 on the basis of the input or the like from the input part 41 (an arrow A2). The device controller 53 executes control related to the cell cultivation (for example, control of the cultivation room 10 that manages a temperature or a humidity, control of the driving part 12), or causes the imaging part 20 to execute imaging.

Figure 11:
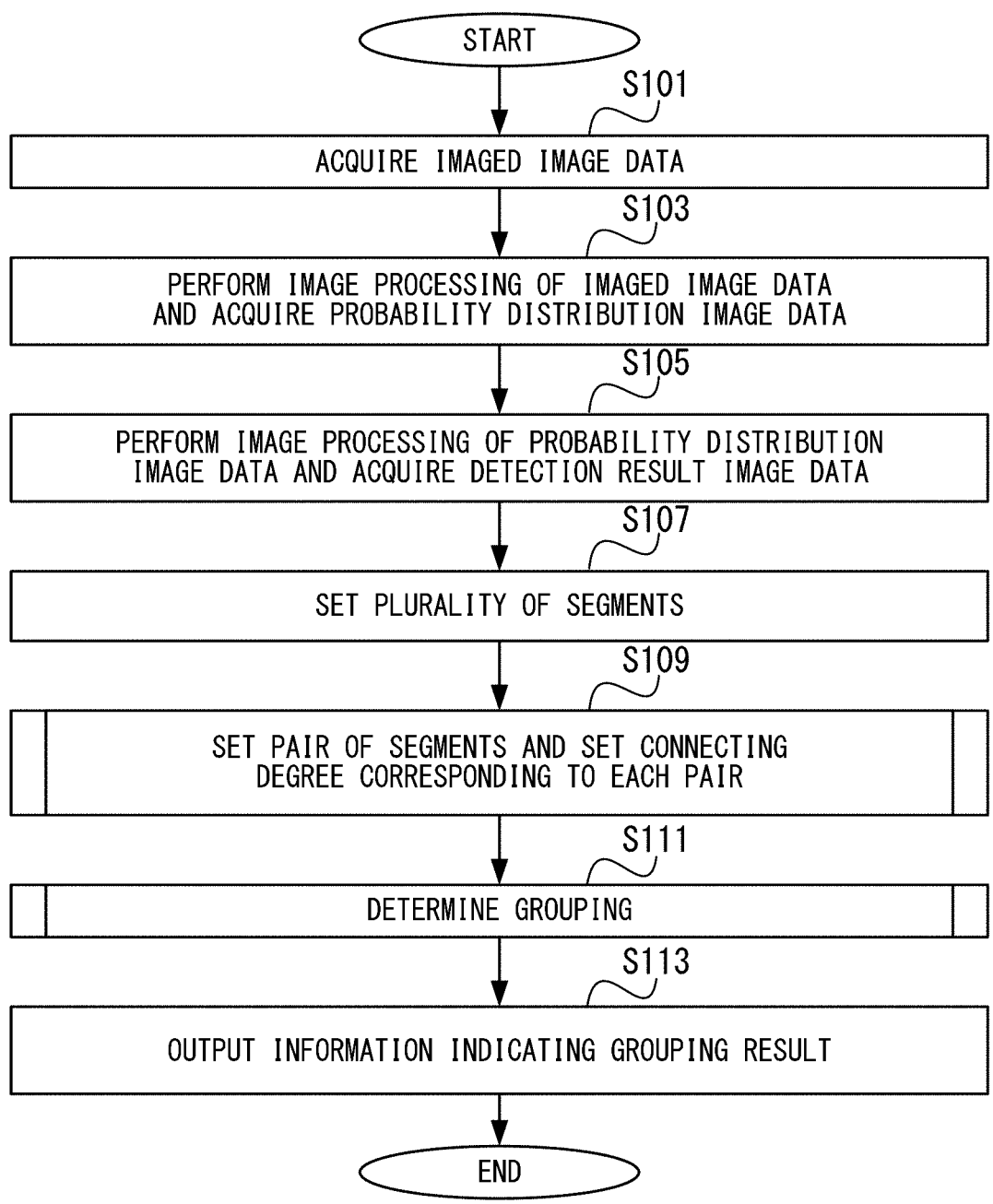
FIG. 11 is a flowchart showing a flow of an image processing method according to the first embodiment.

FIG. 11 is a flowchart showing a flow of an image processing method according to the embodiment. In step S101, the detection result image generating part 511 acquires the captured image data obtained by imaging of the imaging part 20. After step S101 is terminated, step S103 is started. In step S103, the detection result image generating part 511 performs image processing of the captured image data and acquires probability distribution image data. After step S103 is terminated, step S105 is started.

In step S105, the detection result image generating part 511 performs image processing of the probability distribution image data, and acquires detection result image data. After step S105 is terminated, step S107 is started. In step S107, the pixel group setting part 512 sets the plurality of segments S. After step S107 is terminated, step S109 is started.

In step S109, the pair setting part 513 sets a pair (a segment pair), and sets a connecting degree corresponding to each pair. After step S109 is terminated, step S111 is started. In step S111, the determination part 600 determines the grouping of the segments S. After step S111 is terminated, step S113 is started. In step S113, the output controller 52 outputs information indicating a result of the grouping. For example, the output controller 52 outputs information such as a label or the like constituted by names, numbers or signs indicating the segment belonging to the same group, or an output image representing the segment belonging to the same group with the same luminance value or the like. After step S113 is terminated, processing is terminated.

Figure 12:
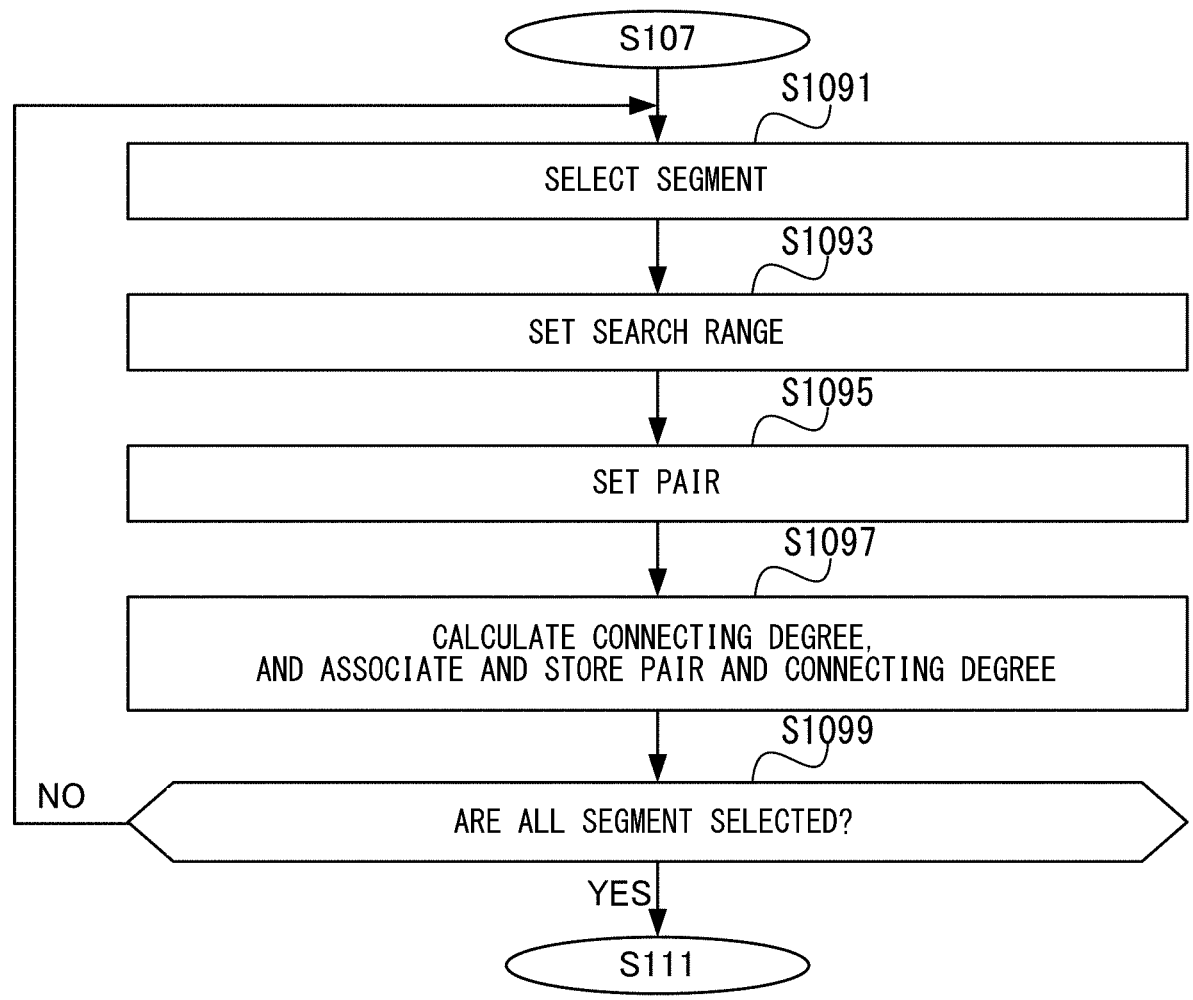
FIG. 12 is a flowchart showing a flow of the image processing method according to the first embodiment.

FIG. 12 is a flowchart showing a flow of step S109 in the flowchart of FIG. 11. After step S107 is terminated, step S1091 is started. In step S1091, the pair setting part 513 selects the segment S. After step S1091 is terminated, step S1093 is started. In step S1093, the pair setting part 513 sets the search range R in the selected segment S. After step S1093 is terminated, step S1095 is started.

In step S1095, the pair setting part 513 sets a pair of the selected segment S and the segment S including pixels included in the search range R of the selected segment S. After step S1095 is terminated, step S1097 is started. In step S1097, the calculation part 514 calculates the connecting degree, associates the pair and the connecting degree, and stores it in the storage 43 or the like. After step S1097 is terminated, step S1099 is started.

In step S1099, the pair setting part 513 determines whether all the segments S of the detection result image Gd are selected. The pair setting part 513 makes a positive determination of step S1099 when all the segments S are selected, and step S111 is started. The pair setting part 513 makes a negative determination of step S1099 and step S1091 is started when there is the segment S that is not selected.

Figure 13:
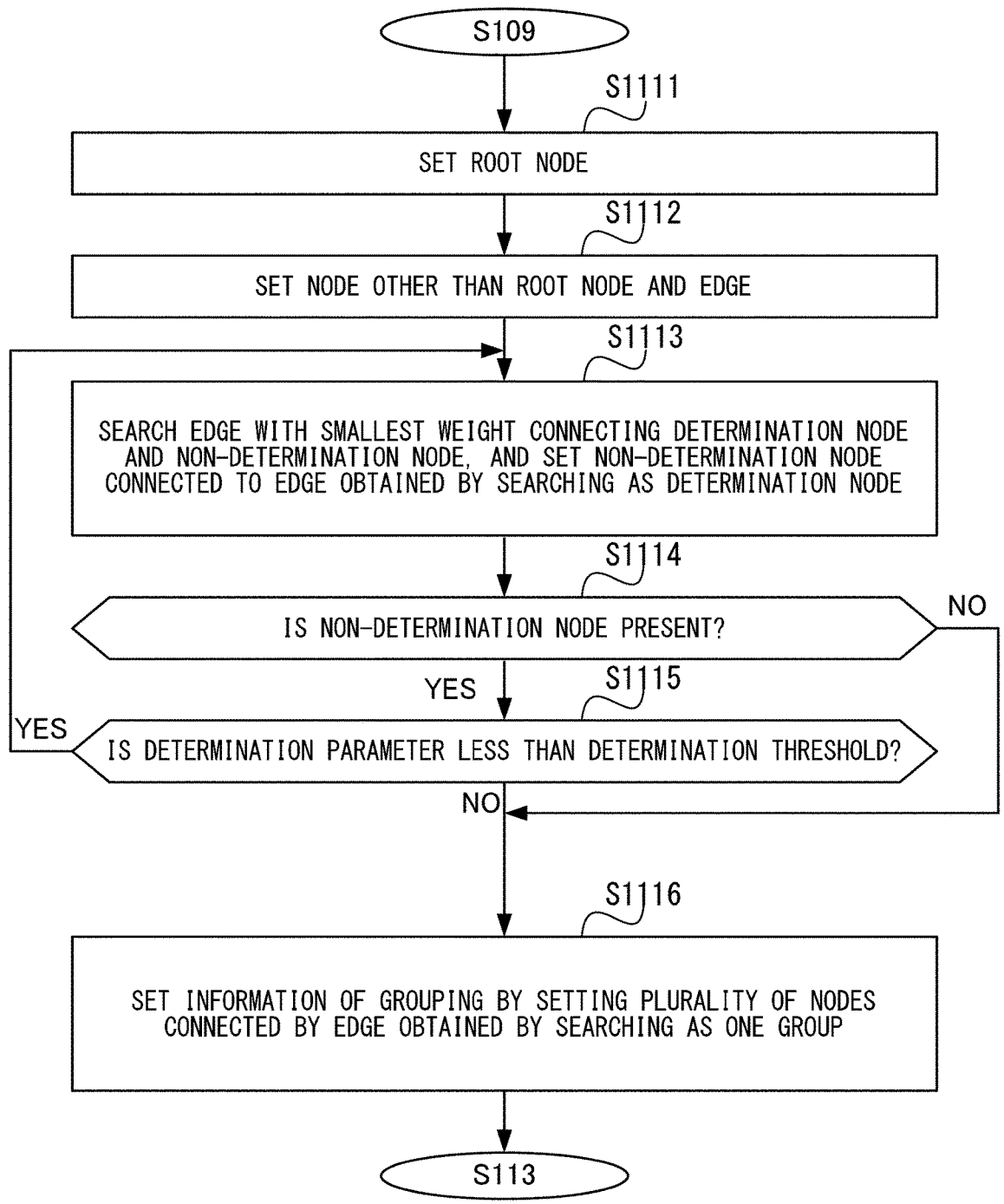
FIG. 13 is a flowchart showing a flow of the image processing method according to the first embodiment.

FIG. 13 is a flowchart showing a flow of step S111 in the flowchart of FIG. 11. After step S109 is terminated, step S1111 is started. In step S1111, the execution part 601 sets the root node as the determination node. When step S1111 is terminated, step S1112 is started. In step S1112, the execution part 601 sets a node other than the root node and an edge. When step S1112 is terminated, step S1113 is started.

In step S1113, the execution part 601 searches an edge connecting a determination node and a non-determination node and having a smallest weight, and sets the non-determination node connected to the edge obtained through searching as the determination node. After step S1113 is terminated, step S1114 is started. In step S1114, the execution part 601 determines whether the non-determination node is present. The execution part 601 makes a positive determination in step S1114 when the non-determination node is present, and step S1115 is started. The execution part 601 makes a negative determination in step S1114 when the non-determination node is not present, and step S1116 is started.

In step S1115, the termination determining part 602 determines whether the determination parameter is less than the determination threshold. The termination determining part 602 makes a positive determination in step S1115 when the determination parameter is less than the determination threshold, and step S1113 is started. The termination determining part 602 makes a negative determination in step S1114 when the determination parameter is equal to or greater than the determination threshold, step S1116 is started. In step S1116, the execution part 601 sets information of the grouping using a plurality of nodes connected to each other by the edge obtained through searching as one group. After step S1116 is terminated, step S113 is started.

According to the above-mentioned embodiment, the following effects are obtained.

(1) The image processing device 1 of the embodiment includes the pixel group setting part 512 configured to acquire the plurality of segments S including the first segment S1 and the second segments S2, S3 and S4, which are not connected to each other, from the plurality of pixels Px that constitute the detection result image Gd, and the pair setting part 513 configured to set a pair of the first segment S1 and the second segment S2, which includes the pixels in the search range R of the first segment S1, among the plurality of segments S in order to set the connecting degree with respect to the first segment S1. Accordingly, the image processing device 1 can accurately analyze how the extracted pixel group such as the segment S or the like corresponds to the linear portion, also including the broken pixel segment.

(2) The image processing device 1 of the embodiment includes the calculation part 514 configured to calculate the distance w between the segments between the first segment S1 and the second segment S2 or the first angle θ1, and the calculation part 514 calculates the connecting degree using the distance w between the segments or the first angle θ1. Accordingly, the image processing device 1 can accurately analyze how the pixel groups correspond to the linear portion on the basis of the positional relation of the two pixel groups.

(3) In the image processing device 1 of the embodiment, the calculation part 514 can calculate at least one angle of the second angle θ2 formed between the third line segment L3, which passes through the point included in the first segment S1 and the point included in the second segment S2, and the first line segment L1 and the third angle θ3 formed between the third line segment L3 and the second line segment L2, and calculate the connecting degree on the basis of at least one of the second angle θ2 and the third angle θ3. Accordingly, the image processing device 1 can more accurately analyze how the pixel groups correspond to the linear portion on the basis of a more specific positional relation of the two pixel groups.

(4) In the image processing device 1 of the embodiment, the calculation part 514 can calculate at least one of the angle formed between the shortest line segment of the third line segment L3 and the first line segment L1 and the angle formed between the above mentioned line segment and the second line segment L2, and calculate the connecting degree on the basis of the above mentioned at least one angle. Accordingly, the image processing device 1 can more accurately analyze how the pixel groups correspond to the linear portion on the basis of the more specific positional relation of the two pixel groups.

(5) In the image processing device 1 of the embodiment, the pair setting part 513 performs setting of the pair with respect to each of the segments S that constitutes the plurality of segments S, and the calculation part 514 is configured to calculate the connecting degree of each pair and includes the determination part 600 configured to determine grouping of the plurality of segments S on the basis of the calculated connecting degree. Accordingly, the image processing device 1 can accurately analyze how the extracted pixel group corresponds to the linear portion throughout the entire image, also including the broken pixel segment.

(6) In the image processing device 1 of the embodiment, the determination part 600 sequentially determines which group the node belongs to on the basis of the minimum spanning tree obtained by the Prim's algorithm, the Kruskal's algorithm or the Boruvka's algorithm using each of the plurality of segments S as nodes and the connecting degrees as the weights of the edges. Accordingly, the image processing device 1 can efficiently perform optimal grouping of the pixel groups.

(7) In the image processing device 1 of the embodiment, the determination part 600 includes the termination determining part 602 configured to determine whether the processing of obtaining the minimum spanning tree is terminated on the basis of the sum of the numerical value corresponding to the plurality of selected edges when the edges are selected by the Prim's algorithm, the Kruskal's algorithm or the Boruvka's algorithm. Accordingly, the image processing device 1 can prevent the pixel group that does not require the grouping from being grouped.

(8) The image processing device 1 of the embodiment includes the image generating part 700 configured to generate an output image showing a result of the grouping. Accordingly, the image processing device 1 can provide information how the extracted pixel group corresponds to the linear portion.

(9) In the image processing device 1 of the embodiment, the pixel group setting part 512 removes the pixel corresponding to the trigeminal or the cross from the pixels that constitute the detection result image Gd and sets the removed pixel as the pixel that is not included in the plurality of segments S before the plurality of segments S are acquired. Accordingly, the image processing device 1 can accurately analyze how the extracted pixel group corresponds to the linear portion, even in the image including the trigeminal or the cross, also including the broken pixel segment.

(10) In the image processing device 1 of the embodiment, the detection result image Gd is an image obtained by performing image processing on the image obtained by imaging the object, and is a binary image showing whether each pixel corresponds to the linear structure using a pixel value with respect to the pixels of the detection result image Gd, and the pixel group setting part 512 acquires the plurality of segments S on the basis of the pixel value. Accordingly, the image processing device 1 can accurately analyze how the pixel group extracted from the captured image corresponds to the linear portion of the subject, also including the broken pixel segment.

(11) In the image processing device 1 of the embodiment, the detection result image Gd is the image showing the plurality of pixels Px1 corresponding to the neurite Nr, and the connecting degree is the numerical value indicating probability that the first segment S1 and the second segment S2 correspond to a part of the neurite extending from the same neuron. Accordingly, the image processing device 1 can accurately analyze how the pixel group extracted from the captured image corresponds to the neurite Nr, also including the broken pixel segment.

(12) The image processing device 1 of the embodiment includes the pixel group setting part 512 configured to acquire the first segment S1 and the second segment S2 from the detection result image Gd, the calculation part 514 configured to calculate the second angle θ2 formed between the first line segment L1 and the third line segment L3 passing through the first segment S1 and the second segment S2, and the determination part 600 configured to determine whether the first segment S1 and the second segment S2 correspond to a connected linear region on the basis of the second angle θ2. Accordingly, the image processing device 1 can accurately analyze how the extracted pixel group corresponds to the linear portion on the basis of the positional relation between the first segment S1 and the second segment S2. In addition, the image processing device 1 can accurately perform the grouping using the second angle θ2 even when the fine line that constitutes the first segment S1 and the second segment S2 is parallelly shifted, when one fine line is extremely short, when the segment with the first segment S1 and the second segment S2 curved is present, or the like.

(13) In the image processing device 1 of the embodiment, the calculation part 514 calculates the third angle θ3 formed between the third line segment L3 and the second line segment l2, and the determination part 600 determines whether the first segment S1 and the second segment S2 correspond to the connected linear region on the basis of the second angle θ2 and the third angle θ3. Accordingly, the image processing device 1 can accurately analyze how the extracted pixel group corresponds to the linear portion on the basis of the more specific positional relation of the two segments S.

(14) In the image processing device 1 of the embodiment, the determination part 600 can determine whether the first segment S1 and the second segment S2 correspond to the connected linear region on the basis of the first angle θ1, which is an angle formed between the first line segment L1 corresponding to the first segment S1 and the second line segment L2 corresponding to the second segment S2, and the second angle θ2. Accordingly, the image processing device 1 can accurately analyze how the extracted pixel group corresponds to the linear portion on the basis of the more specific positional relation of the two segments S.

(15) In the image processing device 1 of the embodiment, the determination part 600 can determine whether the first segment S1 and the second segment S2 correspond to the connected linear region on the basis of the first angle θ1. Accordingly, the image processing device 1 can accurately analyze how the extracted pixel group corresponds to the linear portion on the basis of the direction in which the two segments S are arranged.

(16) In the image processing device 1 of the embodiment, the determination part. 600 can determine whether the first segment S1 and the second segment S2 correspond to the connected linear region on the basis of the first angle θ1, the second angle θ2 and the third angle θ3. Accordingly, the image processing device 1 can accurately analyze how the extracted pixel group corresponds to the linear portion on the basis of the more specific positional relation of the two segments S.

(17) The imaging device according to the embodiment includes the image processing device 1 and the imaging part 20. Accordingly, the imaging device can accurately analyze how the pixel group extracted from the captured image corresponds to the linear portion, also including the broken pixel segment.

(18) The image processing device 1 that is the cultivation device according to the embodiment includes the cultivation part 100 configured to cultivate a cell. Accordingly, the cultivation device can accurately analyze how the pixel group extracted from the image of the cultivated cell corresponds to the linear portion, also including the broken pixel segment.

(19) The image processing method according to the embodiment includes acquiring the plurality of segments S including the first segment S1 and the second segments S2, S3 and S4, which are not connected to each other, from the plurality of pixels Px that constitute the detection result image Gd, and setting a pair of the first segment S1 and the second segment S2, which includes the pixels in the search range R of the first segment S1, among the plurality of segments S in order to set the connecting degree with respect to the first segment S1. Accordingly, the image processing method can accurately analyze how the extracted pixel group corresponds to the linear portion, also including the broken pixel segment.

(20) The image processing method according to the embodiment includes acquiring the first segment S1 and the second segment S2 from the detection result image Gd, calculating the second angle θ2 formed between the first line segment L1 and the third line segment L3, which passes through the point included in the first segment S1 and the point included in the second segment S2, and determining whether the first segment S1 and the second segment S2 correspond to the connected linear region on the basis of the second angle θ2. Accordingly, the image processing method can accurately analyze how the extracted pixel group corresponds to the linear portion on the basis of the positional relation of the two segments S.

The following modifications are also within the scope of the present invention and can be combined with the above-mentioned embodiment.

(Variant 1)

In the above-mentioned embodiment, the pixel group setting part 512 may set a pixel group constituted by a plurality of pixel segments, which are not connected to each other, from the plurality of pixels Px included in the detection result image Gd, as one segment S.

Figure 14:
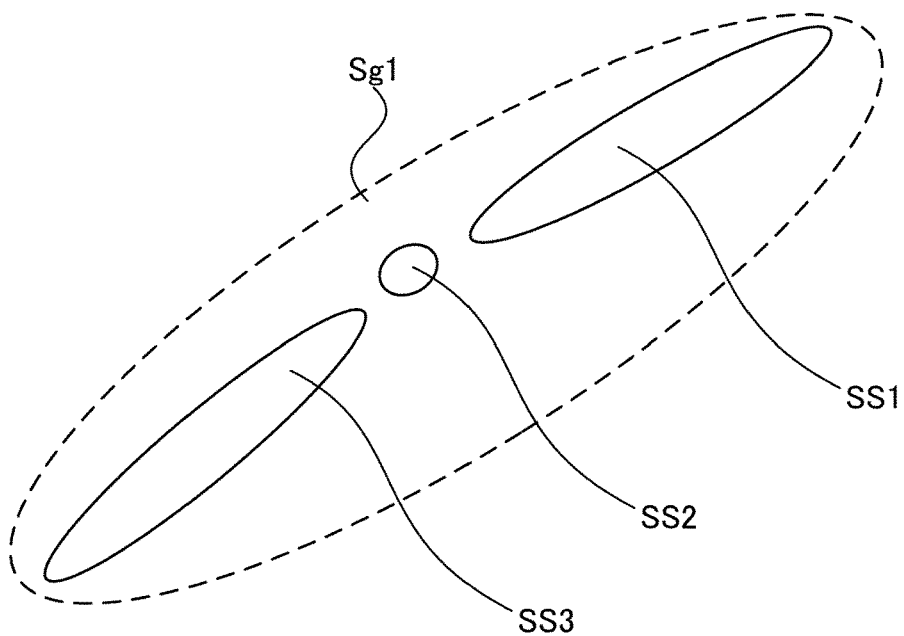
FIG. 14A is a conceptual view for describing setting of a pixel group according to Variant 1.
FIG. 14B is a conceptual view for describing setting of a pixel group according to Variant 1.
Figure 14:
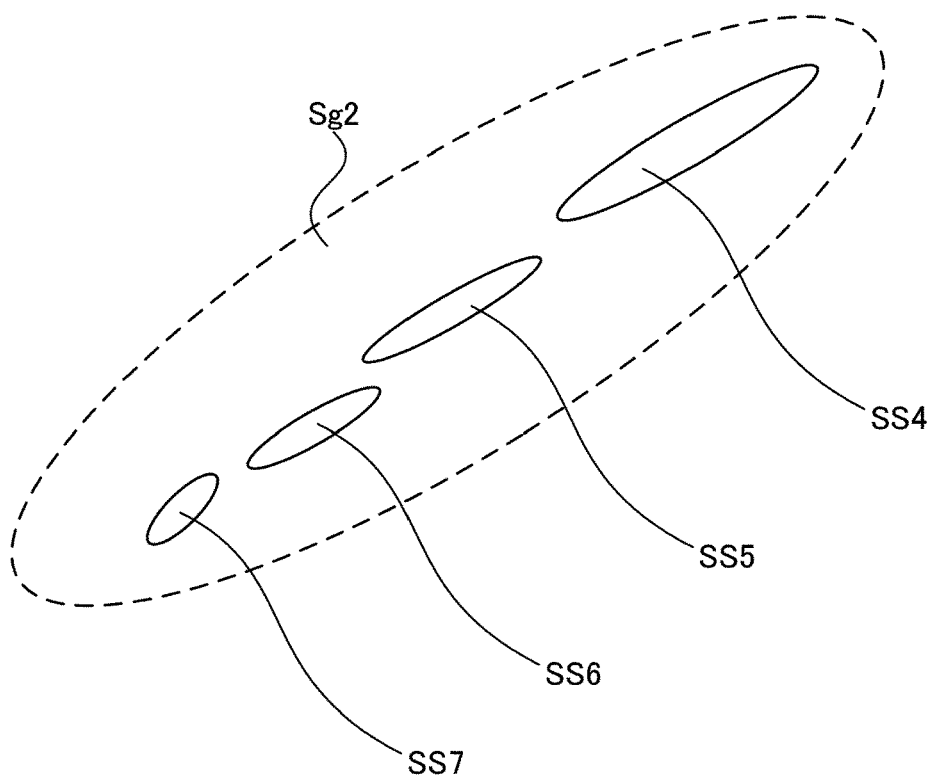

FIG. 14A and FIG. 14B are views showing an example of a pixel group (for example, a plurality of pixel group) constituted by a plurality of pixel segments. A pixel group Sg1 of FIG. 14A includes a pixel segment SS1, a pixel segment SS2 and a pixel segment SS3. The pixel segment SS2 corresponds to, for example, a circular pixel where it is difficult to assign fine lines. When the pixel segments SS1, SS2 and SS3 are linearly arranged even though such a pixel segment SS2 is present, the pixel group setting part 512 can set them as one pixel group Sg1. For example, when the pixel segments are present within a predetermined distance and the pixel segment SS2 is present at a distance shorter than the predetermined distance from the line segment corresponding to the pixel segment SS1 or SS3, the pixel segment SS2 can be set as the pixel segment that constitutes the pixel group Sg1. The predetermined distance can be set in advance so that the pixels constituting the pixel group Sg1 are linearly arranged.

A pixel group Sg2 of FIG. 14B includes pixel segments SS4, SS5, SS6 and SS7. Even when the pixel segments are arranged in this way, for example, when the pixel segments are within the predetermined distance and each of the pixel segments SS4 to SS7 is present within the predetermined distance from the line segment corresponding to at least one of the pixel segments SS4 to SS7, the pixel group setting part 512 can set them as the pixel segments that constitutes the pixel group Sg2.

The data processing part 51 can perform the processing using the pixel group Sg1 or Sg2 constituted by the plurality of pixel segments as one segment S. For example, the calculation part 514 can set the pixels on both ends of the pixel group Sg1 as the end pixels T1 and T2 of the above-mentioned embodiment, and can set the first line segment L1, the second line segment l2, the first angle θ1, the second angle θ2, the third angle θ3 and the distance w between the segments according to definition of the above-mentioned embodiment. Accordingly, even when at least a part of the segment S in the above-mentioned embodiment is used as the pixel group including the plurality of pixel segments, similarly, processing such as setting, grouping, or the like, of the pair can be performed.

In the image processing device of the variant, the pixel group setting part 512 acquires the pixel group constituted by the plurality of pixels Px1 that are connected to each other, or the pixel group Sg1 or Sg1 constituted by the plurality of pixel groups SS1 to SS3 or SS4 to SS7 that are not connected to each other, as the pixel group that constitutes the plurality of segments S from the plurality of pixels Px that constitute the detection result image Gd. Accordingly, when the detection result image Gd includes many pixel segments constituted by few pixels, it is possible to efficiently analyze how the extracted pixel group corresponds to the linear portion.

(Variant 2)

The pair setting part 513 may set the search range R using a method different from the above-mentioned embodiment. In the following Variants 2-1 and 2-2, the longitudinal and lateral lengths of the search range can be an average such as an arithmetic mean or the like of lengths of line segments corresponding to the segment S included in the detection result image Gd, or a value based on the average.

(Variant 2-1)

Figure 15:
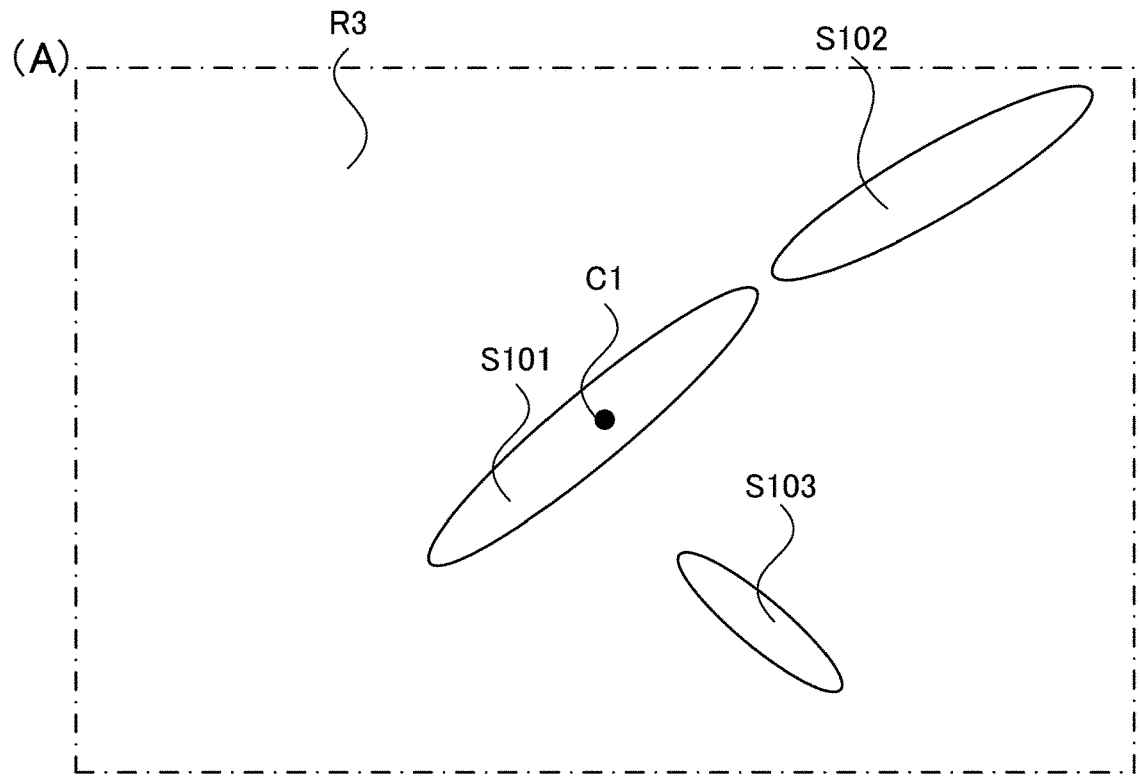
FIG. 15A is a conceptual view for describing setting of a search range according to Variant 2.
FIG. 15B is a conceptual view for describing setting of a search range according to Variant 2.
Figure 15:
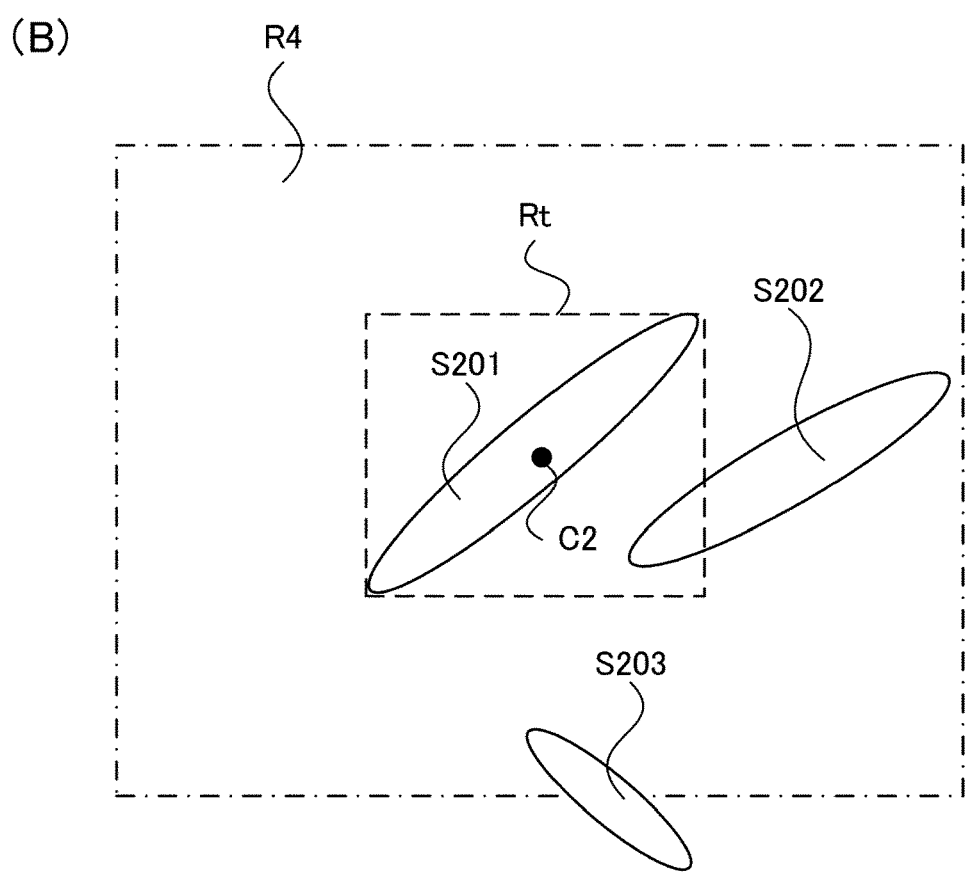

FIG. 15A is a conceptual view for describing a setting method of a search range R3 of the variant. The pair setting part 513 sets a rectangular or circular pixel region, in which a center of gravity C1 of a pixel of a segment S101 is used as a center, as the search range R3. The pair setting part 513 can set a pair of the segment S101 and each of the segments S102 and S103 having the pixels included in the search range R3 as a segment pair.

(Variant 2-2)

FIG. 15B is a conceptual view for describing a setting method of a search range R4 of the variant. The pair setting part 513 sets a rectangular pixel region, in which a center C2 of a rectangle Rt circumscribing the pixel of the segment S201 is used as a center, or a circular pixel region, as the search range R4. The pair setting part 513 can set a pair of the segment S201 and each of the segments S202 and S203 having pixels included in the search range R4 as a segment pair.

In the image processing device 1 of the above-mentioned Variant 2, the pair setting part 513 sets a pair of the segment S101 and the segment S102 and S103 including pixels in the search range R3 that is set to correspond to a center of gravity of the segment S101, or a set of the segment S201 and the segment S202 and S203 including pixels in the search range R4 that is set to correspond to the center of the rectangle Rt circumscribing the segment S201, among the plurality of segments S. Accordingly, the image processing device 1 can minimize variation of a position of the search range according to the shape of the segment S101 or S201, and can more accurately analyze how the extracted pixel group corresponds to the linear portion.

(Variant 3)

In the above-mentioned embodiment, the calculation part 514 may change a calculation method of a connecting degree when a distance between the first segment S1 and the second segment S2 included in the segment pair in the detection result image is greater than a predetermined distance. Hereinafter, the predetermined distance is referred to as a distance threshold DIST. A distance between the first segment S1 and the second segment S2 defined herein may be referred to as the distance w between the segments, may be an arbitrary distance defined on the basis of the first segment S1 and the second segment S2, or may be defined by a number of pixels corresponding to the arbitrary distance in the detection result image.

The pair setting part 513 sets the connecting degree DC of the second segment S2 with respect to the first segment S1 according to the following Equation (1) when the distance between the first segment S1 and the second segment S2 is smaller than the distance threshold DIST.

$$DC = c0 * |w| + c * \sin θ2 + c2 * \sin θ3 + c3 * (1 + \cos θ1) \tag{1}$$

The pair setting part 513 sets the connecting degree DC of the second segment S2 with respect to the first segment S1 according to the following Equation (2) when the distance between the first segment S1 and the second segment S2 is equal to or greater than DIST.

$$DC = c0 * |w| + c1 + c2 + 2 * c3 \tag{2}$$

Figure 16:
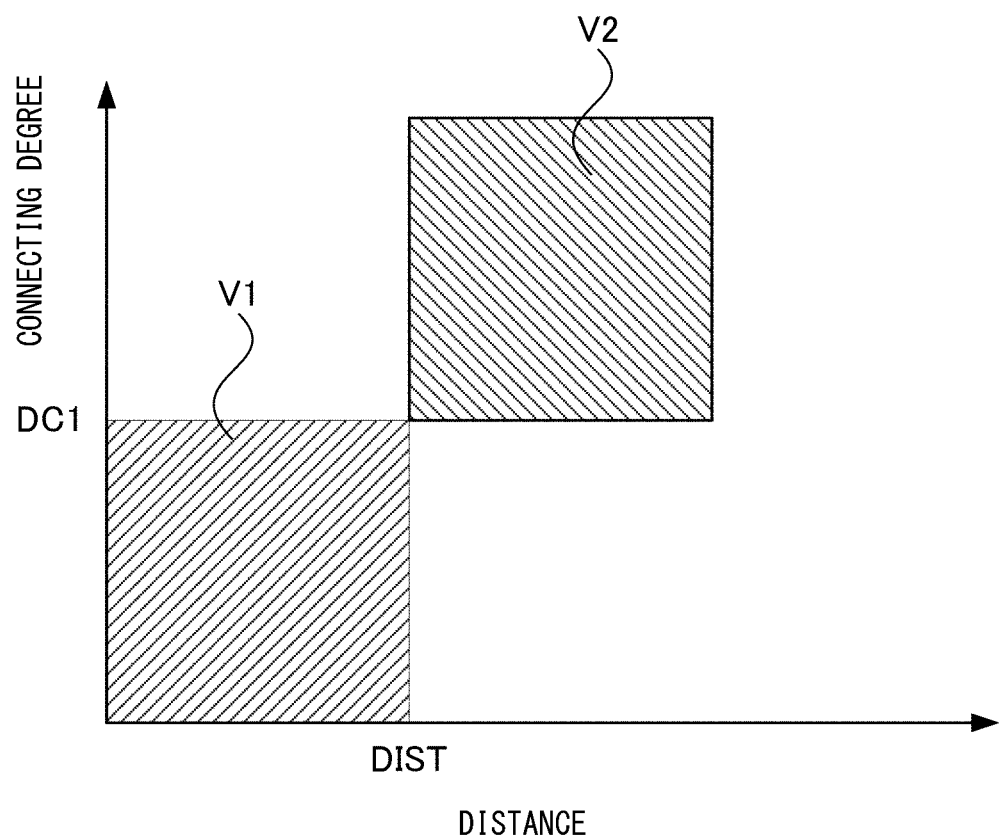
FIG. 16 is a graph showing a relation between a distance between pixel groups and a connecting degree according to Variant 3.

FIG. 16 is a graph showing a relation between the distance (lateral axis) between the first segment S1 and the second segment S2 and the connecting degree (vertical axis) of the second segment S2 with respect to the first segment S1 in the variant. In FIG. 16, a region V1 corresponding to the connecting degree calculated by the above-mentioned Equation (1) and a region V2 corresponding to the connecting degree calculated by the above-mentioned Equation (2) are shown by hatching. By comparing the case in which the distance between the first segment S1 and the second segment S2 is less than the distance threshold DIST with the case in which the distance is equal to or greater than the distance threshold DIST, except for a boundary value DC1=c0*DIST+c1+c2+2*c3, there is no overlap of the connecting degrees. Accordingly, the connecting degree when the distance between the first segment S1 and the second segment S2 is equal to or greater than the distance threshold DIST is a value that is equal to or greater than the connecting degree when less than the distance threshold DIST. Accordingly, in the case of the former, probability that the first segment S1 and the second segment S2 belong to different groups can be increased in comparison with the case of the latter.

Further, the calculation part 514 can change the calculation method of the connecting degree like when a pixel included in another segment S is present between the first segment S1 and the second segment S2 included in the segment pair, similarly. The pair setting part 513 sets the connecting degree DC of the second segment S2 with respect to the first segment S1 by the above-mentioned Equation (1) when the pixel included in the other segment S is not present between the first segment S1 and the second segment S2, for example, on the third line segment L3. The pair setting part 513 sets the connecting degree DC of the second segment S2 with respect to the first segment S1 by the above-mentioned Equation (2) when the pixel included in the other segment S is present between the first segment S1 and the second segment S2. Accordingly, when the pixel included in the other segment S is present between the first segment S1 and the second segment S2, it is possible to increase probability that the first segment S1 and the second segment S2 belong to different groups.

In the image processing device of the variant, when a first condition in which another pixel group acquired by the pixel group setting part 512 is present between the first segment S1 and the second segment S2 is satisfied or when a second condition in which a distance or a number of pixels between the first segment S1 and the second segment S2 is determined on the basis of the distance threshold DIST is satisfied, the calculation part 514 calculates the connecting degree using a method different from the case in which both of the first condition and the second condition are not satisfied. Accordingly, the image processing device 1 can more accurately analyze how the extracted pixel group corresponds to the linear portion to correspond to the aspect of the disposition of the two pixel groups.

(Variant 4)

In the above-mentioned embodiment, when the pixel group setting part 512 detects the cross, the calculation part 514 can set the connecting degree such that the segments S facing each other with the cross sandwiched therebetween belong to the same group.

Figure 17:
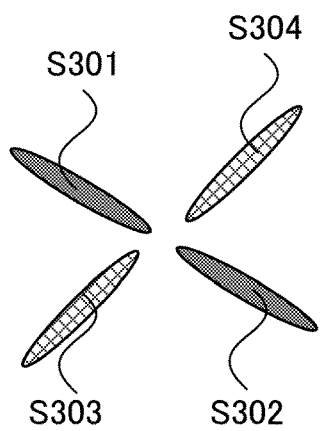
FIG. 17A is a conceptual view for describing setting of a connecting degree in a cross according to Variant 4.
FIG. 17B is a connection graph corresponding to FIG. 17A.
Figure 17:
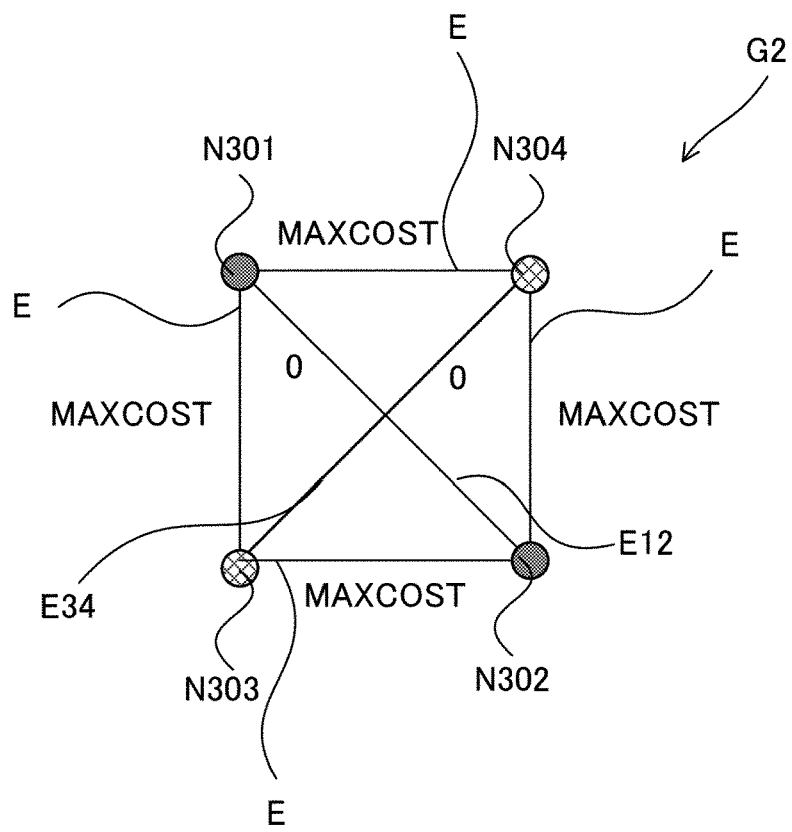

FIGS. 17A and 17B are conceptual views for describing setting of the connecting degree of the variant. FIG. 17A is a view showing four segments S301, S302, S303 and S304 that was connected to the cross after the cross is detected and removed. The pixel group setting part 512 stores information indicating that the segments S301, S302, S303 and S304 are segments that were connected to the removed cross after the cross is removed in the storage 43 or the like. For example, the pixel group setting part 512 includes a cross pixel group setting part configured to set the segments that were connected to the cross as one cross pixel group, and the pair setting part 513 and the calculation part 514 may process the cross pixel group with respect to the other segment S like one segment S. The calculation part 514 sets the connecting degree such that probability that the two segments S301 and S302 facing each other are connected and probability that the two segments S303 and S304 facing each other are connected are smaller than probability that the other two segments of the segments that were connected to the cross are connected, after referring the above mentioned information.

FIG. 17B is the weighted connection graph 62 corresponding to the segments S301 to 304. Nodes corresponding to the segments S301, S302, S303 and S304 are designated by N301, N302, N303 and N304. The calculation part 514 sets weights of an edge that connects the nodes N301 and N302 and an edge that connects the nodes N303 and N304 to 0. The calculation part 514 sets a weight of another edge E that connects the nodes N301 to N304 to the maximum (MAXCOST), except these two edges. The calculation part 514 calculates which segment S faces four regions corresponding to the cross before the connecting degree for the other segment S is calculated, and sets the connecting degree to increase probability that the two segments S determined as facing each other are connected. By performing the grouping after setting of the above-mentioned connecting degree, the two segments S determined as facing each other during grouping can be securely connected.

Further, when the two segments S facing each other are likely to be grouped into the same group, a specific value of the weight of the edge is not particularly limited. In addition, the cross pixel group setting part may set the segment including the pixels within the fixed range from any one of the segments S301 to S304 as the segment that constitutes the cross pixel group.

In the image processing device according to the variant, the calculation part 514 calculates the connecting degree such that the pair of the segments S that is generated by excluding the pixel corresponding to the cross and that faces each other with the cross sandwiched therebetween corresponds to a part of the connected linear region. Accordingly, the image processing device can more accurately analyze how the extracted pixel group including the cross corresponds to the linear portion.

In the image processing device according to the variant, the pixel group setting part 512 includes the cross pixel group setting part configured to collectively set the four segments S including the segment S301 and the three pixel groups S302, S303 and S304 as the cross pixel group when the other three pixel groups S302, S303 and S304 are present within a fixed range from the segment S301, and the calculation part 514 can calculate the connecting degree such that the pair of the segments S facing each other with the cross sandwiched therebetween corresponds to a part of the connected linear region. Accordingly, the image processing device can more accurately analyze how the extracted pixel group including the cross corresponds to the linear portion.

(Variant 5)

In the above-mentioned embodiment, the calculation part 514 can calculate the connecting degree on the basis of the characteristics of at least one of the segments S further shown in the following Variant 5-1 to 5-4.

(Variant 5-1)

The calculation part 514 may calculate the connecting degree on the basis of the average value such as the arithmetic mean or the like of the luminance of the pixel included in each of the first segment S1 and the second segment S2. The luminance in this case can use the luminance of the captured image or the probability distribution image Gp, in addition to the detection result image Gd. As the difference between the average value of the luminance of the pixel of the first segment S1 and the average value of the luminance of the pixel of the second segment S2 is reduced, the connecting degree can be set to become smaller such that the first segment S1 and the second segment S2 tend to be in the same group.

(Variant 5-2)

The calculation part 514 may calculate the connecting degree on the basis of the width of the first segment S1 and the width of the second segment S2. The width in this case can be set by, for example, the number or the like of the pixels through which a straight line perpendicular to the line segment corresponding to each of the first segment S1 and the second segment S2 passes. The calculation part 514 can be set such that, as the difference between the width of the first segment S1 and the width of the second segment S2 is reduced, the connecting degree becomes smaller and the first segment S1 and the second segment S2 tend to be in the same group.

(Variant 5-3)

The calculation part 514 may calculate the connecting degree on the basis of a curvature of a curved line corresponding to the first segment S1 and a curvature of a curved line corresponding to the second segment S2. The curvature in this case can be used for the curved line or the like calculated by a known fitting method or the like for each of the first segment S1 and the second segment S2. The calculation part 514 can be set such that, as the difference between the curvature of the curved line corresponding to the first segment S1 and the curvature of the curved line corresponding to the second segment S2 is reduced, the connecting degree becomes smaller and the first segment S1 and the second segment S2 tend to be in the same group.

(Variant 5-4)

The calculation part 514 may calculate the connecting degree on the basis of the length of the straight line portion of at least a part of the polygonal line corresponding to the first segment S1 and the length of the straight line portion of at least a part of the polygonal line corresponding to the second segment S2. In this case, it is preferable to use the length of the straight line portion closest to the second segment in the first segment S1 and closest to the first segment in the second segment S2. As the length of the straight line portion becomes longer, the first angle $\theta 1$ or the like can be more accurately calculated and the grouping can be performed more accurately. The polygonal line can use a polygonal line calculated by a known fitting method or the like for each of the first segment S1 and the second segment S2. The calculation part 514 can be set such that, as the difference between the length of the straight line portion corresponding to the first segment S1 and the length of the straight line portion corresponding to the second segment S2 is reduced, the connecting degree becomes smaller and the first segment S1 and the second segment S2 tend to be in the same group.

In the image processing device of the variant, the calculation part 514 calculates the connecting degree on the basis of at least one of the average value of the luminance of the plurality of pixels Px that constitute the first segment S1 and the second segment S2, the widths of the first segment S1 and the second segment S2, the curvature of the curved line when the curved line corresponds to the first segment S1 and the second segment S2, and the length of the line segment that constitutes the polygonal line when the first segment S1 or the second segment S2 corresponds to the polygonal line. Accordingly, the image processing device can more accurately analyze how the extracted pixel group corresponds to the linear portion on the basis of these characteristics (for example, a width, a curvature, or the like).

(Variant 6)

In the above-mentioned embodiment, while the subject of the captured image will be described as the cell Ce and the linear portion of the extraction target will be described as the neurite Nr, the extraction target is not limited to this example as long as, including the linear portion, and for example, it is also preferable to use the blood vessel.

Further, it is more preferable that the subject of the captured image is the eyeground and the linear portion of the extraction target is the blood vessel in the eyeground, and in particular, it is further preferable that the subject is a retina blood vessel or a choroid blood vessel. In the eyeground image, the linear portion of the extraction target is the blood vessel, and the detection result image generating part 511 generates the probability distribution image Gp in which the probability that each pixel corresponds to the blood vessel corresponds to the luminance value from the captured image, and generates the detection result image Gd from the probability distribution image Gp. Since the pixel group setting part 511, the pair setting part 512, the calculation part 514 and the determination part 600 perform the above-mentioned processing for the generated detection result image Gd, the blood vessels connected to each other can be appropriately extracted. In this case, the execution part 601 can set the type of segmented blood vessel or the like for some pixels of the detection result image Gd as a root node that is not a virtual node of the minimum spanning tree. Here, the type of the blood vessel can include artery, vein, or the like. When the segments S corresponding to the choroid blood vessels are grouped, the plurality of choroidal veins can be set as the root node, and the segments S can be grouped on the basis of whether the segment is connected to the choroidal vein corresponding to each root node.

In the image processing device of the variant, the detection result image Gd is an image showing the plurality of pixels Px1 corresponding to the blood vessel, and the connecting degree is a numerical value indicating possibility that the first segment S1 and the second segment S2 correspond to a part of the same blood vessel. Accordingly, the image processing device can accurately analyze how the pixel group extracted from the captured image corresponds to a part of the blood vessel divided to the root nodes, also including the broken pixel segment.

(Variant 7)

In the above-mentioned embodiment, the data processing part may calculate at least one of the second angle $\theta 2$ and the third angle $\theta 3$ for the two segments S set by the pixel group setting part 512, or may determine whether the two segments S correspond to the same linear portion in the object on the basis of whether the calculated second angle $\theta 2$ and third angle $\theta 3$ are within the predetermined range that is previously determined.

Figure 18:
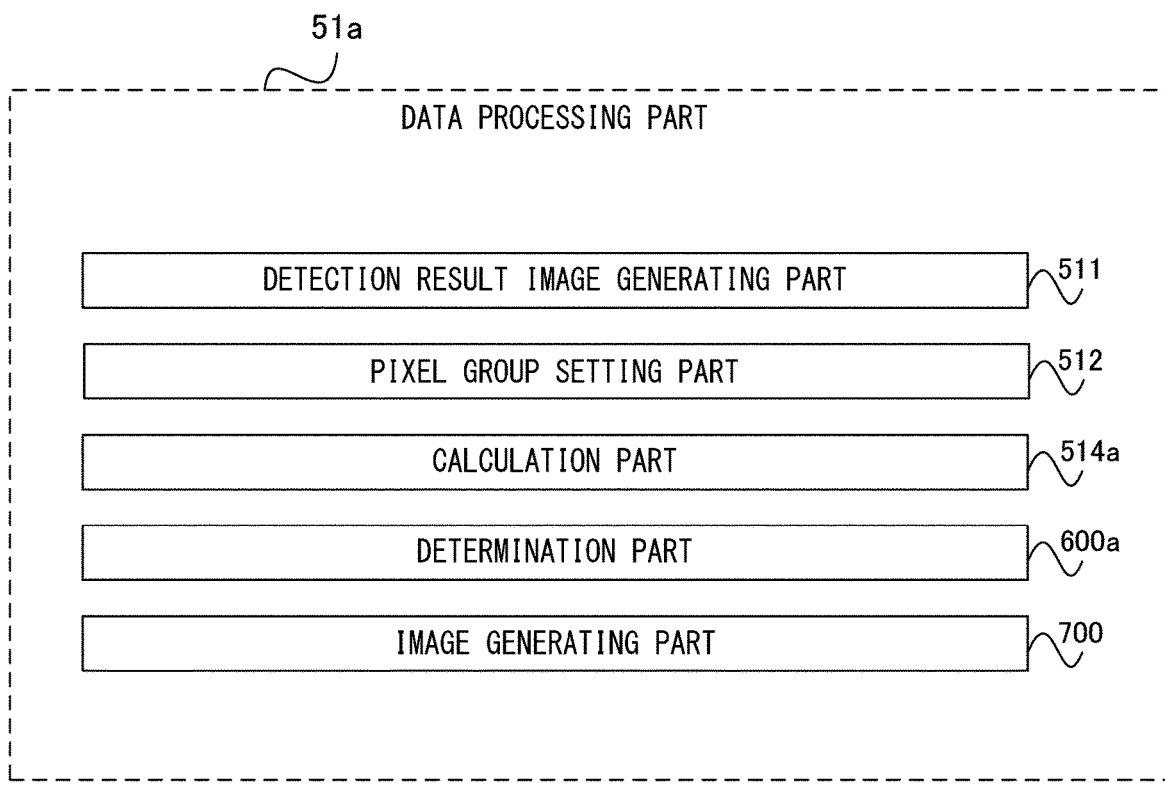
FIG. 18 is a conceptual view showing a configuration of a data processing part according to Variant 7.

FIG. 18 is a conceptual view showing a configuration of a data processing part 51*a* in the image processing device of the variant. The data processing part 51*a* includes the detection result image generating part 511, the pixel group setting part 512, a calculation part 514a, a determination part 600a, and the image generating part 700. The calculation part 514a calculates at least one of the second angle θ2 and the third angle θ3 for the two segments S among the segments S set by the pixel group setting part 512. The determination part 600a determines that the two segments S correspond to the same neurite Nr when at least one of the calculated second angle θ2 and third angle θ3 is included within a numerical value range showing the predetermined range stored in the storage 43 or the like. The predetermined range is appropriately set such that the two segments S are linearly arranged. According to the method of the variant, it is possible to accurately analyze how the extracted pixel group corresponds to the linear portion.

(Variant 8)

A program configured to realize an information processing function of the information processing part 40 of the above-mentioned embodiment may be recorded on a computer-readable recording medium, and a program recorded in the recording medium and related to the processing or the like by the data processing part 51 such as the setting or the like of the above-mentioned segment S, segment pair and connecting degree may be loaded into a computer system and executed. Further, "the computer system" disclosed herein includes an operating system (OS) or hardware such as peripheral devices. In addition, "the computer-readable recording medium" is referred to as a portable recording medium such as a flexible disk, a magneto-optical disk, an optical disk, a memory card, or the like, or a storage device such as a hard disk or the like installed in the computer system. Further, "the computer-readable recording medium" may include a medium that dynamically holds a program for a short time, such as a communication line when the program is transmitted via a network such as the Internet or the like or a communication circuit such as a telephone circuit or the like, or a medium that holds a program for a fixed time such as a volatile memory in a computer system that becomes a server or a client in this case. In addition, the program may be provided to realize a part of the above-mentioned function, and may be further realized by combining the above-mentioned function with the program already recorded in the computer system.

Figure 19:
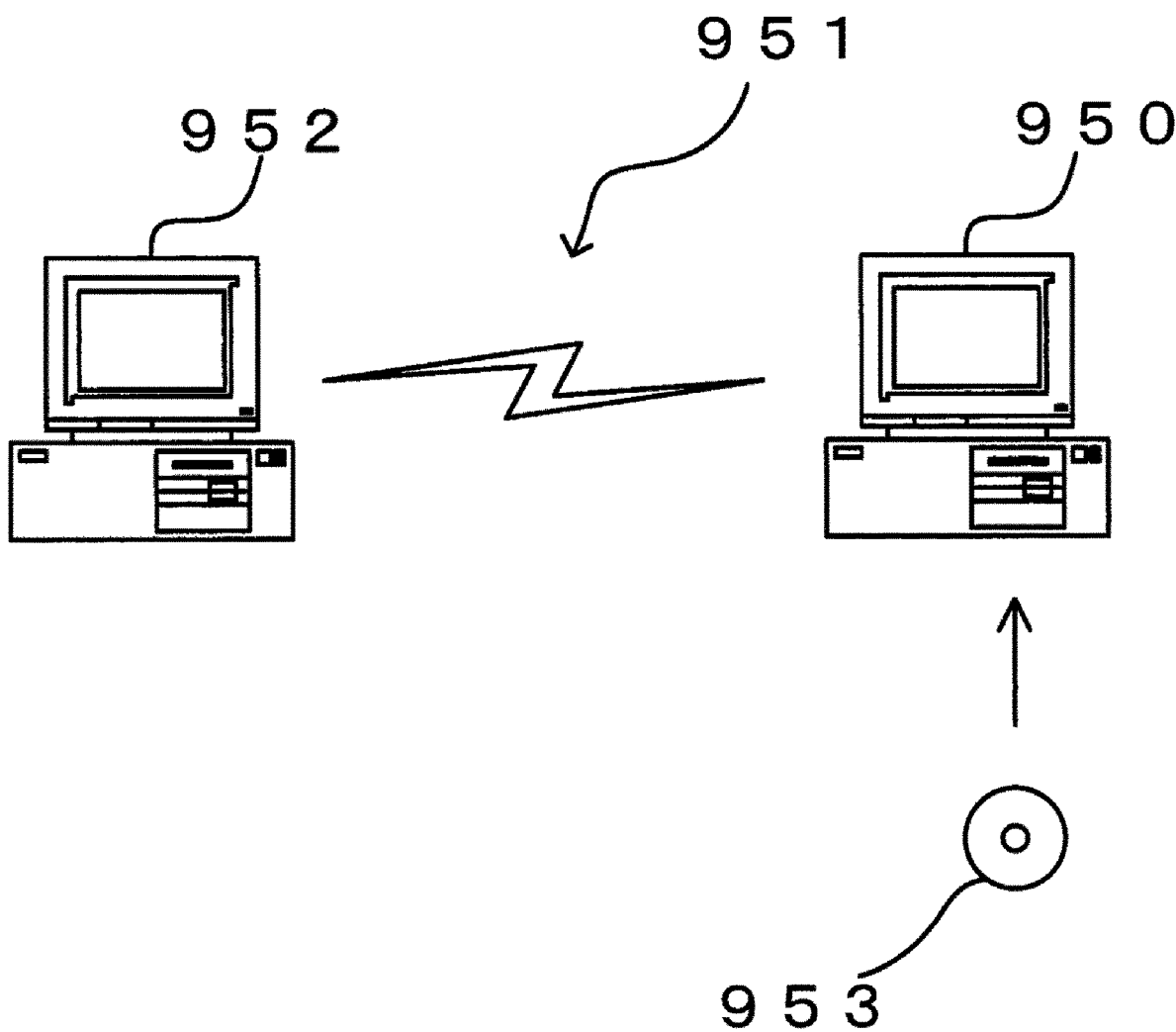
FIG. 19 is a conceptual view for describing provision of a program according to Variant 8.

In addition, when the program is applied to a personal computer (hereinafter, referred to as PC) or the like, the program related to the above-mentioned control can be provided through a recording medium such as CD-ROM or the like, or data signal of the Internet or the like. FIG. 19 is a view showing the aspect. A PC 950 receives the program via a CD-ROM 953. In addition, the PC 950 has a connecting function to a communication circuit 951. A computer 952 is a server computer configured to provide the program, and stores the program in a recording medium such as a hard disk or the like. The communication circuit 951 is a communication circuit such as the Internet, a personal computer communication, or the like, a dedicated communication circuit, or the like. The computer 952 reads the program using the hard disk and transmits the program to the PC 950 via the communication circuit 951. That is, the program is carried as data signal by carrier waves and transmitted via the communication circuit 951. In this way, the program can be supplied as various types of computer-readable computer program products such as a recording medium, carrier waves, or the like.

As a program for realizing the above-mentioned information processing function, a program for causing the processing device to perform pixel group setting processing (corresponding to step S107 of the flowchart of FIG. 11) of setting the plurality of segments S including the first segment S1 and the second segment S2, which are not connected to each other, from the plurality of pixels Px that constitute the detection result image Gd, and set setting processing (corresponding to step S1095 of the flowchart of FIG. 12) of setting a pair of the first segment S1 and the second S2 including the pixel within the predetermined range from the first segment S1 among the plurality of segments S in order to set the connecting degree with respect to the first segment S1, is included. Accordingly, it is possible to accurately analyze how the extracted pixel group corresponds to the linear portion, also including the broken pixel segment.

As the program for realizing the above-mentioned information processing function, a program for causing the processing device to perform pixel group setting processing (corresponding to step S107 of the flowchart in FIG. 11) of acquiring the first segment S1 and the second segment S2, which are not connected to each other, from the detection result image Gd, calculation processing (corresponding to step S1097 of the flowchart of FIG. 12) of calculating the second angle θ2 formed between and the first line segment L1 and the third line segment L3 which passes through the first line segment L1 corresponding to the first segment S1 and the second line segment L2 corresponding to the second segment S2, and determination processing (corresponding to step S111 of the flowchart of FIG. 11) of determining whether the first segment S1 and the second segment S3 correspond to the connected linear region on the basis of the second angle θ2, is included. Accordingly, it is possible to accurately analyze how the extracted pixel group corresponds to the linear portion on the basis of the positional relation between the first segment S1 and the second segment S2.

(Variant 9)

In the embodiment, processing by the data processing part 51 may be provided by cloud computing via the network.

Figure 20:
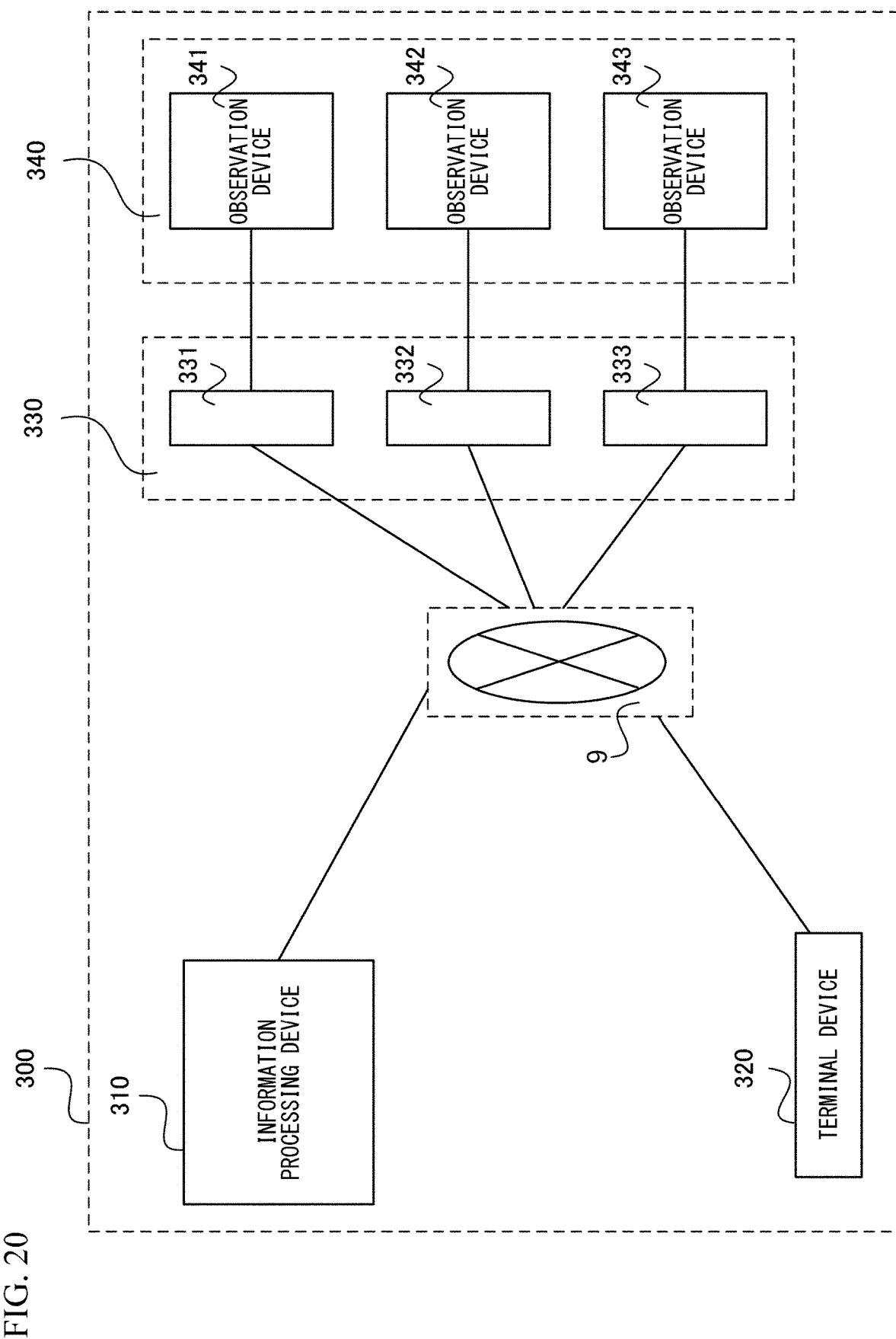
FIG. 20 is a conceptual view showing a configuration of a quality evaluation system according to Variant 9.

FIG. 20 is a conceptual view showing a configuration of a quality evaluation system 300 according to the variant. The quality evaluation system 300 includes an information processing device 310, a terminal device 320, and a gateway terminal 330. The quality evaluation system 300 evaluates quality of an observation target of an observation device 340 such as a cultivated cell or the like through data processing of an image of the observation target. As such an observation target, it is preferable to include the linear portion such as a neuron having a neurite or the like.

In the variant, the information processing device 310, the terminal device 320 and the gateway terminal 330 are connected to communicate with each other via a network 9. The network 9 may be the Internet, a mobile communication network, a local area network, or the like, or may be a network obtained by combining the plurality of types of networks.

The gateway terminal 330 transmits the captured image captured by the observation device 340 to the information processing device 310 via the network 9. While three gateway terminals 331, 332 and 333 are shown in FIG. 20 as the gateway terminal 330, the number of the gateway terminals 330 in the quality evaluation system is not particularly limited. The gateway terminals 331, 332 and 333 are connected to communicate with observation devices 341, 342 and 343, respectively, in a wireless or wired manner. The observation device 340 is handled by a manager of the observation target such as a cell or the like. The number of the observation devices 340 is three in FIG. 20, but it may be an arbitrary number of 1 or more.

The observation device 340 is not particularly limited as long as the image of the observation target can be captured. The observation device 340 may include, for example, the above-mentioned cultivation part 100. The observation device 340 can transmit the captured image data to the gateway terminal 330 using a control PC or the like of the observation device 340 including a communication device configured to transmit the captured image data obtained through imaging to the gateway terminal 330 or being not integrally with the observation device. The observation device 340 includes a detector configured to detect, for example, a temperature in cultivation, an atmospheric pressure, illuminance and oxygen concentration of a light source, and the like, and can transmit data obtained by detection to the gateway terminal 330.

While the gateway terminal 330 is a general-purpose gateway configured to typically convert protocols or addressing architectures to each other, it is not particularly limited thereto. The gateway terminal 330 may be a PC or the like having a function of the gateway. While the gateway terminal 330 is preferably constituted by the plurality of gateway terminals 330 from a viewpoint of improvement of analysis accuracy of the information processing device 310, it may be constituted by a single gateway terminal. In this case, the one gateway terminal 330 and the plurality of observation devices 340 are connected to communicate with each other.

Figure 21:
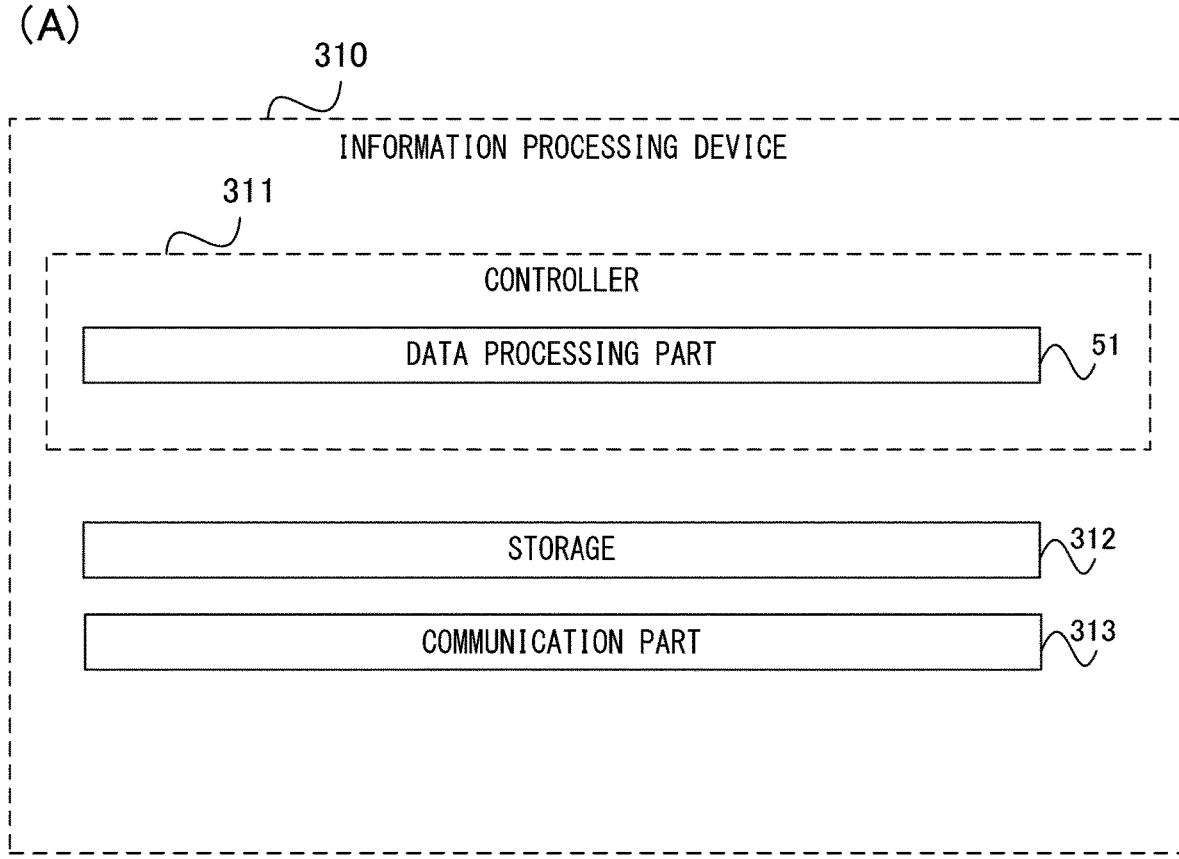
FIG. 21A is a conceptual view showing a configuration of an information processing device according to Variant 9.
FIG. 21B is a conceptual view showing a configuration of a terminal device according to Variant 9.
Figure 21:
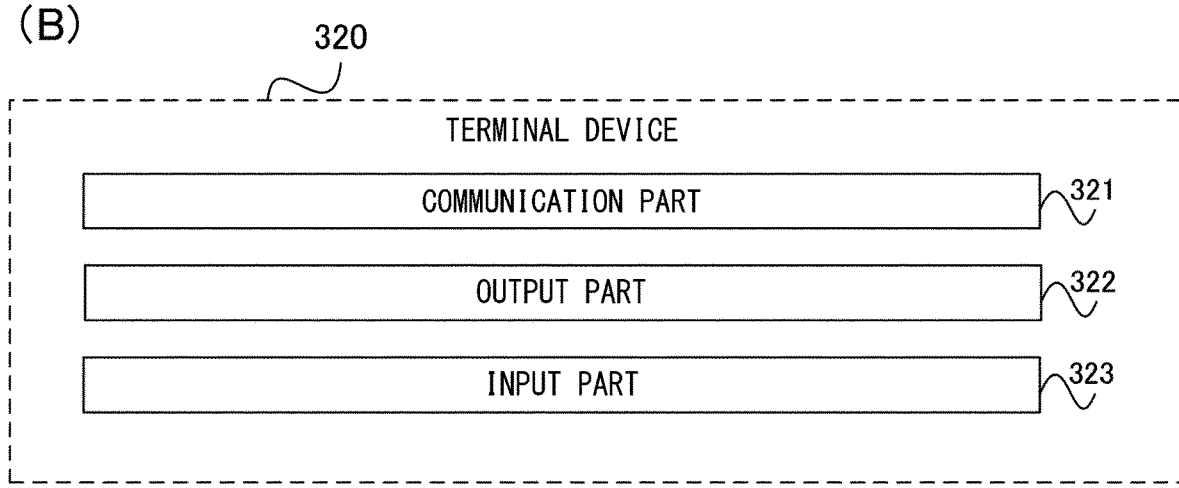

FIG. 21(A) is a conceptual view showing a configuration of the information processing device 310. The information processing device 310 includes a controller 311, a storage 312, and a communication part 313. While the information processing device 310 of the variant is a web server configured to perform quality evaluation of the observation target of the observation device 340 through cloud computing, it is not particularly limited thereto. The information processing device 310 may be constituted by an arbitrary computer such as a PC or the like.

The controller 311 is constituted by a processing device such as a CPU or the like, functions as a main constituent of an operation of controlling the information processing device 310, and performs various types of processing by executing the program installed in the storage 312. The controller 311 includes the above-mentioned data processing part 51, and performs processing of setting or the like of the segment S, the segment pair and the connecting degree (for example, analysis processing, processing of a first algorithm, calculation processing of a connecting degree) with respect to the captured image data received and acquired from the observation device 340 via the network 9. The controller 311 transmits information, which indicates the result of the grouping of the segments S in the detection result image Gd obtained through the processing, or output image data of the output image, which displays the segments S determined as the same group with the same color or the same luminance, to the terminal device 320 via the communication part 313.

The storage 312 of the information processing device 310 includes a non-volatile storage medium, and stores data and programs used for the processing in the information processing device 310, data obtained through the processing of the data processing part 51, and the like. The communication part 313 of the information processing device 310 includes a communication device that is communicable via the network 9, and receives captured image data or the like transmitted from the observation device 340 or transmits information or the like generated by the controller 311 to the terminal device 320.

FIG. 21(B) is a conceptual view showing a configuration of the terminal device 320. The terminal device 320 is handled by a quality evaluator or the like of the observation target of the observation device 340. The terminal device 320 may be configured to include an arbitrary computer such as a PC, a smart phone, a tablet, or the like. The terminal device 320 includes a communication part 321, an output part 322, and an input part 323.

The communication part 321 of the terminal device 320 includes a communication device that is communicable via the network 9, and receives information or the like transmitted from the information processing device 310 and obtained through processing of the data processing part 51. The information may include positional information of the segments S belonging to the same group or an output image in which the segments belonging to the same group are colored in the same color. In addition, the information may include a detection result image before the trigeminal or the cross is removed when the trigeminal or the cross is removed by the detection processing of the trigeminal or the cross in advance. The output part 322 of the image terminal device 320 includes a display device such as a liquid crystal monitor or the like, and outputs an image or the like showing the information obtained by processing of the data processing part 51. A user (for example, a quality evaluator) can evaluate the observation target of the observation device 340 by observing the image or the like displayed on the output part 322 or data-analyzing the image or the like. For example, when the observation target is the neuron, in the data analysis, the length or the number of neurites can be quantified. Evaluation by the quality evaluator may be input from an input part (not shown) of the terminal device 320, and the input data may be transmitted to the information processing device 310 via the communication part 321 and stored in the storage 312 of the information processing device 310. Further, the captured image data received by the controller 311 may be transmitted to the information processing device 310 by a user using the input part 323 included in the terminal device 320.

(Variant 10)

In the above-mentioned embodiment, in detection and removal of the trigeminal and the cross, setting of the segments S, setting of the segment pair and the connecting degree, and determination of the grouping, the user can appropriately observe a display screen of the output part 44 and input or change the parameters for these. Hereinafter, the trigeminal or the cross is referred to as an intersection, and detection and removal of the intersection are referred to as intersection removing processing. In addition, setting of the segment S, setting of the segment pair and the connecting degree, and determination of the grouping are referred to as assignment processing.

Figure 22:
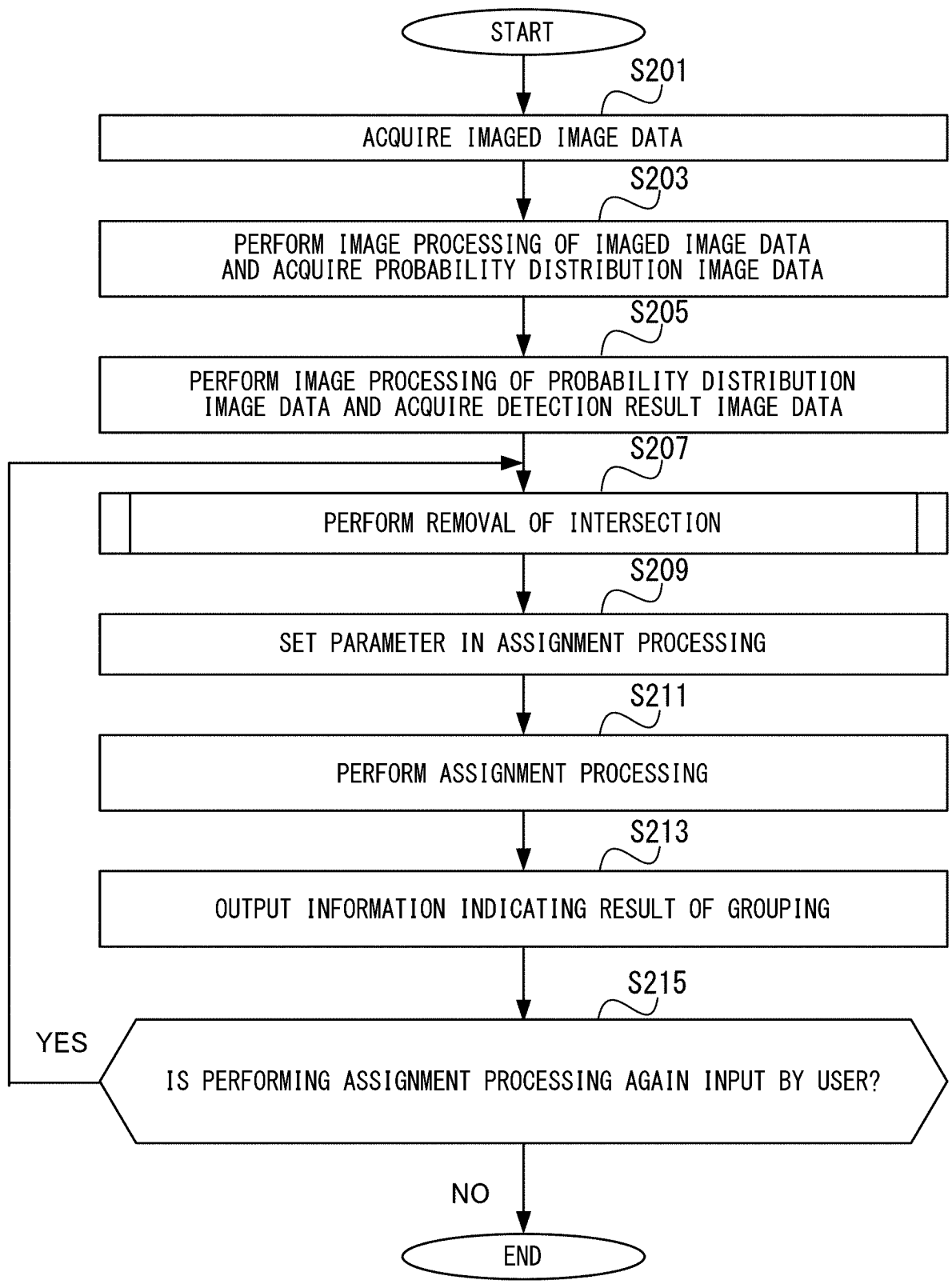
FIG. 22 is a flowchart showing a flow of an image processing method according to Variant 10.

FIG. 22 is a flowchart showing a flow of an image processing method of the variant. Since steps S201 to S205 are the same as steps S101 to S105 of the flowchart of FIG. 11, description thereof will be omitted. When step S205 is terminated, step S207 is started.

In step S207, the pixel group setting part 512 performs removal of the intersection in the detection result image Gd.

Figure 23:
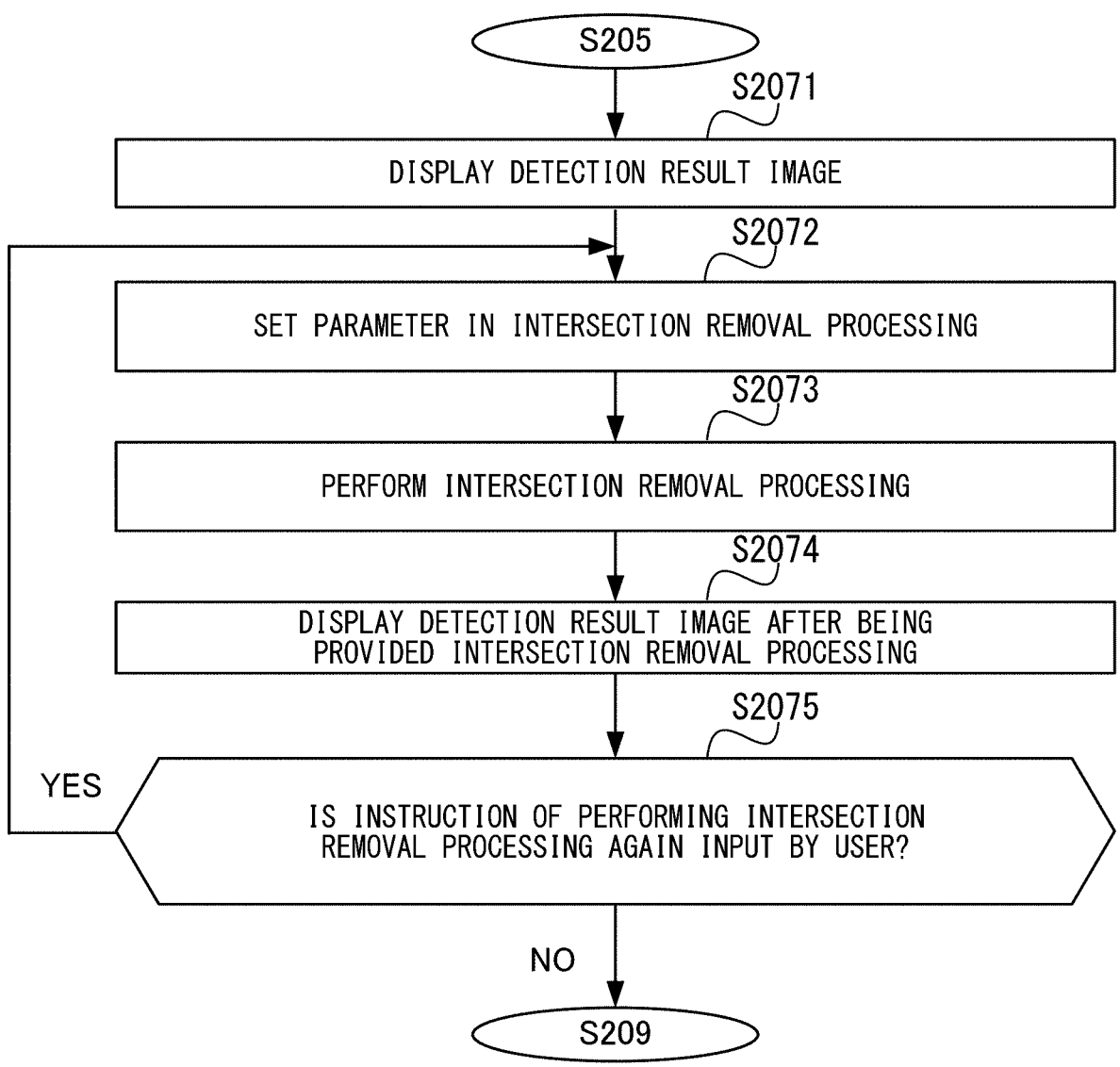
FIG. 23 is a flowchart showing a flow of the image processing method according to Variant 10.

FIG. 23 is a flowchart showing a flow of removal of the intersection of step S207. When step S205 is terminated, step S2071 is started. In step S2071, the output controller 52 displays the detection result image Gd on the display screen of the output part 44. When step S2071 is terminated, step S2072 is started. In step S2072, the pixel group setting part 512 sets parameters in intersection removing processing. The parameters in the intersection removing processing are referred to as intersection detection parameters. The intersection detection parameters may include a numerical value indicating a size of the removed pixel region Re (FIG. 5B), in particular, a number of pixels (width) or the like of the removed pixel region Re in a lateral direction or a longitudinal direction.

A user can input the intersection detection parameter via the input part 41 by observing the captured image or the detection result image Gd and further observing the intersection removing result image, which will be described below, already obtained when the intersection removing processing is performed again after performing the intersection removing processing. For example, the user can set a width of the removed pixel region Re to be similar to the segment width of the segment S in the detection result image Gd, or set the width of the removed pixel region Re longer when there are many irregularities in the shape of the segment S in the detection result image Gd. Alternatively, the user can set the width of the removed pixel region Re smaller when there are many misdetection of the intersections in the intersection removing result image, and set the width of the removed pixel region Re larger when there are many intersections that were not detected in the intersection removing processing. The pixel group setting part 512 sets the intersection detection parameters on the basis of the input of the user via the input part 41. When step S2072 is terminated, step S2073 is started.

In step S2073, the pixel group setting part 512 performs the above-mentioned intersection removing processing using the intersection detection parameters set in step S2072 through the same method as the above-mentioned embodiment. When step S2073 is terminated, step S2074 is started. In step S2074, the output controller 52 displays the detection result image after being provided in the intersection removing processing on the display screen of the output part 44. The detection result image after being provided in the intersection removing processing is referred to as an intersection removing result image. When step S2074 is terminated, step S2075 is started.

In step S2075, the data processing part 51 determines whether the user has instructed to perform another intersection removing processing via the input part 41. When the instruction is input, the data processing part 51 makes a positive determination in step S2075, and step S2072 is started. When the instruction is not input, the data processing part 51 makes a negative determination in step S2075, and step S209 is started.

Returning to FIG. 22, in step S209, the data processing part 51 sets parameters in the assignment processing. The parameters in the assignment processing are referred to as assignment parameter. The assignment parameters may include a weight $c_0$ of a term including the distance w between the segments in Equation (1) of the above-mentioned embodiment, a weight $c_1$ of a term including the second angle $\theta_2$, a weight $c_2$ of a term including the third angle $\theta_3$, and a weight $c_3$ of a term including the first angle $\theta_1$. Further, the assignment parameter can show whether the processing of setting the connecting degree is performed such that the segments S facing each other are connected to the four segments S corresponding to the cross like the above-mentioned Variant 4 using binary values or the like. A variable indicated by the binary values is set as f. In addition, the assignment parameters may include arbitrary parameters used in the assignment processing. For example, like the above-mentioned Variant 5, when a difference in width between the segments S or a difference in luminance between the segments is used for calculation of the connecting degree, a weight $c_4$ of a term including a difference in width between the segments S in the equation that calculates the connecting degree and a weight $c_5$ of a term including a difference in luminance between the segment may be included in the assignment parameters. The calculation part 514 can calculate the connecting degree by eliminating the term including the distance w between the segments when the distance w between the segments is equal to or greater than the predetermined value in calculation of the connecting degree. A predetermined value D may be included in the assignment parameters.

The user can input the assignment parameters via the input part 41 when the captured image, the detection result image Gd or the intersection removing result image is seen, and further, when the assignment result image, which will be described below, already obtained is seen when the assignment processing is performed again after the assignment processing is performed. For example, the user can set the predetermined value D to about twice the value of the intersection detection parameter. The user can set the values of the weights $c_1$, $c_2$ and $c_3$ high when the curvature of the segment S in the detection result image Gd is small, and can set the values of the weights $c_1$, $c_2$ and $c_3$ low and the value of the weight $c_0$ high when the curvature of the segment S large or there is a lot of noise. Alternatively, the user sets the value of the weight $c_4$ of the term including the width of the segment S high when a variation of the width of the segment S is large, and sets the value of the weight $c_4$ low, for example, 0 when the variation is small. The data processing part 51 sets the assignment parameter on the basis of the input of the user via the input part 41. When step S209 is terminated, step S211 is started.

In step S211, the data processing part 51 performs the above-mentioned assignment processing through the same method as the above-mentioned embodiment using the assignment parameters set in step S209. When step S211 is terminated, step S213 is started. In step S213, the output controller 52 displays the above-mentioned output image obtained by the assignment processing on the display screen of the output part 44. Hereinafter, the output image is an image in which the segment S has at least one of color, brightness and chroma that differ for each group, which is referred to as an assignment result image. When step S213 is terminated, step S215 is started.

In step S215, the data processing part 51 determines whether an instruction to perform the assignment processing again by the user was input via the input part 41. When the instruction is input, the data processing part 51 makes a positive determination in step S215, and step S207 is started. When the instruction is not input, the data processing part 51 makes a negative determination in step S215, and processing is terminated.

Further, the data processing part 51 may start step S209 after the positive determination is made in step S215.

Hereinafter, regarding the above-mentioned intersection removing processing, while the example of the display screen displayed in the output part 44 is shown, the aspect of the image on each display screen and the shapes of the button and the icon are not limited to those shown in the following drawings.

Figure 24:
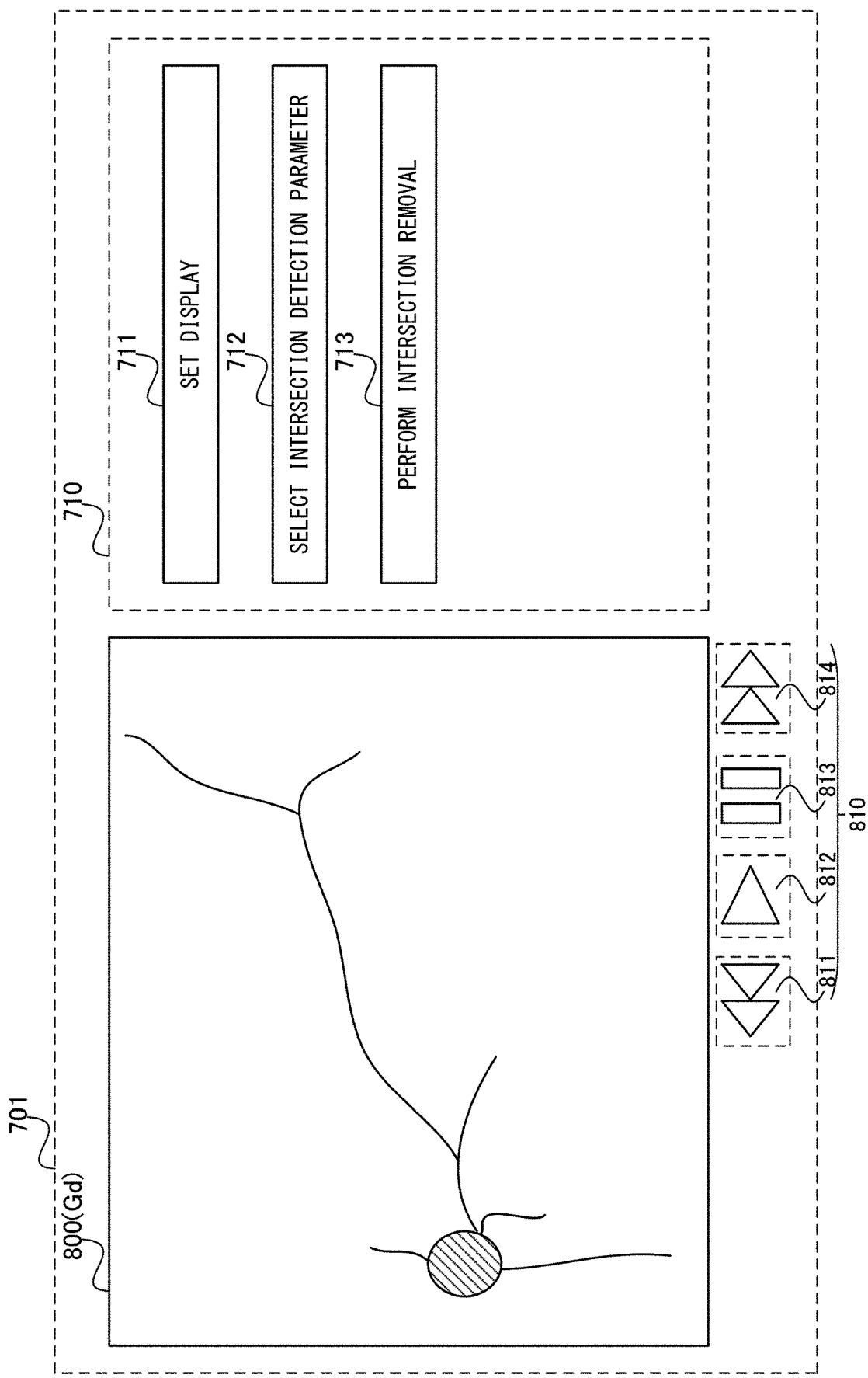
FIG. 24 is a conceptual view showing an example of a display screen according to Variant 10.

FIG. 24 is an example of a screen displayed on the output part 44 before the intersection removing processing is performed, and the screen is a first basic screen 701. The first basic screen 701 includes an image display unit 800, a first input element display unit 710, and a video operation unit 810. The first input element display unit 710 includes a first display setting button 711, an intersection detection parameter selection button 712, and an intersection removing execution button 713. The video operation unit 810 includes a rewinding button 811 configured to perform rewinding when video is displayed on the image display unit 800, a reproduction button 812 configured to perform reproduction, a pause button 813 configured to perform a pause, and a fast forward button 814 configured to perform fast forward. While the detection result image Gd is shown on the image display unit 800 of the first basic screen 701 of FIG. 24, the image displayed on the image display unit 800 can be appropriately changed.

The first input element display unit 710 includes the buttons 711, 712 and 713 that are input elements for the user to cause the image processing device 1 to perform predetermined operations by clicking a cursor together with a mouse, a touch pad, or the like.

The first display setting button 711 is an input element configured to shift the display screen to the first display setting screen that is a screen configured to set an image displayed on the image display unit 800. When the first display setting button 711 is clicked, the output controller 52 displays a first display setting screen 702 of FIG. 25 on the output part 44.

The intersection detection parameter selection button 712 is an input element configured to shift the display screen to an intersection detection parameter selection screen that is a screen configured to input an intersection detection parameter. When the intersection detection parameter selection button 712 is clicked, the output controller 52 displays an intersection detection parameter selection screen 703 of FIG. 26 on the output part 44.

The intersection removing execution button 713 is an input element configured to cause the pixel group setting part 512 to execute the intersection removing processing, and shift the display screen to a first result display screen that is a screen configured to display a result of the intersection removing processing. When the intersection removing execution button 713 is clicked, the output controller 52 displays a first result display screen 704 of FIG. 27 on the output part 44.

Figure 25:
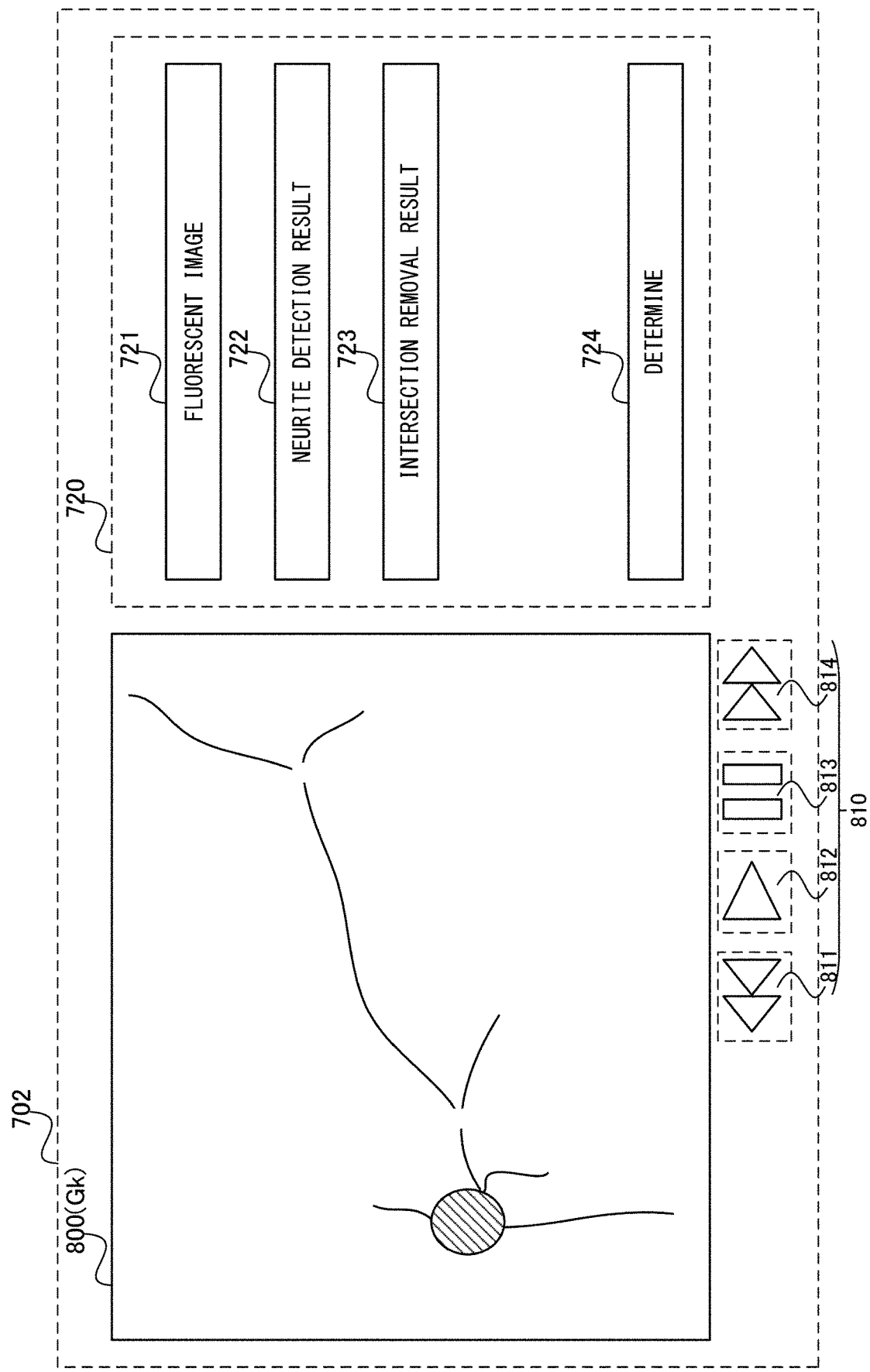
FIG. 25 is a conceptual view showing an example of a display screen according to Variant 10.

FIG. 25 is a view showing an example of the first display setting screen 702. The first display setting screen 702 includes the image display unit 800, a first image selection unit 720, and the video operation unit 810. The first image selection unit 720 includes a first captured image display button 721, a first detection result image display button 722, a first intersection removing result image display button 723, and a first determine button 724. Before these buttons are clicked, the output controller 52 can display the image displayed on the first basic screen 701 or the like so far on the image display unit 800.

The first image selection unit 710 includes the buttons 721, 722, 723 and 724 that are input elements configured to perform selection of the image displayed on the image processing unit 800 as the user clicks with the cursor using a mouse, a touch pad, or the like.

The first captured image display button 721 is an input element configured to display the captured image on the image display unit 800 by clicking the first captured image display button 721. Hereinafter, a fluorescent image of the captured cell Ce is displayed using a fluorescence microscope as the captured image. When the first captured image display button 721 is clicked, the output controller 52 displays the captured image on the image display unit 800.

The first detection result image display button 722 is an input element configured to display the detection result image Gd on the image display unit 800 by clicking the first detection result image display button 722. When the first detection result image display button 722 is clicked, the output controller 52 displays the detection result image on the image display unit 800.

The first intersection removing result image display button 723 is an input element configured to display an intersection removing result image Gk on the image display unit 800 by clicking the first intersection removing result image display button 723. When a first intersection removing result image display button 722 is clicked, the output controller 52 displays the intersection removing result image Gk on the image display unit 800. In the example of FIG. 25, an intersection result image Gk displayed after the first intersection removing result image display button 722 is clicked is shown.

The first determine button 724 is an input element configured to shift the display screen to the first basic screen 701 by clicking the first determine button 724. When the first determine button 724 is clicked, the output controller 52 shifts the display screen to the first basic screen 701, and then, displays the image that was displayed on the image display unit 800 of the first display setting screen 702 on the screen display unit 800 of the first basic screen 701 without change.

Figure 26:
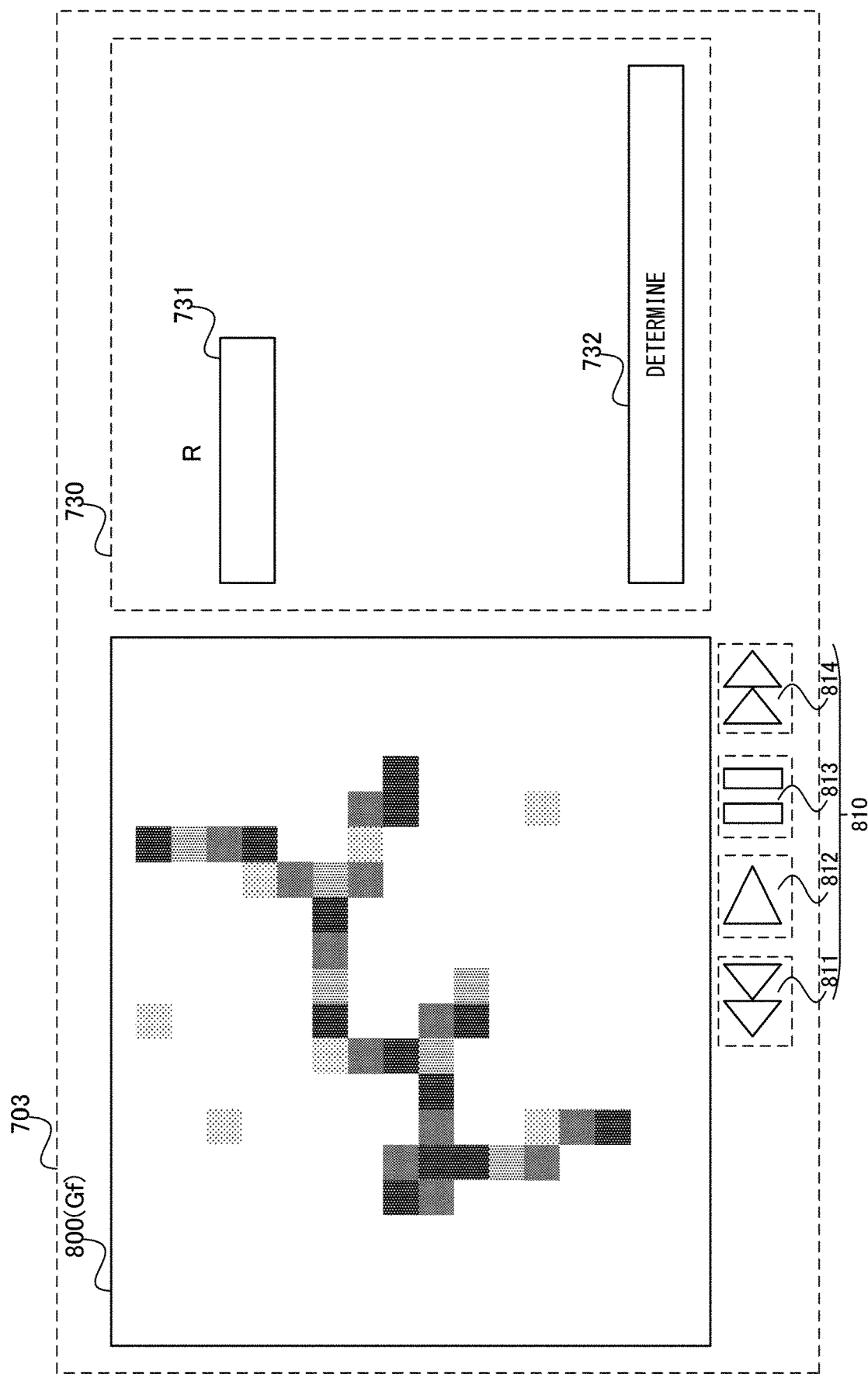
FIG. 26 is a conceptual view showing an example of the display screen according to Variant 10.

FIG. 26 is a view showing an example of the intersection detection parameter selection screen 703. The intersection detection parameter selection screen 703 includes the image display unit 800, a first parameter input part 730, and the video operation unit 810. The first parameter input part 730 includes a text box 731, and a second determine button 732. The output controller 52 can display the image displayed on the image display unit 800 of the first basic screen 701 so far on the image display unit 800 of the intersection detection parameter selection screen 703. In the example of FIG. 26, a fluorescent image Gf that is the captured image of the cell Ce is shown.

The text box 731 is an input element configured input the intersection detection parameter. The user can input a numerical value into the text box 731 using a keyboard or the like. A character of "R" indicating a type of an intersection detection parameter is displayed above the text box 731.

Further, as long as the intersection detection parameter can be input, the arbitrary input element other than the text box can be disposed in the first parameter input part 731.

The second determine button 732 is an input element configured to shift the display screen to the first basic screen 701 by clicking the second determine button 732. When the second determine button 732 is clicked, the pixel group setting part 512 sets the numerical value input into the text box 731 as the intersection detection parameter. In addition, the output controller 52 shifts the display screen to the first basic screen 701.

Figure 27:
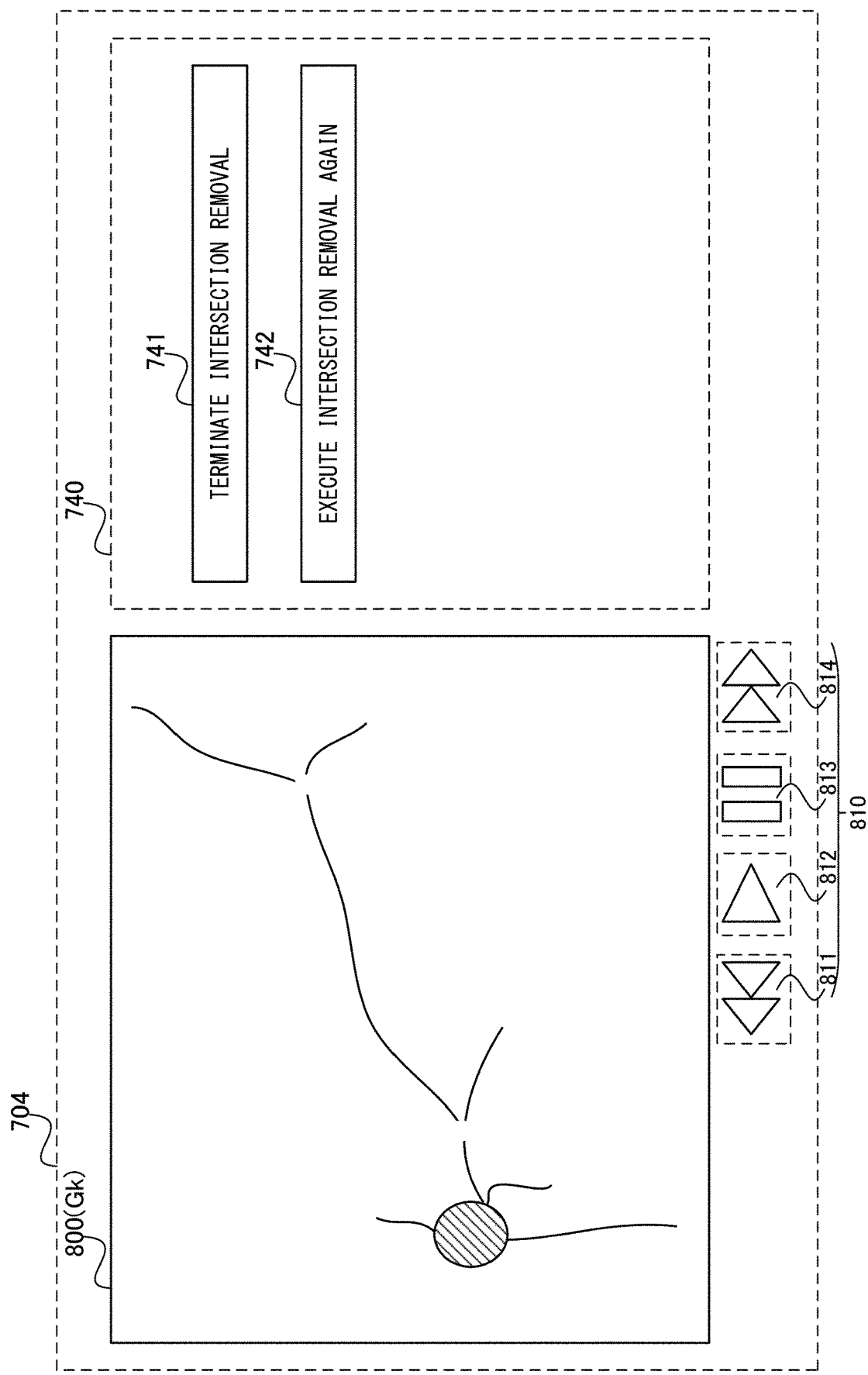
FIG. 27 is a conceptual view showing an example of the display screen according to Variant 10.

FIG. 27 is a view showing an example of the first result display screen 704. The first result display screen 704 includes the image display unit 800, a first determination input part 740, and the video operation unit 810. The first determination input part 740 includes a first end button 741 and a first re-execution button 742. The output controller 52 displays the intersection removing result image Gk obtained through the intersection removing processing on the image display unit 800 of the first result display screen 704. The user can observe the intersection removing result image Gk and input whether the user intends to terminate the intersection removing processing or perform the intersection removing processing again.

The first determination input part 740 includes the buttons 741 and 742 that are input elements configured to cause the image processing device 1 to perform a predetermined operation as the user clicks with a cursor using a mouse, a touch pad, or the like.

The first end button 741 is a button configured to terminate the intersection removing processing and proceed to setting and execution of the assignment processing by clicking the first end button 741. When the first end button 741 is clicked, the output controller 52 displays a second basic screen 705 of FIG. 28 that is a screen configured to perform setting of the assignment processing on the output part 44.

The first re-execution button 742 is a button configured to perform the intersection removing processing again by clicking the first re-execution button 742. When the first re-execution button 742 is clicked, the output controller 52 displays the first basic screen 701 on the output part 44.

Hereinafter, in the above-mentioned assignment processing, while the example of the display screen displayed on the output part 44 has been described, the aspect of the image in each display screen, shapes of the buttons and the icons, and the like, are not limited to that shown in each of the following drawings.

Figure 28:
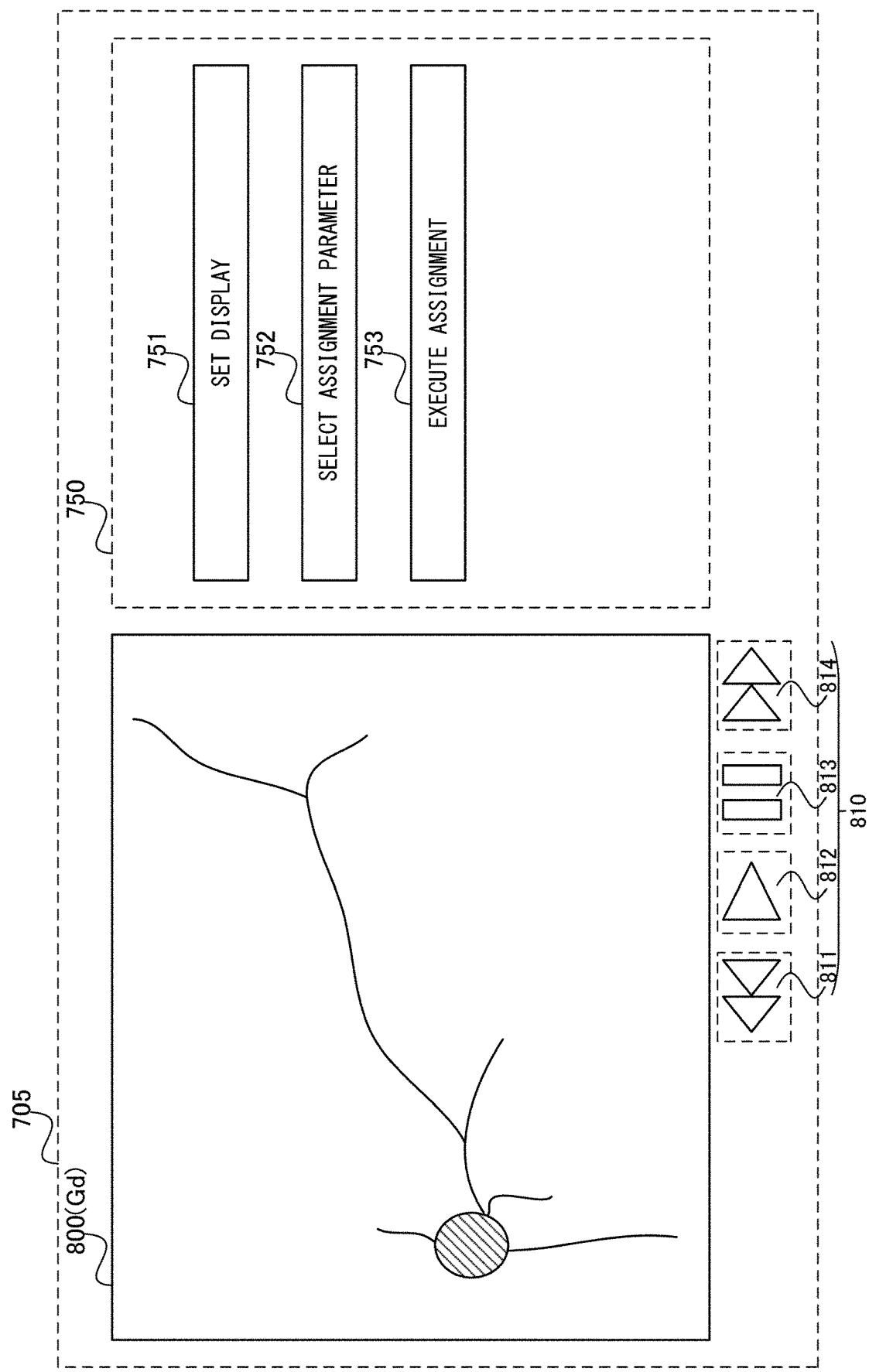
FIG. 28 is a conceptual view showing an example of the display screen according to Variant 10.

FIG. 28 is an example of the screen displayed on the output part 44 before the assignment processing is performed, and the screen is the second basic screen 705. The second basic screen 705 includes the image display unit 800, a second input element display unit 750, and the video operation unit 810. The second input element display unit 750 includes a second display setting button 751, an assignment parameter selection button 752, and the assignment execution button 753. While the detection result image Gd is shown on the image display unit 800 of FIG. 28, the image displayed on the image display unit 800 of the second basic screen 705 can be appropriately changed.

The second input element display unit 750 includes the buttons 751, 752 and 753 that are input element configured to cause the image processing device 1 to perform a predetermined operation as the user clicks with a cursor using a mouse, a touch pad, or the like.

The second display setting button 751 is an input element configured to shift the display screen to a second display setting screen that is a screen configured to set an image displayed on the image display unit 800. When the second display setting button 751 is clicked, the output controller 52 displays a second display setting screen 706 of FIG. 29 on the output part 44.

The assignment parameter selection button 752 is an input element configured to shift the display screen to an assignment parameter selection screen that is a screen configured to input an assignment parameter. When the assignment parameter selection button 752 is clicked, the output controller 52 displays an assignment parameter selection screen 707 of FIG. 30 on the output part 44.

The assignment execution button 753 is an input element configured to shift the display screen to a second result display screen that is a screen configured to display a result of the assignment processing while the data processing part 51 executes the assignment processing. When the assignment execution button 753 is clicked, the output controller 52 displays a second result display screen 708 of FIG. 31 on the output part 44.

Figure 29:
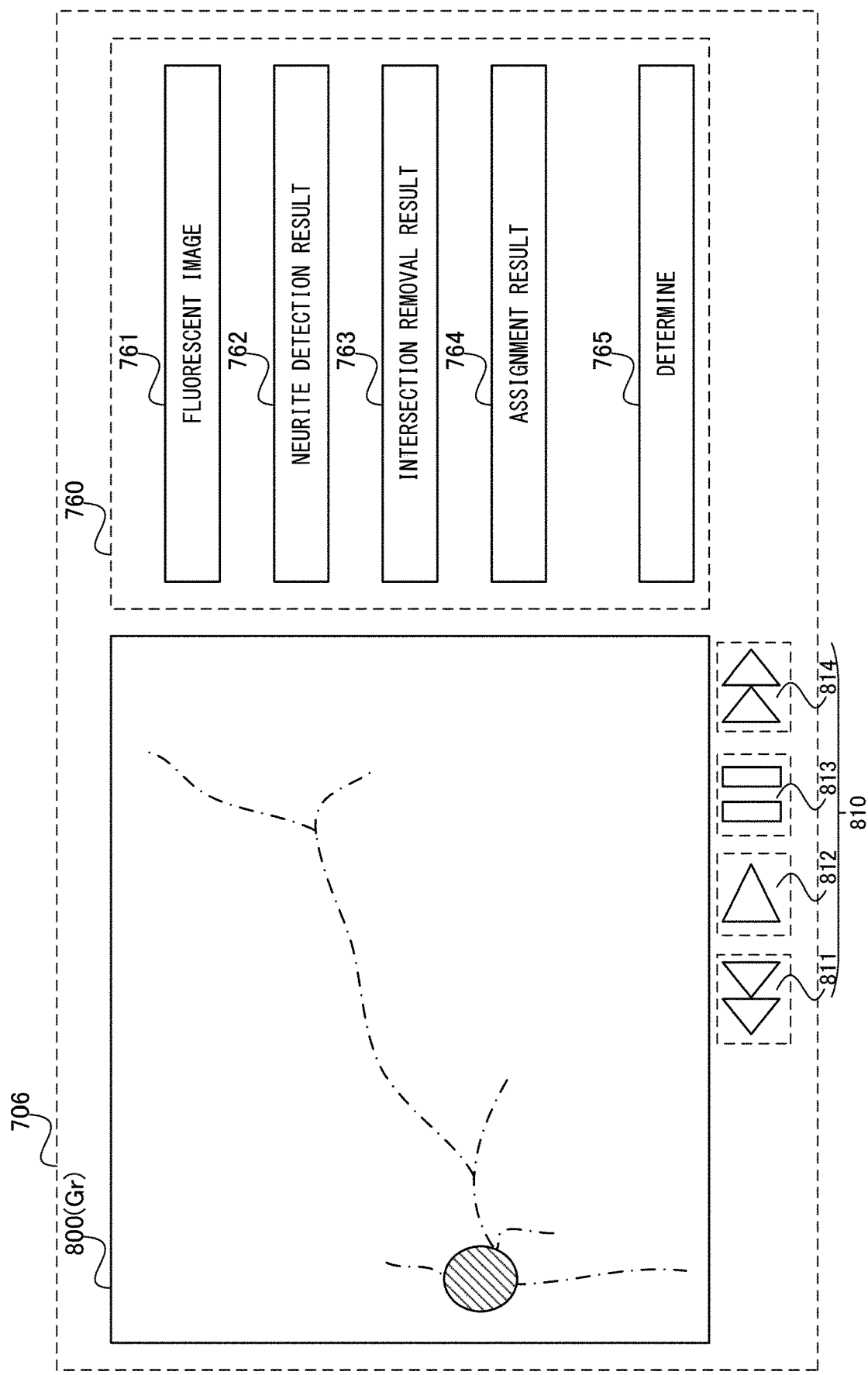
FIG. 29 is a conceptual view showing an example of the display screen according to Variant 10.

FIG. 29 is a view showing an example of the second display setting screen 706. The second display setting screen 706 includes the image display unit 800, a second image selection unit 760, and the video operation unit 810. The second image selection unit 760 includes a second captured image display button 761, a second detection result image display button 762, a second intersection removing result image display button 763, an assignment result image display button 764, and a third determine button 765. Before these buttons are clicked, the output controller 52 can display the image displayed on the second basic screen 705 or the like so far on the image display unit 800.

The second image selection unit 760 includes the buttons 761, 762, 763, 764 and 765 that are input elements configured to perform selection of the image displayed on the image processing unit 800 as the user clicks with a cursor using the mouse, the touch pad, or the like.

The second captured image display button 761 is an input element configured to display a captured image on the image display unit 800 by clicking the second captured image display button 761. When the second captured image display button 761 is clicked, the output controller 52 displays the captured image on the image display unit 800.

The second detection result image display button 762 is an input element configured to display the detection result image Gd on the image display unit 800 by clicking the second detection result image display button 762. When the second detection result image display button 762 is clicked, the output controller 52 displays the detection result image Gd on the image display unit 800.

The second intersection removing result image display button 763 is an input element configured to display the intersection removing result image Gk on the image display unit 800 by clicking the second intersection removing result image display button 763. When the second intersection removing result image display button 763 is clicked, the output controller 52 displays the intersection removing result image Gk on the image display unit 800.

The assignment result image display button 764 is an input element configured to display the above-mentioned assignment result image Or on the image display unit 800 by clicking the assignment result image display button 764. When the assignment result image display button 764 is clicked, the output controller 52 displays the assignment result image Gr on the image display unit 800. In the assignment result image Gr of FIG. 29, it is schematically shown by dashed lines that neurites of the same group are shown by the same color phase or the like.

The third determine button 765 is an input element configured to shift the display screen to the second basic screen 705 by clicking the third determine button 765. When the third determine button 765 is clicked, the output controller 52 shifts the display screen to the second basic screen 705, and then, displays the image that was displayed on the image display unit 800 of the second display setting screen 706 on the image display unit 800 of the second basic screen 705 without change.

Figure 30:
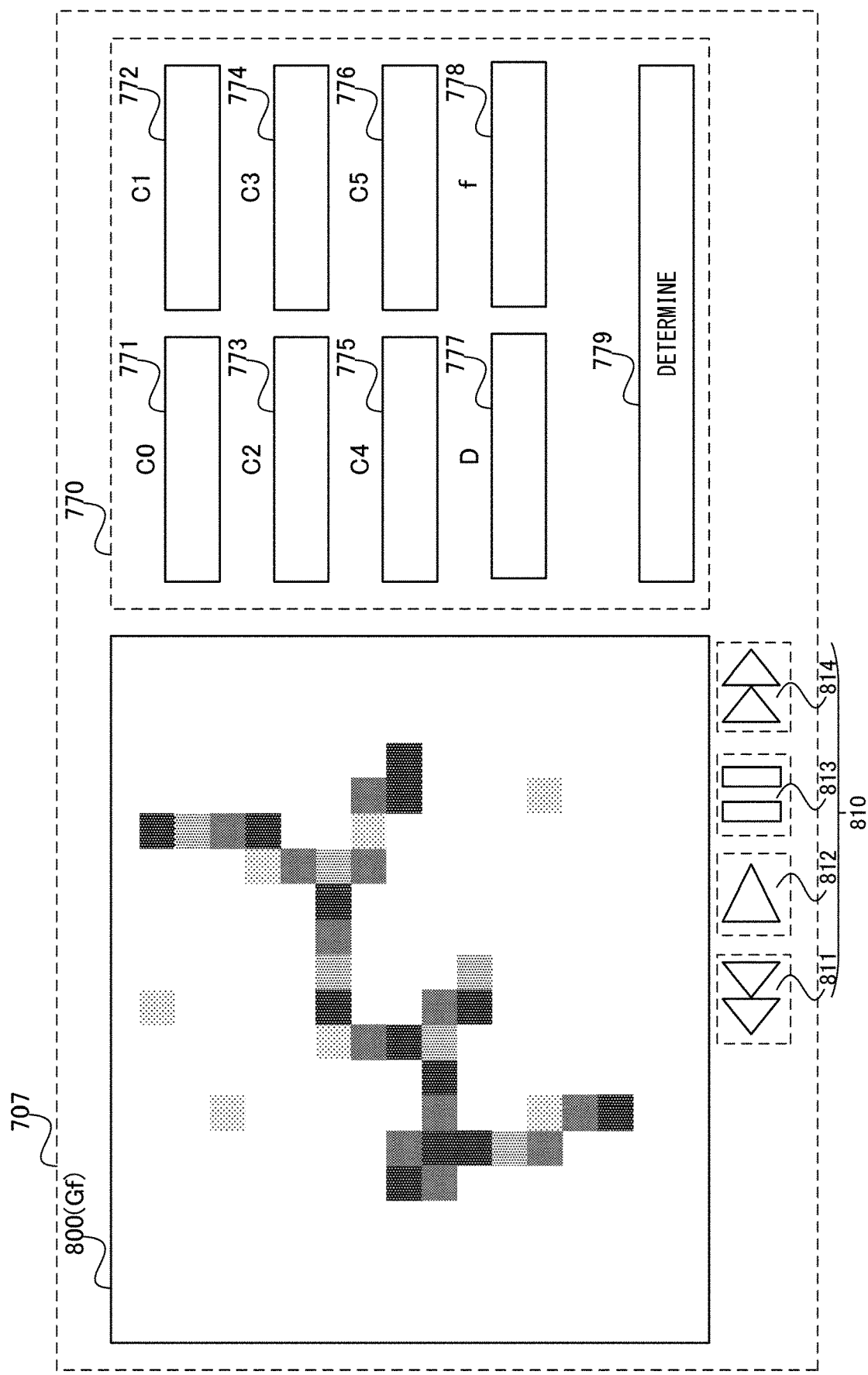
FIG. 30 is a conceptual view showing an example of the display screen according to Variant 10.

FIG. 30 is a view showing an example of the assignment parameter selection screen 707. The assignment parameter selection screen 707 includes the image display unit 800, a second parameter input part 770, and the video operation unit 810. The second parameter input part 770 includes a first text box 771, a second text box 772, a third text box 773, a fourth text box 774, a fifth text box 775, a sixth text box 776, a seventh text box 777, an eighth text box 778, and a fourth determine button 779. The output controller 52 can display the image displayed on the image display unit 800 of the second basic screen 705 so far on the image display unit 800 of the assignment parameter selection screen 707. In the example of FIG. 30, the fluorescent image Gf is shown.

The first text box 771, the second text box 772, the third text box 773, the fourth text box 774, the fifth text box 775, the sixth text box 776, the seventh text box 777 and the eighth text box 778 are input elements configured to input the assignment parameters c0, c1, c2, c3, c4, c5, D and f, respectively. The user can input numerical values into the text boxes 771 to 778 of the second parameter input part 770 using a keyboard or the like. Characters indicating types of assignment parameters are displayed above the text boxes 771 to 778 of the second parameter input part 770.

Further, if the assignment parameters can be input, arbitrary input elements other than the text boxes can be disposed in the parameter input part 731.

The fourth determine button 779 is an input element configured to shift the display screen to the second basic screen 705 by clicking the fourth determine button 779. When the fourth determine button 779 is clicked, the data processing part 51 sets the numerical values input into the text boxes 771 to 778 as the assignment parameters. In addition, the output controller 52 shifts the display screen to the second basic screen 705.

Figure 31:
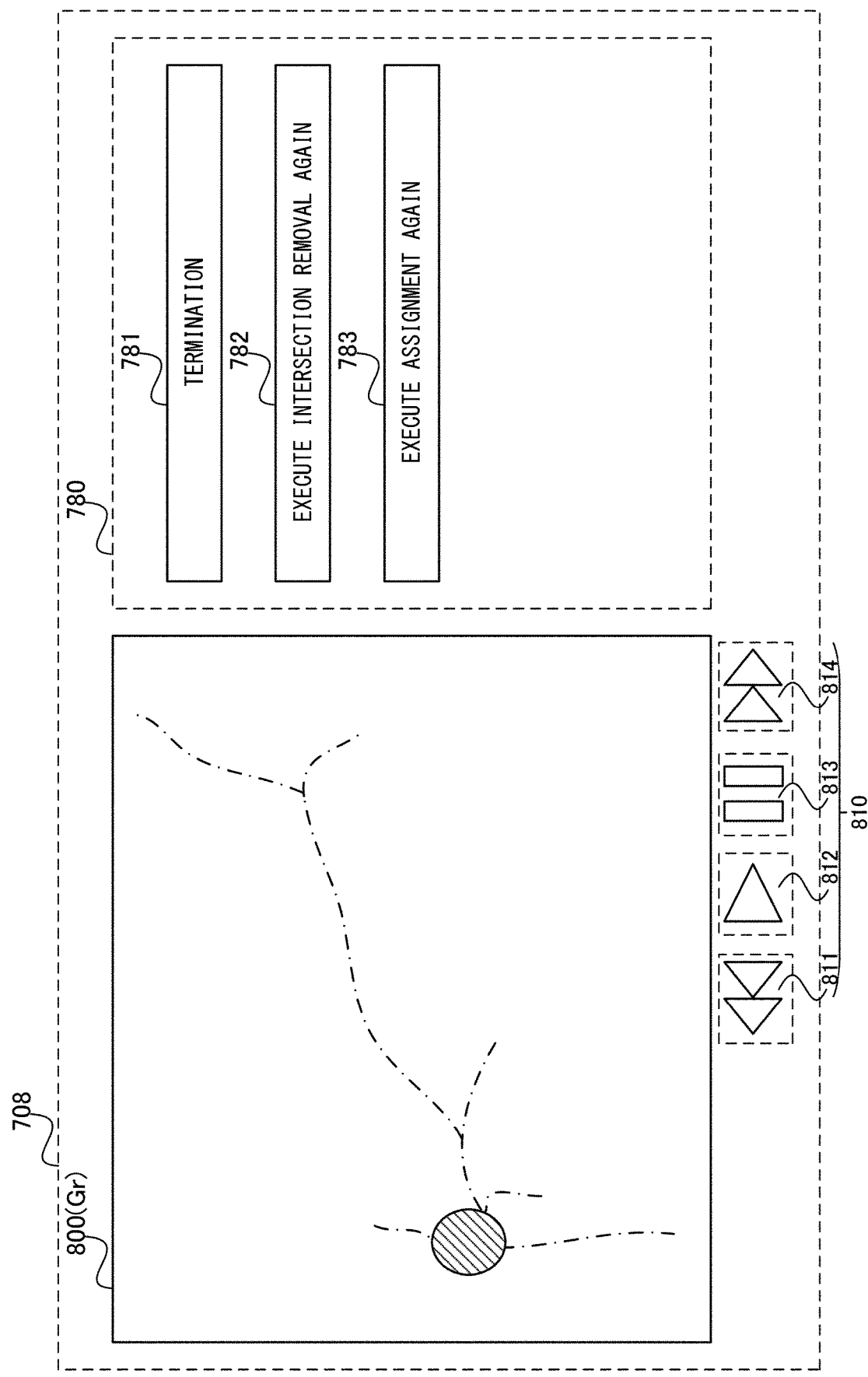
FIG. 31 is a conceptual view showing an example of the display screen according to Variant 10.

FIG. 31 is a view showing an example of the second result display screen 708. The second result display screen 708 includes the image display unit 800, a second determination input part 780, and the video operation unit 810. The second determination input part 780 includes a second end button 781, a second re-execution button 782, and a third re-execution button 783. The output controller 52 displays the assignment result image Gr obtained through assignment processing on the image display unit 800 of the second result display screen 708. The user can observe the assignment result image Gr and input whether the user intends to terminate the assignment processing or perform the intersection removing processing or the assignment processing again.

The second determination input part 780 includes the buttons 781, 782 and 783 that are input elements configured to cause the image processing device 1 to perform a predetermined operation as the user clicks a cursor using the mouse, the touch pad, or the like.

The second end button 781 is a button configured to terminate the assignment processing by clicking the second end button 781. When the second end button 781 is clicked, the data processing part 52 appropriately terminates the processing.

The second re-execution button 782 is a button configured to perform the intersection removing processing again by clicking the second re-execution button 782. When the second re-execution button 782 is clicked, the output controller 52 displays the first basic screen 701 on the output part 44.

The third re-execution button 782 is a button configured to perform the assignment processing again by clicking the third re-execution button 783. When the third re-execution button 783 is clicked, the output controller 52 displays the second basic screen 705 on the output part 44.

In the image processing method of the variant, the user can adjust the parameters for these processing while checking the result of the intersection removing processing and the result of the assignment processing. Accordingly, for each specific captured image, how the pixel group such as the segment S or the like corresponds to the linear portion can be accurately analyzed. In addition, according to the screen shift as described above, since the above-mentioned parameter can be input while observing the image showing the result of the intersection removing processing or the result of the assignment processing according to necessity, the analysis can be efficiently performed.

The present invention is not limited to the content of the embodiment. Other aspects that can be considered within the scope of the technical aspect of the present invention are also included without departing from the scope of the present invention.

What is claimed is:

1. An image processing device comprising:
   a processor, and
   a memory containing instructions which, when executed by the processor, cause the processor to perform the following:
   a pixel group setting process of obtaining an image data of a first image which shows a target object including a linear portion from an imaging device, and of setting a plurality of pixel groups including a first pixel group and a second pixel group, which are not connected to each other, after removing a pixel corresponding to a cross from a pixel constituting a pixel of the first image when setting a plurality of pixel groups corresponding to the first image;
   a pair setting process of performing setting of a pair of the first pixel group and the second pixel group including a pixel within a predetermined range from the first pixel group, among the plurality of pixel groups, in order to calculate a connecting degree of the second pixel group with respect to the first pixel group; and
   a calculation process of calculating the connecting degree of the pair set by the pair setting process,
   wherein the predetermined range is a search range set on the basis of a first distance between the first pixel group and the second pixel group, or a search range set on the basis of a first angle formed between a first line segment corresponding to the first pixel group and a second line segment corresponding to the second pixel group, and
   the calculation process calculates the first distance or the first angle, and calculates the connecting degree using the first distance or the first angle.

2. The image processing device according to claim 1, wherein the instructions further cause the processor to perform the following:
   the calculation process calculating at least one of a second angle, which is formed between the first line segment and a third line segment passing through a point included in the first pixel group and a point included in the second pixel group, and a third angle, which is formed between the third line segment and the second line segment, and calculating the connecting degree on the basis of at least one of the second angle and the third angle.

3. The image processing device according to claim 2, wherein the instructions further cause the processor to perform the following:
   the calculation process calculating at least one of a fourth angle, which is formed between the first line segment and a fourth line segment that is shortest in the third line segments, and a fifth angle, which is formed between the fourth line segment and the second line segment, and calculating the connecting degree on the basis of at least one of the fourth angle and the fifth angle.

4. The image processing device according to claim 1, wherein the instructions further cause the processor to perform the following:
the pair setting process performing setting of the pair for each of pixel groups that constitute the plurality of pixel groups,
the calculation process calculating the connecting degree for each of the pair, and
a determination process determining grouping of the plurality of pixel groups on the basis of the calculated connecting degree is provided.

5. The image processing device according to claim 4, wherein the instructions further cause the processor to perform the following:
provided that each of the plurality of pixel groups is a node and the connecting degree is a weight of an edge, the determination process sequentially determining which group the node belongs to on the basis of a minimum spanning tree obtained by a Prim's algorithm, a Kruskal's algorithm or a Boruvka's algorithm.

6. The image processing device according to claim 5, wherein the instructions further cause the processor to perform the following:
the determination process comprises a termination determining process determining whether processing of obtaining the minimum spanning tree is terminated on the basis of a sum of numerical values corresponding to a plurality of edges that are selected when edges are selected in the Prim's algorithm, the Kruskal's algorithm or the Boruvka's algorithm.

7. The image processing device according to claim 4, wherein the instructions further cause the processor to perform comprising an image generating process of generating a second image showing a result of the grouping.

8. The image processing device according to claim 2, wherein the instructions further cause the processor to perform the following:
the calculation process calculating the connecting degree such that a pair of the segments of the cross pixel group corresponds to a part of a connected linear region.

9. The image processing device according to claim 2, wherein the instructions further cause the processor to perform the following:
the pixel group setting process comprising a cross pixel group setting process collectively setting four pixel groups including the first pixel group and three of the pixel groups as the cross pixel group when there are three other pixel groups within a certain range from the first pixel group, and
the calculation process calculating the connecting degree such that a pair of the cross pixel group facing each other with the cross sandwiched therebetween corresponds to a part of a connected linear region.

10. The image processing device according to claim 2, wherein the instructions further cause the processor to perform the following:
the calculation process calculating the connecting degree on the basis of at least one of an average value of luminance of a plurality of pixels that constitute the first pixel group or the second pixel group, a width of the first pixel group or the second pixel group, a curvature of a curved line when the first pixel group or the second pixel group is made to correspond to the curved line, and a length of a line segment that constitutes a broken line when the first pixel group or the second pixel group is made to correspond to the broken line.

11. The image processing device according to claim 1, wherein the instructions further cause the processor to perform the following:
the pair setting process setting a pair of the first pixel group and the second pixel group including a pixel within the predetermined range set corresponding to a pixel located at an end of the first pixel group, a center of gravity of the first pixel group, or a center of a rectangle that circumscribe the first pixel group, among the plurality of pixel groups.

12. The image processing device according to claim 1, wherein the first image is an image obtained by performing image processing on an image obtained by imaging the object and is a binary image showing whether each pixel of the first image corresponds to a linear structure according to a pixel value, and
wherein the instructions further cause the processor to perform the pixel group setting process setting the plurality of pixel groups on the basis of the pixel value.

13. The image processing device according to claim 1, wherein the first image is an image showing a plurality of pixels corresponding to neurites, and
the connecting degree is a numerical value indicating possibility that the first pixel group and the second pixel group correspond to a part of the neurites extending from a same neuron.

14. The image processing device according to claim 1, wherein the first image is an image showing a plurality of pixels corresponding to a blood vessel, and
the connecting degree is a numerical value indicating possibility that the first pixel group and the second pixel group correspond to a part of a same blood vessel.

15. The image processing device according to claim 1, wherein the instructions further cause the processor to execute an operation includes:
the pixel group setting process removing the cross by setting a removed pixel region, the removed pixel region being a region having a center at a center pixel in a first partial image which is an image of a portion of the first image.

16. The image processing device according to claim 15, wherein the instructions further cause the processor to perform the following:
when removing the cross, the pixel group setting process setting an intersection detection parameter which indicates a size of the removed pixel region by indicating a number of pixel of the removed pixel region in at least one of a lateral direction or a longitudinal direction.

17. An image processing method comprising:
setting process of obtaining an image data of a first image which shows a target object including a linear portion from an imaging device and setting a plurality of pixel groups including a first pixel group and a second pixel group, which are not connected to each other, after removing a pixel corresponding to a cross from a pixel constituting a pixel of the first image when setting a plurality of pixel groups corresponding to the first image in the imaging device;
setting process of setting a pair of the first pixel group and the second pixel group including a pixel within a predetermined range from the first pixel group, among the plurality of pixel groups, in order to calculate a connecting degree of the second pixel group with respect to the first pixel group; and
calculating process of calculating the connecting degree of the pair set in the setting process of the pair of the first pixel group and the second pixel group, wherein the predetermined range is a search range set on the basis of a first distance between the first pixel group and the second pixel group, or a search range set on the basis of a first angle formed between a first line segment corresponding to the first pixel group and a second line segment corresponding to the second pixel group, and in the calculating process, the first distance or the first angle is calculated and the connecting degree is calculated by using the first distance or the first angle.

18. A non-transitory computer-readable storage medium storing a program containing instructions which cause a processing device to perform the following:

pixel group setting processing of obtaining an image data of a first image which shows a target object including a linear portion from an imaging device and setting a plurality of pixel groups including a first pixel group and a second pixel group, which are not connected to each other, after removing a pixel corresponding to a cross from a pixel constituting a pixel of the first image based on the image data when setting a plurality of pixel groups corresponding to the first image in the imaging device;

pair setting processing of performing setting of a pair of the first pixel group and the second pixel group including a pixel within a predetermined range from the first pixel group, among the plurality of pixel groups, in order to calculate a connecting degree of the second pixel group with respect to the first pixel group, and calculating process of calculating the connecting degree of the pair set in the pair setting processing.

* * * * *